(12) United States Patent
Aimetti et al.

(10) Patent No.: US 11,266,662 B2
(45) Date of Patent: *Mar. 8, 2022

(54) GANAXOLONE FOR USE IN PROPHYLAXIS AND TREATMENT OF POSTPARTUM DEPRESSION

(71) Applicant: Marinus Pharmaceuticals, Inc., Radnor, PA (US)

(72) Inventors: Alex Aimetti, Radnor, PA (US); Christopher Cashman, Radnor, PA (US); Lorianne Masuoka, Chestnut Hill, MA (US); Jaakko Lappalainen, Wilmington, DE (US)

(73) Assignee: Marinus Pharmaceuticals, Inc., Radnor, PA (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/705,541

(22) Filed: Dec. 6, 2019

(65) Prior Publication Data
US 2020/0179403 A1 Jun. 11, 2020

Related U.S. Application Data

(60) Provisional application No. 62/776,805, filed on Dec. 7, 2018.

(51) Int. Cl.
*A61K 31/57* (2006.01)
*A61P 25/24* (2006.01)
*A61K 9/00* (2006.01)

(52) U.S. Cl.
CPC ............ *A61K 31/57* (2013.01); *A61K 9/0019* (2013.01); *A61K 9/0053* (2013.01); *A61P 25/24* (2018.01)

(58) Field of Classification Search
CPC .............................. A61K 31/573; A61K 31/57
See application file for complete search history.

(56) References Cited

U.S. PATENT DOCUMENTS

| | | |
|---|---|---|
| 2,671,750 A | 3/1954 | Macek |
| 4,540,602 A | 9/1985 | Motoyama et al. |
| 4,783,484 A | 11/1988 | Violante et al. |
| 4,826,689 A | 5/1989 | Violanto et al. |
| 4,997,454 A | 3/1991 | Violante et al. |
| 5,134,127 A | 7/1992 | Stella et al. |
| 5,145,684 A | 9/1992 | Liversidge et al. |
| 5,209,746 A | 5/1993 | Balahan et al. |
| 5,213,808 A | 5/1993 | Bar-Shalom et al. |
| 5,221,278 A | 6/1993 | Linkwitz et al. |
| 5,260,068 A | 11/1993 | Chen |
| 5,260,069 A | 11/1993 | Chen |
| 5,298,262 A | 3/1994 | Na et al. |
| 5,299,131 A | 3/1994 | Haas et al. |
| 5,308,348 A | 5/1994 | Balaban et al. |
| 5,312,390 A | 5/1994 | Wong |
| 5,318,588 A | 6/1994 | Horzewski et al. |
| 5,340,590 A | 8/1994 | Wong et al. |
| 5,346,702 A | 9/1994 | Na et al. |
| 5,352,459 A | 10/1994 | Hollister et al. |
| 5,356,476 A | 10/1994 | Oshlack et al. |
| 5,376,645 A | 12/1994 | Stella et al. |
| 5,391,381 A | 2/1995 | Wong et al. |
| 5,399,363 A | 3/1995 | Liversidge et al. |
| 5,429,824 A | 7/1995 | June |
| 5,445,829 A | 8/1995 | Paradissis et al. |
| 5,456,679 A | 10/1995 | Balaban et al. |
| 5,470,583 A | 11/1995 | Na et al. |
| 5,472,708 A | 12/1995 | Chen |
| 5,494,683 A | 2/1996 | Liversidge et al. |
| 5,508,040 A | 4/1996 | Chen |
| 5,510,116 A | 4/1996 | Bosch et al. |
| 5,518,187 A | 5/1996 | Bruno et al. |
| 5,534,270 A | 7/1996 | De Castro |
| 5,543,133 A | 8/1996 | Swanson et al. |
| 5,556,847 A | 9/1996 | Johnson et al. |
| 5,560,932 A | 10/1996 | Bagchi et al. |
| 5,573,783 A | 11/1996 | Desieno et al. |
| 5,629,277 A | 5/1997 | Plishka |
| 5,662,883 A | 9/1997 | Bagchi et al. |
| 5,665,331 A | 9/1997 | Bagchi et al. |
| 5,672,360 A | 9/1997 | Sackler et al. |
| 5,718,388 A | 2/1998 | Czekai et al. |
| 5,741,522 A | 4/1998 | Violante et al. |
| 5,776,496 A | 7/1998 | Violante et al. |
| 5,840,329 A | 11/1998 | Bai |
| 5,862,999 A | 1/1999 | Czekai et al. |
| 5,888,996 A | 3/1999 | Farb |

(Continued)

FOREIGN PATENT DOCUMENTS

| | | |
|---|---|---|
| EP | 0169618 A2 | 1/1986 |
| EP | 0498824 A1 | 8/1992 |

(Continued)

OTHER PUBLICATIONS

Prescribing Information for Zulpresso™ (brexanolone) 2019.
Fabian, "Azabenzenes (azines)—The nitrogen derivatives of benzene with one to six N atoms: Stability, homodesmotic stabilization energy, electron distribution, and magnetic ring current; a computational study" Canadian J. Chem. 2004, 82, 50-69.
International Search Report of the International Searching Authority for International Application No. PCT/US2016/016977; Date of Filing: Feb. 8, 2016; dated Apr. 26, 2016; 6 pages.

(Continued)

*Primary Examiner* — Rei Tsang Shiao
(74) *Attorney, Agent, or Firm* — Hogan Lovells US LLP

(57) ABSTRACT

Uses of ganaxolone in prophylaxis and treatment of postpartum depression are described. A dose of ganaxolone is administered to a female suffering from postpartum depression or at risk of developing postpartum depression in an amount and at a rate sufficient to alleviate at least one symptom of postpartum depression in the female.

20 Claims, 39 Drawing Sheets

(56) References Cited

U.S. PATENT DOCUMENTS

| | | | |
|---|---|---|---|
| 5,980,508 A | 11/1999 | Cardamone et al. | |
| 6,039,979 A | 3/2000 | Gendrot et al. | |
| 6,161,536 A | 12/2000 | Redmon et al. | |
| 6,214,379 B1 | 4/2001 | Hermelin | |
| 6,228,398 B1 | 5/2001 | Devane et al. | |
| 6,248,363 B1 | 6/2001 | Patel et al. | |
| 6,264,922 B1 | 7/2001 | Wood et al. | |
| 6,267,989 B1 | 7/2001 | Liversidge et al. | |
| 6,316,029 B1 | 11/2001 | Jain et al. | |
| 6,375,986 B1 | 4/2002 | Ryde et al. | |
| 6,423,746 B1 | 7/2002 | Yarbrough et al. | |
| 6,428,814 B1 | 8/2002 | Bosch et al. | |
| 6,432,381 B2 | 8/2002 | Liversidge et al. | |
| 6,514,518 B2 | 2/2003 | Monkhouse et al. | |
| 6,569,463 B2 | 5/2003 | Patel et al. | |
| 6,592,903 B2 | 7/2003 | Ryde et al. | |
| 6,607,751 B1 | 8/2003 | Odidi et al. | |
| 6,627,223 B2 | 9/2003 | Percel et al. | |
| 6,682,759 B2 | 1/2004 | Lim et al. | |
| 6,689,378 B1 | 2/2004 | Sun et al. | |
| 6,730,325 B2 | 5/2004 | Devane et al. | |
| 6,793,936 B2 | 9/2004 | Devane et al. | |
| 6,902,742 B2 | 6/2005 | Devane et al. | |
| 6,908,626 B2 | 6/2005 | Cooper et al. | |
| 6,923,988 B2 | 8/2005 | Patel et al. | |
| 6,969,529 B2 | 11/2005 | Bosch et al. | |
| 6,976,647 B2 | 12/2005 | Reed et al. | |
| 7,078,057 B2 | 7/2006 | Kerkhof | |
| 7,198,795 B2 | 4/2007 | Cooper et al. | |
| 7,550,445 B2 | 6/2009 | Nerurkar et al. | |
| 7,635,773 B2 | 12/2009 | Antle | |
| 7,858,609 B2 | 12/2010 | Shaw et al. | |
| 8,022,054 B2 | 9/2011 | Shaw et al. | |
| 8,318,714 B2 | 11/2012 | Shaw et al. | |
| 8,362,286 B2 | 1/2013 | Shaw et al. | |
| 8,367,651 B2 | 2/2013 | Shaw et al. | |
| 8,410,077 B2 | 4/2013 | Antle | |
| 8,455,002 B2 | 6/2013 | Shaw et al. | |
| 8,604,011 B2 | 12/2013 | Mellon | |
| 8,618,087 B2 | 12/2013 | Shaw et al. | |
| 8,658,692 B2 | 2/2014 | Kim et al. | |
| 9,017,728 B2 | 4/2015 | Shaw et al. | |
| 9,029,355 B2 | 5/2015 | Shaw et al. | |
| 9,056,116 B2 | 6/2015 | Shaw et al. | |
| 9,200,088 B2 | 12/2015 | Antle | |
| 9,452,176 B2 | 9/2016 | Shaw et al. | |
| 9,750,822 B2 | 9/2017 | Antle | |
| 10,117,951 B2 | 11/2018 | Antle | |
| 10,251,894 B2 | 4/2019 | Rogawski et al. | |
| 10,322,139 B2 | 6/2019 | Reddy | |
| 10,391,105 B2* | 8/2019 | Cashman | A61K 47/10 |
| 10,639,317 B2* | 5/2020 | Cashman | A61K 47/36 |
| 2002/0012675 A1 | 1/2002 | Jain et al. | |
| 2002/0150616 A1 | 10/2002 | Vandecruys | |
| 2003/0054042 A1 | 3/2003 | Liversidge et al. | |
| 2003/0129242 A1 | 7/2003 | Bosch et al. | |
| 2003/0215502 A1 | 11/2003 | Pruss et al. | |
| 2004/0067251 A1 | 4/2004 | Johnston et al. | |
| 2004/0105889 A1 | 6/2004 | Ryde et al. | |
| 2004/0214746 A1 | 10/2004 | Bosch et al. | |
| 2004/0224020 A1 | 11/2004 | Schoenhard | |
| 2004/0258757 A1 | 12/2004 | Bosch et al. | |
| 2005/0031691 A1 | 2/2005 | McGurk et al. | |
| 2005/0118268 A1 | 6/2005 | Percel et al. | |
| 2005/0181050 A1 | 8/2005 | Hirsh et al. | |
| 2005/0226927 A1 | 10/2005 | Han et al. | |
| 2005/0232890 A1 | 10/2005 | Hoath et al. | |
| 2006/0003005 A1 | 1/2006 | Cao et al. | |
| 2006/0216353 A1 | 9/2006 | Liversidge et al. | |
| 2007/0141161 A1 | 6/2007 | Shaw et al. | |
| 2007/0148252 A1 | 6/2007 | Shaw et al. | |
| 2009/0004262 A1 | 1/2009 | Shaw et al. | |
| 2011/0236487 A1 | 9/2011 | Shaw et al. | |
| 2012/0052098 A1 | 3/2012 | Shaw et al. | |
| 2012/0316146 A1 | 12/2012 | Goodchild et al. | |
| 2014/0057885 A1 | 2/2014 | Reddy et al. | |
| 2014/0235600 A1 | 8/2014 | Covey et al. | |
| 2014/0249120 A1 | 9/2014 | Covey et al. | |
| 2015/0018327 A1 | 1/2015 | Reddy | |
| 2015/0158903 A1 | 6/2015 | Upasani et al. | |
| 2015/0175651 A1 | 6/2015 | Salituro et al. | |
| 2015/0291654 A1 | 10/2015 | Upasani et al. | |
| 2015/0313915 A1 | 11/2015 | Rogawski et al. | |
| 2015/0315230 A1 | 11/2015 | Covey et al. | |
| 2016/0228454 A1 | 8/2016 | Zhang et al. | |
| 2017/0202855 A1 | 7/2017 | Shaw et al. | |
| 2017/0258812 A1 | 9/2017 | Zhang et al. | |
| 2017/0348327 A1 | 12/2017 | Kanes et al. | |
| 2018/0071315 A1 | 3/2018 | Cashman et al. | |
| 2018/0296487 A1 | 10/2018 | Saporito et al. | |
| 2019/0117673 A1 | 4/2019 | Shaw et al. | |
| 2019/0117674 A1 | 4/2019 | Shaw et al. | |
| 2019/0160078 A1 | 4/2019 | Masuoka et al. | |
| 2019/0167698 A1 | 6/2019 | Cashman et al. | |
| 2020/0289530 A1 | 9/2020 | Cashman et al. | |

FOREIGN PATENT DOCUMENTS

| | | |
|---|---|---|
| EP | 0499299 A2 | 8/1992 |
| EP | 0580690 A1 | 2/1994 |
| WO | 9526715 A2 | 10/1995 |
| WO | 9857648 A1 | 12/1998 |
| WO | 0145677 A1 | 6/2001 |
| WO | 2011088503 A1 | 7/2011 |
| WO | 2014085668 A1 | 6/2014 |
| WO | 2014127201 A1 | 8/2014 |
| WO | 2014160441 A1 | 10/2014 |
| WO | 2014160480 A1 | 10/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015081170 | 6/2015 |
| WO | 2015180679 A1 | 12/2015 |
| WO | 2017156103 A1 | 9/2017 |
| WO | WO2017/156103 A1 | 9/2017 |
| WO | WO2019/094724 A1 | 5/2019 |

OTHER PUBLICATIONS

Liptakova et al.; "Effect of Ganaxolone on Flurothyl Seizures in Developing Rats"; Epilepsia, vol. 47, No. 7; Jan. 2000; pp. 788-793.

Marinus Pharmaceuticals: "Marinus Pharmaceuticals, Inc. Enters Into Use Agreement with CyDex Pharmaceuticals, Inc. for Use of Captisol(R) for Ganaxolone IV"; Aug. 12, 2014; retreived from internet.

Monaghan et al., "Initial Human Experience with Ganaxolone, a Neuroactive Steroid with Antiepileptic Activity" Epilepsia, 1997, vol. 38, Issue 9, pp. 1026-1031.

Mula; "Emerging drugs for focal epilepsy"; Expert Opinion, vol. 18, No. 1; Mar. 2013; pp. 87-95.

Sham et al., "Formulation and characterization of spray-dried powders containing nanoparticles for aerosol delivery to the lung" International Journal of Pharmaceuticals, vol. 269, 2004, pp. 45.

Valotis et al., "Human Receptor Kinetics, Tissue Binding Affinity, and Stability of Mornetasone Furoate" Journal of Pharmaceutical Sciences, May 2004, vol. 93, No. 5., 14 Pages.

Written Opinion of The International Searching Authority for International Application No. PCT/US2016/016977; Date of Filing: Feb. 8, 2016; dated Apr. 26, 2016; 8 pages.

Hogenkamp et al.; "Synthesis and in Vitro Activity of 3Beta-Substituted-3Alpha-hydroxypregnan-20-ones:Allocteric Modulations of the GABA(A) Receptor"; J. Med. Chem. 40; pp. 61-72; (1997).

Nohria et al.; "Ganaxolone"; The Journal of the American Society for Experimental NeuroTherapeutics; 4; pp. 102-105; (2007).

Pramanick et al.; "Excipient Selection In Parenteral Formulation Development"; Pharma Times, vol. 45, No. 3; Mar. 2013; pp. 65-77.

Rogawski et al.; "Neuroactive Steroids for the Treatment of Status Epilepticus"; Epilepsia, vol. 54, No. 6; 2013; pp. 93-98.

(56) References Cited

OTHER PUBLICATIONS

Rosetti et al.; "Management of Refractory Status Epilepticus in Adults: Still More Questions Than Answers"; Lancet Nuerol., vol. 10; Oct. 2011: pp. 922-930.
Shorvon et al.; "The Treatment of Super-Refractory Status Epilepticus: A Critical Review of Available Therapies and a Clinical Treatment Protocol"; BRAIN, vol. 134; 2011; pp. 2802-2818.
Botella et al. "Neuoractive Steroid. 1. Postitive Allosteric Modulators of the (χ-Aminobutyric Acid)A Receptor: Structure—Activity Relationships of Heterocyclic Substitution at C-21" Journal of Medicinal Chemistry; 58, pp. 3500-3511 (2015).
Pieribone et al., "Clinical Evaluation of Ganaxolone in Pediatric and Adolescent Patients with Refractory Epilepsy" Blackwell Publishing, Inc., Epilepsia, 48(10), pp. 1870-1874 (2007).
Wong et al. "Suspensions for intravenous (IV) injection: A review of development, preclinical and clinical aspects" Advanced Drug Delivery Reviews, 60, pp. 939-954, (2008).
Moyne et al. "Sterilization of injectable drugs solutions by irradiation" Radiation Physics and Chemistry, 63, pp. 703-703 (2002).
International Search Report and Written Opinion from International PCT Application No. PCT/US2016/057120 dated Jan. 31, 2017.
Reddy et al. "Neurosteroids—Endogenous Regulators of Seizure Susceptibility and Role in the Treatment of Epilespy", Jasper's Basic Mechanisms of the Epilepsies, 2012, pp. 1-29; p. 15; p. 19.
International Search Report and Written Opinion from International PCT Application No. PCT/US18/60037 dated Jan. 24, 2019.
Lyden et al. "Effect of Ganaxolone in a Rodent Model of Cerebral Hematoma", American Heart Association, Inc. (2000); pp. 169-175.
Loftsson et al. "Cyclodextrins in drug review," Expert Opinion, (Mar. 2005).
International Search Report and Written Opinion from International PCT Application No. PCT/US2019/064850, Date of filing: Dec. 6, 2018, dated Feb. 25, 2020, 7 pages.

\* cited by examiner

GANAXOLONE FOR USE IN PROPHYLAXIS AND TREATMENT OF POSTPARTUM DEPRESSION

This application claims the benefit of U.S. Provisional Application No. 62/776,805, filed on Dec. 7, 2018, hereby incorporated by reference.

BACKGROUND OF THE INVENTION

Plasma levels of allopregnanolone, which is a metabolite of progesterone and an endogenous gamma-aminobutyric acid (GABA) receptor modulator, are known to increase throughout pregnancy and then precipitously drop after delivery. Failure of $GABA_A$ receptors to adapt to these changes at parturition has been postulated to have a role in triggering postpartum depression.

Postpartum depression (PPD) is a mood disorder observed in an estimated 10-20% of all mothers who give birth. The disorder mirrors symptoms of a major depressive episode (e.g., feelings of extreme sadness, hopelessness, suicidal ideation, anxiety, and fatigue), with the additional criteria that the onset of depression occurs within 4 weeks of childbirth.

Selective serotonin reuptake inhibitors ("SSRIs") and serotonin and norepinephrine reuptake inhibitors (SNRIs) are commonly used off-label to manage postpartum depression. SSRIs are known to increase allopregnanolone, and it has been suggested that this mechanism could explain why SSRIs have shown therapeutic effect in the treatment of postpartum depression. The onset of efficacy for SSRIs ranges from at least 1-2 weeks to months, and response rates remain low.

Brexanolone, a proprietary formulation of the endogenous human hormone allopregnanolone, previously known as Sage-547, is marketed by Sage Therapeutics, Inc. for the treatment of postpartum depression.

Another synthetic analog of allopregnanolone is ganaxolone. The chemical structure of ganaxolone differs from brexanolone by one methyl group:

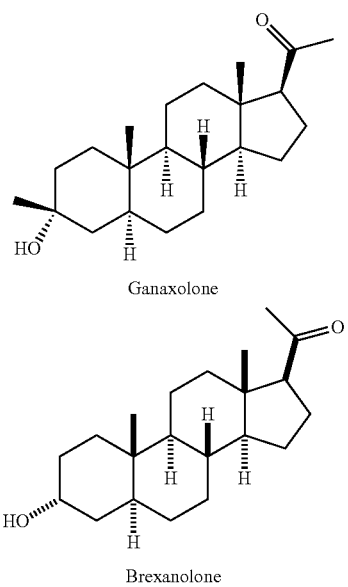

Ganaxolone

Brexanolone

Ganaxolone has a methyl group at position 3 in addition to the hydroxyl group; brexanolone lacks the methyl group at position 3.

Administration of brexanolone for the treatment of postpartum depression comprises intravenous administration of brexanolone in β-cyclodextrin-based intravenous formulation over 60 hours in three phases: (i) a titration phase for the first 24 hours; (ii) a maintenance phase for the next 28 hours; and (iii) a taper phase for the last 8 hours.

Two dose regimens are used to administer brexanolone—a 60 μg brexanolone dose regimen and a 90 μg brexanolone dose regimen.

The 60 μg brexanolone dose regimen consists of administration of 30 μg/kg/hr brexanolone for the first 4 hours, followed by administration of 60 μg/kg/hr brexanolone for the next 52 hours ($5^{th}$ to $56^{th}$ hours); followed by administration of 30 μg/kg/hr brexanolone for the next four hours ($56^{th}$ to $60^{th}$ hours) ("the 60 μg brexanolone dose regimen").

The 90 μg brexanolone dose regimen consists of administration of a dose of 30 μg/kg/hr brexanolone for the first 4 hours, followed by administration of 60 μg/kg/hr brexanolone for the next 20 hours, followed by administration of 90 μg/kg/hr brexanolone for the next 28 hours ($24^{th}$ to $52^{nd}$ hours); followed by administration of 60 μg/kg/hr brexanolone for the next four hours ($52^{nd}$ to $56^{th}$ hours), and followed by administration of 30 μg/kg/hr brexanolone for the last four hours ($56^{th}$ to $60^{th}$ hours) ("the 90 μs brexanolone dose regimen").

The 90 μg brexanolone dose regimen was proposed as the recommended dose regimen for postpartum depression because, by design, the efficacy of the 90 μs brexanolone dose regimen was demonstrated in 3 separate placebo-controlled studies and evaluated in a larger number of patients and over a wider range of postpartum depression severities than the 60 μg brexanolone dose regimen. The 90 μg brexanolone dose regimen did not appear to confer greater risk to safety than the 60 μg brexanolone dose regimen. Since the 90 μg brexanolone dose regimen was deemed to be effective for treatment of postpartum depression, it was not necessary to study higher doses of allopregnanolone.

Intravenous infusion of the 60 μg brexanolone dose regimen and the 90 μg brexanolone dose regimen are both associated with abrupt loss of consciousness, syncope and presyncope. Specifically, about 4% of patients exposed to brexanolone had abrupt loss of consciousness, syncope or presyncope. An abrupt loss of consciousness, syncope and presyncope can be dangerous to the patient (e.g., falls, drowning, etc.) and to the infant (e.g., drops, smothering).

OBJECTS AND SUMMARY OF THE INVENTION

It is an object of the invention to provide a treatment for postpartum depression.

It is also an object of the invention to provide a prophylaxis for postpartum depression.

It is another object of the invention to utilize ganaxolone's gamma-aminobutyric acid (GABA)-ergic mechanism of action to provide a therapeutic benefit in the prophylaxis and treatment of postpartum depression.

It is an additional object of the invention to provide a treatment for postpartum depression that is based on the patient's weight.

It is an additional object of the invention to provide a treatment for postpartum depression that does not require upward titration of the therapeutic agent during administration.

It is a further object of the invention to provide a treatment for postpartum depression that alleviates a symptom of postpartum depression, for example, as early as 4 to 8 hours after the start of the administration of a therapeutic agent.

It is a further object of the invention to provide a treatment for postpartum depression that has a lower risk of adverse effects (e.g., loss of consciousness) as compared to the 60 µg brexanolone dose regimen and the 90 µg brexanolone dose regimen.

It is a further object of the invention to provide a treatment for postpartum depression that has a better efficacy at 2 days after administration as compared to the 60 µg brexanolone dose regimen and the 90 µg brexanolone dose regimen.

It is a further object of the invention to provide a treatment for postpartum depression that has a better efficacy at 3 days after administration as compared to the 60 µg brexanolone dose regimen and the 90 µg brexanolone dose regimen.

It is a further object of the invention to provide a treatment for postpartum depression that has a better efficacy at 1 day after administration as compared to the 60 µg brexanolone dose regimen and the 90 µg brexanolone dose regimen.

It is a further object of the invention to provide a treatment for postpartum depression that has a better efficacy at 2, 3 and 11 days after administration as compared to the 60 µg brexanolone dose regimen and the 90 µg brexanolone dose regimen.

It is a further object of the invention to provide a treatment for postpartum depression that has a better efficacy at 34 days after administration as compared to the 60 µg brexanolone dose regimen and the 90 µg brexanolone dose regimen.

In furtherance of the above objects and others, the present invention is directed in part to a method of treating a female suffering from or at risk of developing postpartum depression comprising administering a therapeutically effective amount of ganaxolone to the female. Treatment may be initiated during third trimester of pregnancy or after the female gives birth (e.g., 4 weeks after female gives birth). The therapeutically effective amount of ganaxolone in the methods of present invention is preferably the amount of ganaxolone that compensates for the decline in a plasma level(s) of an endogenous neurosteroid(s) (e.g., allopregnanolone) and/or stabilizes a plasma level of an endogenous neurosteroid(s) in the female before and/or after childbirth and prevents and/or alleviates and/or reduces the severity of one or more symptom(s) of postpartum depression in the female (e.g., depressed mood, anxiety, insomnia, etc.). When the therapeutically effective amount, or a portion thereof, is administered intravenously the amount of ganaxolone administered and the rate of the intravenous administration is based on the female's weight, to ensure adequate exposure to ganaxolone. Thus, in the methods of the invention, ganaxolone is administered parenterally via a continuous intravenous infusion in an amount and at a rate which provides ganaxolone plasma concentration of from about 40 ng/ml to about 400 ng/ml for a time period of from about 6 hours to about 72 hours (e.g., about 8 hours, about 10 hours, about 12 hours, about 14 hours, about 16 hours, about 18 hours, about 20 hours, about 22 hours, about 24 hours, about 26 hours, about 28 hours, about 30 hours, about 32 hours, about 36 hours, about 38 hours, about 40 hours, about 42 hours, about 44 hours, about 46 hours, about 48 hours, about 50 hours, about 52 hours, about 54 hours, about 56 hours, about 58 hours, about 60 hours, about 62 hours, about 64 hours, about 66 hours, about 68 hours, or about 70 hours), and, in the preferred embodiments, maintains a ratio of plasma ganaxolone concentration (in ng/ml) to the dose of ganaxolone (in µg/kg/hr) in a range of from about 0.9:1 to about 1.2:1. For example, ganaxolone may be administered via the continuous intravenous infusion at a dose of about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr, for for a time period of from about 6 hours to about 72 hours. The invention encompasses administration of ganaxolone parenterally via the continuous infusion at a dose greater than about 150 µg/kg/hr and less than about 260 µg/kg/hr, for at least 4 to 8 hours (e.g., for a time period of from about 6 hours to about 72 hours) of the continuous infusion. The invention encompasses parenteral administration of ganaxolone via a continuous infusion started and maintained at a dose of about 86 µg/kg/hr, 150 µg/kg/hr, 155 µg/kg/hr, 160 µg/kg/hr, 170 µg/kg/hr, 180 µg/kg/hr, 190 µg/kg/hr, 200 µg/kg/hr, 210 µg/kg/hr, 220 µg/kg/hr, 240 µg/kg/hr, or 250 µg/kg/hr. In some embodiments, the dose is about 190 µg/kg/hr, 200 µg/kg/hr, 210 µg/kg/hr, or 220 µg/kg/hr and is administered, e.g., for a time period of form about 6 hours to about 72 hours (e.g., for about 6 hours, about 8 hours, about 12 hours, about 24 hours, about 48 hours, or about 60 hours). In certain embodiments, the dose may be increased up to about 300 µg/kg/hr, 350 µg/kg/hr or higher, to provide an improved response over a lower dose, the limiting factors being increased side effects from the higher dose. For example, if excessive somnolence is observed in the female, the dose may be decreased or the infusion may temporarily stopped or discontinued. In the preferred embodiments, administration of ganaxolone in these amounts and at these rates is sufficient to compensate for the decline in a plasma level(s) of an endogenous neurosteroid(s) (e.g., allopregnanolone) and/or stabilize a plasma level of an endogenous neurosteroid(s) and reduce the severity of one or more symptom(s) of postpartum depression in the female.

In the methods of the invention, parenteral administration of ganaxolone for a time period of from about 4 hour to about 72 hours to a female in need thereof provides an average plasma concentration of ganaxolone from about 40 ng/ml to about 400 ng/ml (e.g., 40 ng/ml to about 350 ng/ml) for the duration of the parenteral administration and compensates for the decline in a plasma level(s) of an endogenous neurosteroid(s) in the female and/or alleviate and/or reduces the severity of one or more symptom(s) of postpartum depression in the female, for example, as early as about 4 to 8 hours (e.g., about 6 hours) after the start of the administration. If excessive somnolence is observed in the female, the dose may be decreased or the infusion may temporarily stopped or discontinued. Thus, in certain embodiments, the upper limit of the plasma concentration provided by the intravenous infusion of ganaxolone in the methods of the invention may be limited by the side effect profile of the administration (e.g., somnolence), and may, e.g., be less than about 350 ng/ml, about 300 ng/ml, about 275 ng/ml, or about 260 ng/ml. In certain embodiments, an average plasma concentration of ganaxolone of about 45 ng/ml, about 55 ng/ml, about 65 ng/ml, about 75 ng/ml, about 85 ng/ml, about 95 ng/ml, about 100 ng/ml, about 125 ng/ml, about 150 ng/ml, about 175 ng/ml, about 200 ng/ml, about 250 ng/ml, or about 260 ng/ml, is provided and maintained for a time period of from about 2 hours to about 80 hours (e.g., 4 hours, 6 hours, 8 hours, 12 hours, 24 hours, 48 hours, or 60 hours) and alleviates and/or reduces the severity of one or more symptom(s) of postpartum depression in the female, for example, as early as about 4 to about 8 hours after the start of the administration.

In certain embodiments, parenteral administration of ganaxolone for a time period of from about 4 hour to about 72 hours to a group of females in need thereof provides a mean average plasma concentration of ganaxolone from about 90 ng/ml to about 400 ng/ml (e.g., from about 110 ng/ml to about 300 ng/ml) for the duration of the parenteral administration and compensates for the decline in a plasma level(s) of an endogenous neurosteroid(s) in the female and/or alleviate and/or reduces the severity of one or more symptom(s) of postpartum depression in the female, for example, as early as about 4 to 8 hours (e.g., about 6 hours) after the start of the administration. In certain embodiments, a mean average plasma concentration of ganaxolone of about 95 ng/ml, about 100 ng/ml, about 125 ng/ml, about 150 ng/ml, about 175 ng/ml, about 200 ng/ml, about 250 ng/ml, or about 260 ng/ml, is provided and maintained for a time period of from about 2 hours to about 80 hours (e.g., 4 hours, 6 hours, 8 hours, 12 hours, 24 hours, 48 hours, or 60 hours) and alleviates and/or reduces the severity of one or more symptom(s) of postpartum depression in the female, for example, as early as about 4 to about 8 hours after the start of the administration.

The invention is further directed to a method of treating a female suffering from or at risk of developing postpartum depression comprising administering intravenously to the female a formulation comprising ganaxolone and sulfobutylether-β-cyclodextrin in a weight ratio from about 1:50 to about 1:75 in an amount, at a rate and for a duration sufficient to alleviate and/or reduce the severity of one or more symptom(s) of postpartum depression in the female, for example, as early as about 4 to about 8 hours after the start of the administration. In some of these embodiments, the weight ratio ganaxolone and sulfobutylether-β-cyclodextrin is about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72. When ganaxolone is administered in a formulation comprising ganaxolone and sulfobutylether-β-cyclodextrin, the female suffering from or at risk of developing postpartum depression may receive from about 2 grams to about 65 grams sulfobutylether-β-cyclodextrin (e.g., from about 5 grams to about 63 grams, about 7 gram to about 60 grams, about 8 grams to about 57 grams, about 8 grams to about 56 grams, about 8 grams to about 55 grams, etc.) during the intravenous infusion.

In the methods of the invention, ganaxolone may be administered intravenously over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours in a single intravenous infusion. For example, ganaxolone may be administered via the single intravenous infusion over about 2 hours, about 3 hours, about 4 hours, about 6 hours, about 7 hours, about 8 hours, about 9 hours, about 10 hours about 12 hours, about 18 hours, about 20 hours, about 24 hours, about 36 hours, about 48 hours, about 54 hours, about 60 hours, or about 75 hours. In certain preferred embodiments, a single 2-hour intravenous infusion, 3-hour intravenous infusion, 4-hour intravenous infusion, 5-hour intravenous infusion, 6-hour intravenous infusion, 7-hour intravenous infusion, 8-hour intravenous infusion, 12-hour intravenous infusion, 18-hour intravenous infusion, 24-hour intravenous infusion, 48-hour intravenous infusion, or 60-hour intravenous infusion of ganaxolone in the amounts and at the rates disclosed herein alleviates or reduces the severity of one or more symptom(s) of postpartum depression, for example, as early as about 4 to about 8 hours after the start of the intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide a steady state plasma concentration (Css) of ganaxolone of from about 45 ng/ml to about 275 ng/ml, about 45 ng/ml to about 250 ng/ml, from about 50 ng/ml to about 200 ng/ml, from about 55 ng/ml to about 190 ng/ml, from about 60 ng/ml to about 190 ng/ml, from about 65 ng ml to about 185 ng/ml, from about 70 ng/ml to about 185 ng/ml, from about 75 ng/ml to about 180 ng/ml, from about 80 ng/ml to about 180 ng/ml, from about 85 ng/ml to about 180 ng/ml, from about 90 ng/ml to about 180 ng/ml, from about 95 ng/ml to about 180 ng/ml, from about 100 ng/ml to about 180 ng/ml, or from about 100 ng/ml to about 170 ng/ml; wherein the administration alleviates and/or prevents and/or reduces the severity of a symptom(s) of postpartum depression in the female (e.g., depressed mood, anxiety, insomnia, etc.), for example, as early as about 4 to about 8 hours after the start of the administration.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide an average ganaxolone plasma concentration of about 40.6 ng/ml to about 230 ng/ml for about 12 hours of the intravenous infusion; wherein the administration alleviates and/or prevents and/or reduces the severity of a symptom(s) of postpartum depression in the female (e.g., depressed mood, anxiety, insomnia, etc.), for example, at about 4 to about 8 hours after the start of the intravenous infusion. In some of these embodiments, administration of ganaxolone provides an average ganaxolone plasma concentration of about 91 ng/ml to about 275 ng/ml for the duration of intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide an average ganaxolone plasma concentration of about 56 ng/ml to about 254 ng/ml for 24 hours of the intravenous infusion; wherein the administration alleviates and/or prevents and/or reduces the severity of a symptom(s) of postpartum depression in the female (e.g., depressed mood, anxiety, insomnia, etc.), for example, at about 4 to about 8 hours after the start of the administration. In some of these embodiments, administration of ganaxolone provides an average ganaxolone plasma concentration of about 91 to about 275 ng/ml for the duration of the intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide an average ganaxolone plasma concentration of about 63 ng/ml to about 298 ng/ml for about 48 hours of the intravenous infusion; wherein the administration alleviates and/or prevents and/or reduces the severity of a symptom(s) of postpartum depression in the female (e.g., depressed mood, anxiety, insomnia, etc.), for example, at about 4 to about 8 hours after the start of the administration. In some of these embodiments, administration of ganaxolone provides an average ganaxolone plasma concentration of about 91 to about 275 ng/ml for the duration of the intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide an average ganaxolone plasma concentration of about 63 ng/ml to about 298 ng/ml for about 60 hours of the intravenous infusion; wherein the administration alleviates and/or prevents and/or reduces the severity of a symptom(s) of postpartum depression in the female (e.g., depressed mood, anxiety, insomnia, etc.), for example, at about 4 to about 8 hours after the start of the administration. In some of these embodiments, administration of ganaxolone provides an average ganaxolone plasma concentration of about 91 to about 275 ng/ml for the duration of the intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) in an amount and at a rate sufficient to provide an average ganaxolone plasma concentration of about 63 ng/ml to about 298 ng/ml at about 72 hours after the start of the intravenous infusion; wherein the administration alleviates and/or prevents and/or reduces the severity of a symptom(s) of postpartum depression in the female (e.g., depressed mood, anxiety, insomnia, etc.), for example, at about 4 to about 8 hours after the start of the intravenous infusion.

The invention is also directed in part to a method of treating postpartum depression comprising administering, within twelve months of childbirth (e.g., within 2 hours of childbirth), ganaxolone to a female suffering from postpartum depression or at risk of developing postpartum depression parenterally (e.g., via a single IV infusion) over a time period of from about 24 hours to about 60 hours in an amount and at a rate sufficient to provide a plasma concentration of ganaxolone of from about 45 ng/ml to about 250 ng/ml, from about 50 ng/ml to about 200 ng/ml, from about 55 ng/ml to about 190 ng/ml, from about 60 ng/ml to about 190 ng/ml, from about 65 ng ml to about 185 ng/ml, from about 70 ng/ml to about 185 ng/ml, from about 75 ng/ml to about 180 ng/ml, from about 80 ng/ml to about 180 ng/ml, from about 85 ng/ml to about 180 ng/ml, from about 90 ng/ml to about 180 ng/ml, from about 95 ng/ml to about 180 ng/ml, from about 100 ng/ml to about 180 ng/ml, or from about 100 ng/ml to about 170 ng/ml for about 2 to about 24 hours; wherein the administration alleviates and/or prevents and/or reduces the severity of a symptom(s) of postpartum depression in the female (e.g., depressed mood, anxiety, insomnia, etc.), for example, at about 4 to about 8 hours (e.g., about 6 hours) after the start of the intravenous infusion.

In certain embodiments, the method comprises administering ganaxolone parenterally (e.g., via a continuous IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) to a female in need thereof at a rate and in amount sufficient to provide ganaxolone $AUC_{12-24}$ of from about 1035 ng*hr/ml to about 3131 ng*hr/ml, and reduce the severity of a symptom(s) of postpartum depression in the female (e.g., depressed mood, anxiety, insomnia, etc.), for example, as early as about 4 to about 8 hours after the start of the administration.

In certain embodiments, the method comprises administering ganaxolone parenterally (e.g., via a continuous IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) to a female in need thereof at a rate and in amount sufficient to provide ganaxolone $AUC_{24-48}$ of from about 2301 ng*hr/ml to about 6958 ng*hr/ml, and reduce the severity of a symptom(s) of postpartum depression in the female (e.g., depressed mood, anxiety, insomnia, etc.), for example, as early as about 4 to about 8 hours after the start of the administration.

In certain embodiments, the method comprises administering ganaxolone parenterally (e.g., via a continuous IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) to a female in need thereof at a rate and in amount sufficient to provide ganaxolone $AUC_{12-48}$ of from about 3276 ng*hr/ml to about 9900 ng*hr/ml, and reduce the severity of a symptom(s) of postpartum depression in the female (e.g., depressed mood, anxiety, insomnia, etc.), for example, as early as about 4 to about 8 hours after the start of the administration.

If necessary, an intravenous bolus dose of ganaxolone may be given before the intravenous infusion of ganaxolone; and/or the intravenous infusion of ganaxolone may be followed by oral administration of ganaxolone (e.g., for about 7 days, 14 days, 21 days, 28 days or longer). The intravenous bolus dose of ganaxolone may be, e.g., from about 4 mg to about 35 mg. The oral daily dose of ganaxolone may be, e.g., from about 200 mg to about 2000 mg, from about 200 mg to about 1500 mg, from about 200 mg to about 1250 mg, or from about 200 mg to about 1000 mg.

The present invention is also directed in part to a method of treating postpartum depression comprising administering, within twelve months of childbirth (e.g., within 2 hours of childbirth), a bolus dose of ganaxolone intravenously in an amount sufficient to achieve a maximum plasma ganaxolone concentration (Cmax) of from about 200 ng/ml to about 400 ng/ml, from about 220 ng/ml to about 350 ng/ml or from about 250 ng/ml to about 300 ng/ml within 5 minutes of administration, and, immediately after the bolus dose (i.e., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose), administering ganaxolone intravenously over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, from about 54 hours to about 65 hours (e.g., over about 1 hour, 2 hours, 3 hours, 4 hours, 5 hours, 6 hours, 12 hours, 24 hours, 48 hours or 60 hours) via a single intravenous infusion in an amount and at a rate sufficient to maintain a steady state plasma concentration (Css) of ganaxolone of from about 70 ng/ml to about 280 ng/ml, about 70 ng/ml to about 250 ng/ml, from about 75 ng/ml to about 200 ng/ml, from about 80 ng/ml to about 175 ng/ml, from about 85 ng/ml to about 170 ng/ml, from about 85 ng/ml to about 170 ng/ml, from about 85 ng/ml to about 165 ng/ml, from about 85 ng/ml to about 160 ng/ml, from about 90 ng/ml to about 155 ng/ml, or from about 90 ng/ml to about 150 ng/ml. The intravenous bolus dose of ganaxolone may be, e.g., from about 4 mg to about 35 mg. The oral daily dose of ganaxolone may be, e.g., from about 200 mg to about 2000 mg, from about 200 mg to about 1500 mg, from about 200 mg to about 1250 mg, or from about 200 mg to about 1000 mg, and may be administered in divided doses.

The present invention is further directed in part to a method of treating postpartum depression comprising administering, within twelve months of childbirth (e.g., within 2 hours of childbirth), a bolus dose of ganaxolone intravenously preferably in an amount sufficient to achieve a maximum plasma ganaxolone concentration (Cmax) of from about 200 ng/ml to about 400 ng/ml, about 200 ng/ml to about 350 ng/ml, from about 220 ng/ml to about 320 ng/ml or from about 250 ng/ml to about 300 ng/ml within about 5 minutes of administration; and, immediately after the bolus dose (i.e., from about 1 second to about 1 hour, from about 1 second to about 45 minutes, from about 1 second to about 30 minutes, from about 1 second to about 15 minutes, from about 1 second to about 10 minutes, from about 1 second to about 5 minutes or from about 2 seconds to about 3 minutes after the bolus dose), administering ganaxolone intravenously over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., 60 hours) via an intravenous infusion in an amount and at a rate to maintain a steady state plasma concentration (Css) of ganaxolone of from about 70 ng/ml to about 280 ng/ml, about 70 ng/ml to about 260 ng/ml, about 70 ng/ml to about 240 ng/ml, about 70 ng/ml to about 180 ng/ml, from about 75 ng/ml to about 180 ng/ml, from about 80 ng/ml to about 175 ng/ml, from about 85 ng/ml to about 170 ng/ml, from about 85 ng/ml to about 170 ng/ml, from about 85 ng/ml to about 165 ng/ml, from about 85 ng/ml to about 160 ng/ml, from about 90 ng/ml to about 155 ng/ml, or from about 90 ng/ml to about 150 ng/ml; and, within 24 hours of the intravenous infusion, administering ganaxolone orally for a time period of from 2 days to about 6 months, from 2 days to about 5 months, from 3 days to about 4 months, from about 4 days to about 3 months, from about 5 days to about 2 months, from about 5 days to about 6 weeks, from about 6 days to about 5 weeks, or from about 7 days to about 4 weeks in an amount sufficient to maintain a steady state plasma concentration (Css) of ganaxolone of from about 50 ng/ml to about 160 ng/ml. The intravenous bolus dose of ganaxolone may be, e.g., from about 4 mg to about 35 mg. The oral daily dose of ganaxolone may be, e.g., from about 200 mg to about 2000 mg, from about 200 mg to about 1500 mg, from about 200 mg to about 1250 mg, or from about 200 mg to about 1000 mg, and may be administered in divided doses.

The present invention is also directed in part to a method of treating postpartum depression in a female comprising administering, within twelve months of childbirth (e.g., within 2 hours of childbirth), a therapeutically effective amount of ganaxolone to a female suffering from postpartum depression or at risk of developing postpartum depression parenterally (e.g., via IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., about 1 hour, 2 hours, 3 hours, 4 hours, 5 hours, 6 hours, 12 hours, 24 hours, 48 hours or 60 hours), at a mean rate of from about 3 mg/hr to about 40 mg/hr, from about 3 mg/hr to about 30 mg/hr, from about 3 mg/hr to about 25 mg/hr, from about 5 mg/hr to about 20 mg/hr, from about 7 mg/hr to about 18 mg/hr, from about 8 mg/hr to about 16 mg/hr, or from about 8 mg/hr to about 15 mg/hr, such that the female receives from about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr of ganaxolone, and a steady state plasma concentration (Css) of ganaxolone of from about 70 ng/ml to about 250 ng/ml, from about 75 ng/ml to about 225 ng/ml, from about 80 ng/ml to about 175 ng/ml, from about 85 ng/ml to about 170 ng/ml, from about 85 ng/ml to about 170 ng/ml, from about 85 ng/ml to about 165 ng/ml, from about 85 ng/ml to about 160 ng/ml, from about 90 ng/ml to about 155 ng/ml, or from about 90 ng/ml to about 150 ng/ml is provided in the female.

The present invention is also directed in part to a method of treating postpartum depression in a female comprising administering, within twelve months of childbirth (e.g., within 2 hours of childbirth), a therapeutically effective amount of ganaxolone to a female suffering from postpartum depression or at risk of developing postpartum depression parenterally (e.g., via IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours), wherein from about 70% to about 95% of the therapeutically effective amount is administered at a first constant rate (mg/hr) for the first 1 to 55 hours of administration (e.g., for the first 2 hours, 3 hours, 4 hours, 6 hours, 7 hours, 8 hours, 10 hours, 12 hours, 24 hours or 48 hours of administration) such that the female receives from about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr ganaxolone, and from about 5% to about 30% of the therapeutically effective amount is administered at a second constant rate (mg/hr) for the last 1 to 24 hours of administration (e.g., the last 12 hours of administration). The first constant rate and the second constant rate each can be, e.g., independently, from about 1 mg/hr to about 45 mg/hr, from about 1 mg/hr to about 40 mg/hr, from about 1 mg/hr to about 35 mg/hr, from about 1 mg/hr to about 30 mg/hr, from about 1 mg/hr to about 25 mg/hr, from about 1 mg/hr to about 20 mg/hr, from about 1.5 mg/hr to about 20 mg/hr, from about 1.5 mg/hr to about 19 mg/hr, from about 1.5 mg/hr to about 18 mg/hr, from about 2 mg/hr to about 18 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, from about 2 mg/hr to about 12 mg/hr. In some of the embodiments, the second constant rate is about half of the first constant rate. For example, the first constant rate can be from about 4 mg/hr to about 20 mg/hr, and the second constant rate can be, e.g., from about 2 mg/hr to about 10 mg/hr. The first constant rate can be about 4 mg/hr, and the second constant rate can be about 2 mg/hr. The first constant rate can also be about 8 mg/hr, and the second constant rate can be about 4 mg/hr. The first constant rate can also be about 12 mg/hr, and the second constant rate can be about 6 mg per hour.

The invention is further directed to a method of treating postpartum depression in a female comprising administering, within twelve months of childbirth (e.g., within 2 hours of childbirth), a therapeutically effective amount of ganaxolone to a female suffering from postpartum depression or at risk of developing postpartum depression parenterally (e.g., via IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours), wherein from about 1% to about 5% of the therapeutically effective amount is administered as a bolus dose at the beginning of the administration, from about 70% to about 95% of the therapeutically effective amount is administered, after the bolus dose, at a first constant rate during for the first 1 to 55 hours of administration (e.g., the first 2 hours, 3 hours, 4 hours, 5 hours, 6 hours, 7 hours, 8 hours, 12 hours, 24 hours, or 48 hours of administration), and from about 4% to about 25% of the therapeutically effective amount is administered at a second constant rate (mg/hr) during for the last 1 to 24 hours after administration (e.g., the last 12 hours of administration). The bolus dose can be, e.g., from about 6 mg to about 35 mg or from about 6 mg to about 30 mg of ganaxolone administered over 1 to 10 minutes. The first constant rate and the second constant rate can be, e.g., as outlined in the preceding paragraph.

The methods of the present invention may also comprise administering, preferably within twelve months of childbirth (e.g., within 2 hours of childbirth), from about 100 mg to about 140 mg of ganaxolone parenterally (e.g., intravenously) for a time period from about 1 hour to 8 hours (e.g., 2, 4, 5 or 6 hours) at a first constant rate of from about 1 mg/hr to about 45 mg/hr, from about 1 mg/hr to about 40 mg/hr, from about 1 mg/hr to about 35 mg/hr, from about 1 mg/hr to about 30 mg/hr, from about 1 mg/hr to about 25 mg/hr, from about 1 mg/hr to about 20 mg/hr, from about 1.5 mg/hr to about 20 mg/hr, from about 1.5 mg/hr to about 19 mg/hr, from about 1.5 mg/hr to about 18 mg/hr, from about 2 mg/hr to about 18 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, from about 2 mg/hr to about 12 mg/hr such that the female receives about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr ganaxolone, and then, at a time from about 6 hours to about 24 hours after the parenteral administration, administering orally daily from about 400 mg to about 2000 mg, from about 400 mg to about 1500 mg, from about 400 mg to about 1250 mg, or from about 400 mg to about 1000 mg of ganaxolone daily for a time period of from 2 days to about 6 months. For example, oral administration of ganaxolone may continue for a time period of from 2 days to about 5 months, from 3 days to about 4 months, from about 4 days to about 3 months, from about 5 days to about 2 months, from about 5 days to about 6 weeks, from about 6 days to about 5 weeks, or from about 7 days to about 4 weeks.

In certain embodiments, the method comprises administering ganaxolone parenterally (e.g., via IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 12 hours, 24 hours, 48 hours or 60 hours) to a female in need thereof (e.g., a female with baseline HAM-D score of from 11 to 50) at a rate and dose sufficient to provide ganaxolone $AUC_{0-72}$ of from about 2,000 ng*hr/ml to about 15,000 ng*hr/ml. The administration of ganaxolone at such rate and dose in certain preferred embodiments results in HAM-D score at the end of the treatment of 10 or less (e.g., 9, 8, 7, 6, 5, 4, 3, 2, 1, or 0). In some of these embodiments, the administration of ganaxolone results in a decrease in HAM-D of from 1 to 50% at 34 days after the beginning of administration.

Certain embodiments of the present invention are further directed to administering ganaxolone parenterally (e.g., via IV infusion) over about a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 7 hours, 8 hours, 10 hours, 12 hours, 24 hours, 48 hours, or 60 hours) at a rate and dose sufficient to improve mood for a time period that extends for about 34 days or more after administration.

Certain embodiments of the present invention are further directed to administering ganaxolone parenterally (e.g., via IV infusion) over about a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 7 hours, 8 hours, 10 hours, 12 hours, 24 hours, 48 hours, or 60 hours) at a rate and dose sufficient to reduce anxiety for a time period that extends for about 34 days or more after administration.

Certain embodiments of the present invention are further directed to administering ganaxolone parenterally (e.g., via IV infusion) over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 7 hours, 8 hours, 10 hours, 12 hours, 24 hours, 48 hours, or 60 hours) at a rate and dose sufficient to reduce insomnia for a time period that extends for about 34 days or more after administration.

Certain embodiments of the present invention are further directed to administering from about 150 mg to about 900 mg of ganaxolone parenterally over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 7 hours, 8 hours, 10 hours, 12 hours, 24 hours, 48 hours, or 60 hours) to a female at risk of developing or diagnosed with postpartum depression. For example, in certain embodiments, a dose of ganaxolone of about 216 mg, 432 mg or 660 mg may be administered parenterally to the female over about 60 hours at a rate of less than about 75 µg/kg/hr, from about 75 µg/kg/hr to about 250 µg/kg/hr, from about 80 µg/kg/hr to about 250 µg/kg/hr, from about 75 µg/kg/hr to about 240 µg/kg/hr, from about 75 µg/kg/hr to about 230 µg/kg/hr, from about 75 µg/kg/hr to about 220 µg/kg/hr, from about 75 µg/kg/hr to about 210 µg/kg/hr, from about 75 µg/kg/hr to about 200 µg/kg/hr, from about 75 µg/kg/hr to about 190 µg/kg/hr, from about 75 µg/kg/hr to about 185 µg/kg/hr, from about 75 µg/kg/hr to about 180 µg/kg/hr, from about 75 µg/kg/hr to about 170 µg/kg/hr, from about 75 µg/kg/hr to about 160 µg/kg/hr, from about 80 µg/kg/hr to about 160 µg/kg/hr, from about 80 µg/kg/hr to about 155 µg/kg/hr, from about 75 µg/kg/hr to about 115 µg/kg/hr, from about 90 µg/kg/hr to about 155 µg/kg/hr, from about 95 µg/kg/hr to about 155 µg/kg/hr, from about 100 µg/kg/hr to about 155 µg/kg/hr, from about 105 µg/kg/hr to about 155 µg/kg/hr, from about 110 µg/kg/hr to about 155 µg/kg/hr, from about 115 µg/kg/hr to about 155 µg/kg/hr, from about 120 µg/kg/hr to about 155 µg/kg/hr, or from about 120 µg/kg/hr to about 150 µg/kg/hr.

In the preferred embodiments of the invention, ganaxolone is administered intravenously without any titration steps at a first constant rate for the first 6 hours to 55 hours of the infusion (e.g., for about the first 48 hours of infusion), and a second constant rate for the last 6 hours to 24 hours of infusion (e.g., for about the last 12 hours of the infusion), wherein the first constant rate is 16 mg/hr or less, is greater than the second constant rate, and the infusion is at a dose of from about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr for from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 1 hour, 2 hours, 3 hours, 4 hours, 5 hours, 6 hours, 7 hours, 8 hours, 10 hours, 12 hours, 24 hours, 48 hours, or 60 hours). For example, in certain embodiments, ganaxolone is infused at a rate of about 4 mg/hr (16 ml/hr of ganaxolone 0.25 mg/ml solution) for the first about 48 hours and then at a rate of about 2 mg/hr for the next about 12 hours. In additional embodiments ganaxolone is infused at a rate of about 8 mg/hr (16 ml/hr of ganaxolone 0.5 mg/ml solution) for the first 48 hours and then at a rate of about 4 mg/hr for the next about 12 hours. In additional embodiments, ganaxolone is infused at a rate of about 12 mg/hr (24 ml/hr of ganaxolone 0.5 mg/ml solution) for 48 hours and then at a rate of about 6 mg/hr for the next about 12 hours. In additional embodiments, ganaxolone is infused at a rate that does not exceed about 16 mg/hr for the first about 12 hours then at a lower rate for the next about 12 hours. In all of these embodiments, the infusion may be stopped at about 60 hours (e.g., if one or more symptom(s) of postpartum depression is improved).

In certain embodiments, an initial bolus dose of 16 mg, or less, is given over 2-5 minutes prior to initiation of the ganaxolone intravenous infusion.

In certain embodiments, dosing may be initiated with ganaxolone infusion at a rate of about 20 mg/hr (40 ml/h of ganaxolone 0.5 mg/ml solution) at a dose of about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr for a time period of from about 6 hours to about 60 hours, followed by a dose of ganaxolone of from about 450 to about 2000 mg, from about 500 mg to about 1800 mg, from about 600 mg to about 1600 mg, from about 600 mg to about 1200 mg, from about 600 mg to about 1000 mg, from about 450 mg to about 1100 mg, from about 450 mg to about 1000 mg given orally in one or more divided doses (e.g., at dinner time for about 28 days). The oral dose may be followed by about a 3-day taper of progressively decreasing oral doses of ganaxolone.

In certain embodiments, the invention is directed to a method of treating postpartum depression, comprising administering a therapeutic dose of ganaxolone to a female within twelve months of childbirth parenterally in a manner which achieves a plasma concentration of ganaxolone of from about 45 ng/ml to about 300 ng/ml over a time period of from about 1 hour to about 72 hours, and wherein the administration alleviates or reduces severity of at least one symptom of postpartum depression at about 4 to about 8 hours after the start of the administration. The method may further comprise one or more of the following additional features:

administering ganaxolone via a single intravenous infusion over about 6 hours;

administering the therapeutic dose of ganaxolone to the female patient via a single intravenous infusion of ganaxolone followed by oral administration of ganaxolone;

administering the therapeutic dose of ganaxolone to the female patient via a single intravenous infusion of ganaxolone followed by oral administration of ganaxolone, wherein wherein said oral administration comprises orally administering from about 400 mg to about 2000 mg ganaxolone daily in one, two or three divided doses;

administering the therapeutic dose of ganaxolone to the female patient via a single intravenous infusion of ganaxolone followed by oral administration of ganaxolone, wherein a bolus dose of ganaxolone intravenously before the single intravenous infusion, the bolus dose comprising an amount of ganaxolone sufficient to provide ganaxolone $C_{max}$ of from about 200 ng/ml to about 400 ng/ml within 5 minutes of the bolus administration;

administering ganaxolone via a single intravenous infusion, and then administering ganaxolone orally daily for a time period of from about 2 days to about 6 months after the single intravenous infusion;

administering ganaxolone via a single intravenous infusion, wherein from about 150 mg to about 900 mg of ganaxolone is administered during the single intravenous infusion;

administering ganaxolone via a single intravenous infusion, wherein from about 70% to about 95% of the therapeutic dose administered during the single intravenous infusion is administered at a first constant rate, and from about 5% to about 30% of the therapeutic dose is administered at a second constant rate;

administering ganaxolone via a single intravenous infusion, wherein from about 70% to about 95% of the therapeutic dose administered during the single intravenous infusion is administered at a first constant rate, and from about 5% to about 30% of the therapeutic dose is administered at a second constant rate, wherein the first constant rate is greater than the second constant rate, and the first constant rate is from about 1.5 mg/hr to about 35 mg/hr;

said administration provides a plasma concentration of ganaxolone of from about 100 ng/ml to about 400 ng/ml and alleviates or reduces severity of at least one symptom of postpartum depression at about 6 hours after the start of the administration;

said administration further provides an $AUC_{12-48}$ of from about 3276 ng*hr/ml to about 9900 ng*hr/ml.

In certain embodiments, ganaxolone is administered to a female parenterally over a time period of from about 2 hours to about 72 hours in an amount and at a rate sufficient to provide an $AUC_{0-48}$ of from about 1000 ng*hr/ml to about 8500 ng*hr/ml, wherein at least one symptom of postpartum depression is alleviated or reduced at a time occurring at about 4 to about 8 hours after the start of the administration. The method may further comprise one or more of the following additional features:

the administration provides an $AUC_{24-48}$ of from about 2301 ng*hr/ml to about 6958 ng*hr/ml;

ganaxolone is administered via a single intravenous infusion over about 6 hours.

ganaxolone is administered via a single intravenous infusion over about 6 hours, and the intravenous infusion is followed by oral administration of ganaxolone;

ganaxolone is administered via a single intravenous infusion over about 6 hours, and the intravenous infusion is followed by oral administration of ganaxolone, wherein said oral administration comprises oral administration of from about 400 mg to about 2000 mg ganaxolone daily in one, two or three divided doses;

ganaxolone is administered via a single intravenous infusion over about 6 hours, and the intravenous infusion is followed by oral administration of ganaxolone, further comprising administering a bolus dose of ganaxolone intravenously before the single intravenous infusion, the bolus dose comprising an amount of ganaxolone sufficient to provide ganaxolone Cmax of from about 200 ng/ml to about 400 ng/ml;

ganaxolone is administered via a single intravenous infusion, wherein from about 150 mg to about 900 mg of ganaxolone is administered during the single intravenous infusion.

The invention is also directed to a method of treating postpartum depression, comprising administering a therapeutic dose of ganaxolone to a female within twelve months of childbirth in a manner which provides a plasma concentration of ganaxolone of from 30 ng/ml to about 300 ng/ml over a 24-hour period, and a first peak in the plasma concentration of ganaxolone and a second peak during said 24-hour period, wherein the first peak is provided by an intravenous infusion of ganaxolone, and the second peak is provided by administration of an oral dose of ganaxolone, and the administration of the therapeutic dose alleviates or reduces severity at least one symptom of postpartum depression at about 4 to about 6 hours after the start of the administration of the therapeutic dose. The intravenous infusion may, e.g., be over about 6 hours. The intravenous infusion may also be over about 8 hours, about 10 hours, about 12 hours, about 14 hours, about 18 hours, about 24 hours, about 36 hours, about 48 hour, about 60 hours, or about 72 hours.

In certain embodiments, the invention is directed to a method of treating postpartum depression, comprising administering a therapeutic dose of ganaxolone to a female suffering from or at risk of developing postpartum depression within twelve months of childbirth parenterally in a manner which achieves a steady state plasma concentration (Css) of ganaxolone of from about 120 ng/ml to about 250 ng/ml over a time period of from about 1 hour to 72 hours, and wherein the administration alleviates or reduces the severity of at least one symptom of postpartum depression. The method may further comprise one or more of the following additional features:

ganaxolone is administered via a single intravenous infusion over about 2 hours, about 4 hours, about 6 hours, about 8 hours, about 10 hours, about 12 hours, about 24 hours, about 48 hours, or about 60 hours;

the intravenous infusion is followed by oral administration of ganaxolone;

the intravenous infusion is followed by oral administration of ganaxolone, wherein said oral administration comprises oral administration from about 400 mg to about 2000 mg ganaxolone daily in one, two or three divided doses;

the intravenous infusion is followed by oral administration of ganaxolone, wherein said oral administration comprises oral administration from about 400 mg to about 1200 mg ganaxolone daily for 1 week, 2 weeks, 3 weeks, 4 weeks, 6 weeks, 8 weeks, 12 weeks, 16 weeks, or 24 weeks;

the intravenous infusion is followed by oral administration of ganaxolone, wherein said oral administration comprises oral administration from about 400 mg to about 1000 mg ganaxolone daily for a time period of up to 12 months;

the intravenous infusion is followed by oral administration of ganaxolone, wherein said oral administration comprises oral administration of ganaxolone in a capsule or an oral suspension.

The invention is further directed to a method of treating a female suffering from or at risk of developing postpartum depression comprising administering ganaxolone to the female parenterally over 60 hours via a single 60-hour intravenous infusion in an amount and at a rate to provide a steady state plasma concentration (Css) of ganaxolone of from about 45 ng/ml to about 250 ng/ml, from about 50 ng/ml to about 200 ng/ml, from about 55 ng/ml to about 190 ng/ml, from about 60 ng/ml to about 190 ng/ml, from about 65 ng ml to about 185 ng/ml, from about 70 ng/ml to about 185 ng/ml, from about 75 ng/ml to about 180 ng/ml, from about 80 ng/ml to about 180 ng/ml, from about 85 ng/ml to about 180 ng/ml, from about 90 ng/ml to about 180 ng/ml, from about 95 ng/ml to about 180 ng/ml, from about 100 ng/ml to about 180 ng/ml, or from about 100 ng/ml to about 170 ng/ml; wherein the administration alleviates or reduces the severity of at least one symptom of postpartum depression. The method may further comprise one or more of the following additional features:

administering a bolus dose of ganaxolone intravenously before the infusion, the bolus dose comprising an amount of ganaxolone sufficient to provide ganaxolone Cmax of from about 200 ng/ml to about 400 ng/ml, from about 220 ng/ml to about 320 ng/ml or from about 250 ng/ml to about 300 ng/ml within 5 minutes of the bolus administration;

administering, after the single 60-hour infusion, ganaxolone orally for a time period of from 2 days to about 6 months, from 2 days to about 5 months, from 3 days to about 4 months, from about 4 days to about 3 months, from about 5 days to about 2 months, from about 5 days to about 6 weeks, from about 6 days to about 5 weeks, or from about 7 days to about 4 weeks in an amount sufficient to maintain Css concentration of ganaxolone of from about 120 ng/ml to about 260 ng/ml;

administering from about 150 mg to about 900 mg of ganaxolone in a single 60-hour infusion;

administering from about 150 mg to about 900 mg of ganaxolone in a single 60-hour infusion, wherein from about 70% to about 95% of the ganaxolone dose is administered at a first constant rate (mg/hr) for the first 48 hours of the single 60-hour infusion, and from about 5% to about 30% of the ganaxolone dose is administered at a second constant rate (mg/hr) for the last 12 hours of single 60-hour infusion;

administering a total ganaxolone dose comprising from about 150 mg to about 900 mg of ganaxolone in a single 60-hour infusion, wherein from about 70% to about 95% of the total ganaxolone dose is administered at a first constant rate (mg/hr) for the first 48 hours of the single 60-hour infusion, and from about 5% to about 30% of the total ganaxolone dose is administered at a second constant rate (mg/hr) for the last 12 hours of single 60-hour infusion, and the first constant rate is greater than the second constant rate, at a dose of about 86 µg/kg/hr to about 260 µg/kg/hr, about 100 µg/kg/hr to about 260 µg/kg/hr, about 110 µg/kg/hr to about 260 µg/kg/hr, about 120 µg/kg/hr to about 260 µg/kg/hr, about 130 µg/kg/hr to about 260 µg/kg/hr, about 140 µg/kg/hr to about 260 µg/kg/hr, about 150 µg/kg/hr to about 260 µg/kg/hr, about 155 µg/kg/hr to about µg/kg/hr; about 155 µg/kg/hr to about 240 µg/kg/hr; about 155 µg/kg/hr to about 240 µg/kg/hr; about 160 µg/kg/hr to about 230 µg/kg/hr; about 160 µg/kg/hr to about 220 µg/kg/hr, or about 160 µg/kg/hr to about 210 µg/kg/hr;

administering a total ganaxolone dose comprising from about 150 mg to about 900 mg of ganaxolone in a single 60-hour infusion, wherein from about 70% to about 95% of the total ganaxolone dose is administered at a first constant rate (mg/hr) for the first 48 hours of the single 60-hour infusion, and from about 5% to about 30% of the total ganaxolone dose is administered at a second constant rate (mg/hr) for the last 12 hours of single 60-hour infusion, and the first constant rate is greater than the second constant rate, wherein the first constant rate is from about 1.5 mg/hr to about 35 mg/hr, from about 1.5 mg/hr to about 30 mg/hr, from about 1.5 mg/hr to about 25 mg/hr, from about 2 mg/hr to about 20 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, or from about 2 mg/hr to about 12 mg/hr;

administering a total ganaxolone dose comprising from about 150 mg to about 900 mg of ganaxolone in a single 60-hour infusion, wherein from about 70% to about 95% of the total ganaxolone dose is administered at a first constant rate (mg/hr) for the first 48 hours of the single 60-hour infusion, and from about 5% to about 30% of the total ganaxolone dose is administered at a second constant rate (mg/hr) for the last 12 hours of single 60-hour infusion, wherein the first constant rate is greater than the second constant rate;

administering a total ganaxolone dose comprising from about 150 mg to about 900 mg of ganaxolone in a single 60-hour infusion, wherein from about 70% to about 95% of the total ganaxolone dose is administered at a first constant rate (mg/hr) for the first 48 hours of the single 60-hour infusion, and from about 5% to about 30% of the total ganaxolone dose is administered at a second constant rate (mg/hr) for the last 12 hours of single 60-hour infusion, wherein the second constant rate is about half of the first constant rate;

administering from about 1% to about 5% of the total ganaxolone dose as a bolus dose; from about 70% to about 95% of the total ganaxolone dose after the bolus dose at a first constant rate during for the first 48 hours of administration; and from about 4% to about 25% of the total ganaxolone dose at a second constant rate during for the last 12 hours of administration;

administration of ganaxolone results in HAM-D score of 10 or less at the end of the infusion;

administration of ganaxolone is not associated with an abrupt loss of consciousness;

the infusion provides ganaxolone $AUC_{0-72}$ of from about 2,000 ng*hr/ml to about 15,000 ng*hr/ml.

The invention is also directed to a method of reducing HAM-D score in a female suffering from or at risk of developing postpartum depression comprising administering parenterally via a single intravenous infusion an amount of ganaxolone that compensates for the decline in a plasma level(s) of an endogenous neurosteroid(s) during twelve months of childbirth, wherein the endogenous neurosteroid is allopregnanolone, and the female has HAM-D score of from 11 to 50 prior to the intravenous infusion, and HAM-D score of 10 or less after the single 60-hour infusion. The method may further comprise one or more of the following additional features:

216 mg, 432 mg or 660 mg of ganaxolone is administered parenterally to the female over 60 hours at a rate of from about 75 µg/kg/hr to about 250 µg/kg/hr;

ganaxolone is administered at a rate of from about 75 µg/kg/hr to about 185 µg/kg/hr;

the administration provides a steady state plasma concentration (Css) of ganaxolone of from about 45 ng/ml to about 250 ng/ml.

The invention is also directed to a method of treating postpartum depression, comprising administering a therapeutic dose of ganaxolone to a female suffering from or at risk of developing postpartum depression within twelve months of childbirth parenterally via an intravenous infusion in a manner which maintains a steady state plasma concentration (Css) of ganaxolone of from about 45 ng/ml to about 250 ng/ml for the first 12 to 55 hours of the infusion, and a steady state plasma concentration (Css) of ganaxolone of from about 100 ng/ml to about 250 ng/ml for the last 6 to 24 hours of the infusion. The method may further comprise one or more of the following additional features:

the infusion is a 60-hour infusion, and the steady state plasma concentration (Css) of ganaxolone about 45 ng/ml to about 250 ng/ml is maintained for the first 45 to 50 hours of the infusion, and the steady state plasma concentration (Css)

of ganaxolone from about 100 ng/ml to about 250 ng/ml is maintained for the last 10 to 15 hours of the infusion;

the intravenous infusion is administered during third trimester of pregnancy;

the intravenous infusion is administered after childbirth.

The invention is further directed to a method of treating postpartum depression, comprising administering a therapeutic dose of ganaxolone to a female suffering from or at risk of developing postpartum depression within twelve months of childbirth in a manner which provides a plasma concentration of ganaxolone of from 105 ng/ml to about 300 ng/ml over a 24-hour period, and from two to four peaks in the plasma concentration of ganaxolone during said 24-hour period. The method may further comprise one or more of the following additional features:

the administration provides three peaks in the plasma concentration of ganaxolone;

the administration provides three peaks in the plasma concentration of ganaxolone, wherein the first peak is provided by an intravenous infusion and/or bolus dose of ganaxolone, the second peak is provided by administration of an oral dose of ganaxolone, and the third peak is provided by a further oral dose of ganaxolone;

the intravenous infusion is at a rate of from about 1.5 mg/hr to about 35 mg/hr, from about 1.5 mg/hr to about 30 mg/hr, from about 1.5 mg/hr to about 25 mg/hr, from about 2 mg/hr to about 20 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, or from about 2 mg/hr to about 12 mg/hr, and at a dose of from about 86 μg/kg/hr to about 260 μg/kg/hr, about 100 μg/kg/hr to about 260 μg/kg/hr, about 110 μg/kg/hr to about 260 μg/kg/hr, about 120 μg/kg/hr to about 260 μg/kg/hr, about 130 μg/kg/hr to about 260 μg/kg/hr, about 140 μg/kg/hr to about 260 μg/kg/hr, about 150 μg/kg/hr to about 260 μg/kg/hr, about 155 μg/kg/hr to about μg/kg/hr; about 155 μg/kg/hr to about 240 μg/kg/hr; about 155 μg/kg/hr to about 240 μg/kg/hr; about 160 μg/kg/hr to about 230 μg/kg/hr; about 160 μg/kg/hr to about 220 μg/kg/hr, or about 160 μg/kg/hr to about 210 μg/kg/hr;

the bolus dose is from about 4 mg to about 35 mg;

the oral dose and the further oral dose is each independently from about 200 mg to about 1800 mg, from about 200 mg to about 1700 mg, from about 200 mg to about 1600 mg, from about 300 mg to about 1500 mg, from about 400 mg to about 1400 mg, or from about 450 to about 1300 mg;

the further oral dose is higher than the oral dose;

the second peak and the third peak are each independently from about 150 ng/ml to about 300 ng/ml, from about 160 ng/ml to about 280 ng/ml, or from about 160 ng/ml to about 250 ng/ml; and the second peak and the third peak are from about 2 hours to about 12 hours, from about 2 hours to about 10 hours, from about 2 hours to about 8 hours, from about 2 hours to about 6 hours, from about 2 hours to about 5 hours, or from about 2 hours to about 4 hours apart from each other;

the first and the second peak are from about 2 hours to about 12 hours, from about 2 hours to about 10 hours, from about 2 hours to about 8 hours, from about 2 hours to about 6 hours, from about 2 hours to about 5 hours, or from about 2 hours to about 4 hours apart from each other;

the first peak is at about 2 seconds to about 12 hours, is at about 2 seconds to about 10 hours, about 2 seconds to about 8 hours, about 2 seconds to about 6 hours, or about 2 seconds to about 6 hours from the beginning of the administration;

the second peak is at about 4 hours to about 20 hours, about 4 hours to about 16 hours, about 4 hours to about 12 hours, about 4 hours to about 10 hours, about 4 hours to about 8 hours, at about 4 hours to about 7 hours from the beginning of the administration;

the third peak is at about 5 hours to about 22 hours, about 5 hours to about 20 hours, about 5 hours to about 18 hours, about 4 hours to about 16 hours, about 4 hours to about 14 hours, at about 4 hours to about 12 hours from the beginning of the administration;

the administration provides two peaks in the plasma concentration of ganaxolone;

the first peak is provided by an intravenous infusion or bolus dose of ganaxolone, and the second peak is provided by administration of an oral dose of ganaxolone;

the intravenous infusion is at a rate of from about 1.5 mg/hr to about 35 mg/hr, from about 1.5 mg/hr to about 30 mg/hr, from about 1.5 mg/hr to about 25 mg/hr, from about 2 mg/hr to about 20 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, or from about 2 mg/hr to about 12 mg/hr;

the bolus dose is from about 4 mg to about 35 mg;

the oral dose is from about 200 mg to about 1800 mg, from about 200 mg to about 1700 mg, from about 200 mg to about 1600 mg, from about 300 mg to about 1500 mg, from about 400 mg to about 1400 mg, or from about 450 to about 1300 mg;

the first and the second peak are from about 2 hours to about 20 hours, from about 2 hours to about 18 hours, from about 2 hours to about 16 hours, from about 2 hours to about 14 hours, from about 2 hours to about 12 hours, or from about 2 hours to about 10 hours apart from each other.

The invention is further directed to a method of reducing an HAM-D score in a female suffering from or at risk of developing postpartum depression comprising administering parenterally, over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (via a single (about) 1-hour intravenous infusion, 2-hour intravenous infusion, 3-hour intravenous infusion, 4-hour intravenous infusion, 5-hour intravenous infusion, 6-hour intravenous infusion, 7-hour intravenous infusion, 8-hour intravenous infusion, 10-hour intravenous infusion, 12-hour intravenous infusion, 24-hour intravenous infusion, 48-hour intravenous infusion, or 60-hour intravenous infusion), an amount of ganaxolone that compensates for the decline in a plasma level(s) of an endogenous neurosteroid(s) and/or stabilizes a plasma level of an endogenous neurosteroid(s) to the female within about twelve months of childbirth (e.g., within 2 hours of childbirth), the female having HAM-D score of from about 11 to about 50 prior to the single intravenous infusion, and an HAM-D score at the end of the intravenous infusion of 10 or less (e.g., 9, 8, 7, 6, 5, 4, 3, 2, 1, or 0). In these embodiments, from about 150 mg to about 900 mg of ganaxolone may be administered to the female. For example, about 216 mg, about 432 mg or about 660 mg of ganaxolone may be administered parenterally to the female over 60 hours at a rate of less than about 75 μg/kg/hr, from about 75 μg/kg/hr to about 250 μg/kg/hr, from about 80 μg/kg/hr to about 250 μg/kg/hr, from about 75 μg/kg/hr to about 240 µg/kg/hr, from about 75 µg/kg/hr to about 230 µg/kg/hr, from about 75 µg/kg/hr to about 220 µg/kg/hr, from about 75 µg/kg/hr to about 210 µg/kg/hr, from about 75 µg/kg/hr to about 200 µg/kg/hr, from about 75 µg/kg/hr to about 190 µg/kg/hr, from about 75 µg/kg/hr to about 185 µg/kg/hr, from about 75 µg/kg/hr to about 180 µg/kg/hr, from about 75 µg/kg/hr to about 170 µg/kg/hr, from about 75 µg/kg/hr to about 160 µg/kg/hr, from about 80 µg/kg/hr to about 160 µg/kg/hr, from about 80 µg/kg/hr to about 155 µg/kg/hr, from about 75 µg/kg/hr to about 115 µg/kg/hr, from about 90 µg/kg/hr to about 155 µg/kg/hr, from about 95 µg/kg/hr to about 155 µg/kg/hr, from about 100 µg/kg/hr to about 155 µg/kg/hr, from about 105 µg/kg/hr to about 155 µg/kg/hr, from about 110 µg/kg/hr to about 155 µg/kg/hr, from about 115 µg/kg/hr to about 155 µg/kg/hr, from about 120 µg/kg/hr to about 155 µg/kg/hr, or from about 120 µg/kg/hr to about 150 µg/kg/hr.

The invention is further directed to a method of reducing an HAM-D score in a female suffering from or at risk of developing postpartum depression comprising administering parenterally, over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (via a single (about) 4-hour, 5-hour, 6-hour, 8-hour, 10-hour, 12-hour, 24-hour, 48-hour, or 60-hour intravenous infusion), an amount of ganaxolone that compensates for the decline in a plasma level(s) of an endogenous neurosteroid(s) and/or stabilizes a plasma level of an endogenous neurosteroid(s) to a female within about twelve months of childbirth (e.g., within 2 hours of childbirth), the female having a baseline HAM-D score of from 11 to 50, and an HAM-D score at the end of the treatment of about 10 or less (e.g., 10, 9, 8, 7, 6, 5, 4, 3, 2, 1, or 0), the administration providing a steady state plasma concentration (Css) of ganaxolone of from about 45 ng/ml to about 250 ng/ml, from about 50 ng/ml to about 200 ng/ml, from about 55 ng/ml to about 190 ng/ml, from about 60 ng/ml to about 190 ng/ml, from about 65 ng ml to about 185 ng/ml, from about 70 ng/ml to about 185 ng/ml, from about 75 ng/ml to about 180 ng/ml, from about 80 ng/ml to about 180 ng/ml, from about 85 ng/ml to about 180 ng/ml, from about 90 ng/ml to about 180 ng/ml, from about 95 ng/ml to about 180 ng/ml, from about 100 ng/ml to about 180 ng/ml, or from about 100 ng/ml to about 170 ng/ml.

In addition, the invention is directed to a method of reducing an HAM-D score in a female suffering from or at risk of developing postpartum depression comprising administering parenterally, over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (via a single (about) 4-hour, 5-hour, 6-hour, 8-hour, 10-hour, 12-hour, 24-hour, 48-hour, or 60-hour intravenous infusion), an amount of ganaxolone that compensates for the decline in a plasma level(s) of an endogenous neurosteroid(s) and/or stabilizes a plasma level of an endogenous neurosteroid(s) to a female within twelve months of childbirth (e.g., within 2 hours of childbirth), the female having a baseline HAM-D score of from about 11 to about 50, and an HAM-D score at the end of the treatment of about 10 or less (e.g., 10, 9, 8, 7, 6, 5, 4, 3, 2, 1, or 0), wherein from about 70% to about 95% of the amount is administered at a first constant rate (mg/hr) for the first about 1 to 55 hours of administration (e.g., about the first 48 hours of administration), and from about 5% to about 30% of the therapeutically effective amount is administered at a second constant rate (mg/hr) for the last 1 to 24 hours of administration (e.g., about the last 12 hours of administration). The first constant rate and the second constant rate each could, e.g., independently be from about 1 mg/hr to about 45 mg/hr, from about 1 mg/hr to about 40 mg/hr, from about 1 mg/hr to about 35 mg/hr, from about 1 mg/hr to about 30 mg/hr, from about 1 mg/hr to about 25 mg/hr, from about 1 mg/hr to about 20 mg/hr, from about 1.5 mg/hr to about 20 mg/hr, from about 1.5 mg/hr to about 19 mg/hr, from about 1.5 mg/hr to about 18 mg/hr, from about 2 mg/hr to about 18 mg/hr, from about 2 mg/hr to about 17 mg/hr, from about 2 mg/hr to about 16 mg/hr, from about 2 mg/hr to about 14 mg/hr, from about 2 mg/hr to about 13 mg/hr, from about 2 mg/hr to about 12 mg/hr. In some of the embodiments, the second constant rate is about half of the first constant rate.

The invention is also directed to a method of treating postpartum depression, comprising administering a therapeutic dose of ganaxolone to a female suffering from or at risk of developing postpartum depression within twelve months of childbirth in a manner which provides and maintains a plasma concentration of ganaxolone of greater than about 150 ng/mL for about the first 2 hours to 80 hours of administration. In some of these embodiments, the administration maintains plasma concentration of ganaxolone of greater than about 150 ng/mL for at least about the first 2 hours to 70 hours, the first 2 hours to 60 hours, 2 hours to 50 hours, 2 hours to 48 hours, 3 hours to 48 hours, 4 hours to 48 hours, 5 hours to 48 hours, 6 hours to 48 hours, 7 hours to 48 hours, 8 hours to 48 hours, or 9 hours to 48 hours of administration; and/or provides $AUC_{12-48}$ of from about 3276 ng*hr/mL to about 9900 ng*hr/mL. The administration may comprise (i) an intravenous infusion and/or bolus dose of ganaxolone, followed by (ii) oral administration of ganaxolone once, twice or three times a day. The oral administration comprises administering from about 400 mg to about 1800 mg of ganaxolone a day. In some of these embodiments, the oral daily dose of ganaxolone is administered in two divided dose about 2, 3, 4, 5, or 6 hours apart (e.g., the two divided doses may be administered within 6 hours of bedtime).

The invention is further directed to a method of treating postpartum depression, comprising administering a therapeutic dose of ganaxolone to a female suffering from or at risk of developing postpartum depression within twelve months of childbirth, wherein the female has HAM-D score of 25 or less, and ganaxolone is administered orally from one to four times a day. Generally, from about 200 mg to about 1000 mg of ganaxolone is administered orally per day (e.g., 900 mg per day).

In some embodiments, the parenteral administration of ganaxolone (e.g., intravenous administration) for postpartum depression does not exceed about 24 hours, about 18 hours, about 16 hours, about 14 hours, about 12 hours, about 10 hours, about 8 hours, or about 7 hours, and provides efficacy at about 4 hours to about 8 hours (e.g., about 6 hours).

In some embodiments, the parenteral administration of ganaxolone (e.g., intravenous administration) for postpartum depression does not exceed about 8 hours, and provides efficacy at about 4 hours to about 8 hours (e.g., about 6 hours).

In some embodiments, the parenteral administration of ganaxolone (e.g., intravenous administration) for postpartum depression does not exceed about 6 hours, and provides efficacy at about 4 hours to about 8 hours (e.g., about 6 hours).

In some embodiments, the parenteral administration of ganaxolone (e.g., intravenous administration) for postpartum depression is for about 48 or about 60 hours, is at a dose greater than 140 μg/kg/hr, and provides efficacy at about 4 hours to about 8 hours (e.g., about 6 hours).

The methods of the invention may further comprise a step of monitoring female suffering from or at risk of developing postpartum depression for sedative effects during the intravenous infusion, e.g., every 30 minutes, hour, 2 hours, 3 hours, 4 hours, 5 hours, 6 hours, etc., and decreasing the dose if signs of excessive sedation appear.

The invention is further directed to ganaxolone for use in a single 2-hour intravenous infusion, 3-hour intravenous infusion, 4-hour intravenous infusion, 5-hour intravenous infusion, 6-hour intravenous infusion, 7-hour intravenous infusion, 8-hour intravenous infusion, 12-hour intravenous infusion, 24-hour intravenous infusion, 48-hour intravenous infusion, or 60-hour intravenous infusion for the treatment of post-partum depression. In the preferred embodiments, the single infusion is sufficient to reduce or alleviate a symptom of postpartum depression in, as early as about 4 to about 8 hours after the start of the intravenous infusion.

In the preferred embodiments, administration of ganaxolone in accordance with the methods disclosed herein is not associated with abrupt loss of consciousness.

The invention is also directed to an IV bag comprising an effective amount of ganaxolone to provide plasma concentration of ganaxolone of from about 105 ng/ml to about 400 ng/ml over a time period of from about 1 hour to about 60 hours and sulfobutylether-β-cyclodextrin, wherein ganaxolone and sulfobutylether-β-cyclodextrin are in a weight ratio from about 1:50 to about 1:75. In some of these embodiments, the weight ratio ganaxolone and sulfobutylether-β-cyclodextrin is about 1:51, about 1:52, about 1:53, about 1:54, about 1:55, about 1:56, about 1:57, about 1:58, about 1:59, about 1:60, about 1:61, about 1:62, about 1:63, about 1:64, about 1:65, about 1:66, about 1:67, about 1:68, about 1:69, about 1:70, about 1:71, or about 1:72. In some embodiments, the IV bag comprises from about 60 mg to about 500 mg ganaxolone and about 2 grams to about 65 grams sulfobutylether-β-cyclodextrin (e.g., from about 5 grams to about 63 grams, about 7 gram to about 60 grams, about 8 grams to about 57 grams, about 8 grams to about 56 grams, about 8 grams to about 55 grams, etc.).

Definitions

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." The use of the term "about" with respect to doses and amounts of ganaxolone indicates that values slightly outside the cited values, i.e., plus or minus 0.1% to 20%. The use of the term "about" with respect to time periods of administration means for the purposes of the present invention to comprise 2 hours before and 2 hours after that time period. For example, a time period of "about 6 hours" encompasses a time period of 4 hours and a time period of 8 hours.

An "active agent" is any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e. optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The term "endogenous neurosteroid" means a steroid produced within the brain and capable of modulating neuronal excitability by interaction with neuronal membrane receptors and ion channels, principally GABA-A receptors, and includes, e.g., pregnane neurosteroids (e.g., allopregnanolone, allotetrahydrodeoxycorticosterone, etc.), androstane neurosteroids (e.g., androstanediol, etiocholanone, etc.), and sulfated neurosteroids (e.g., pregnanolone sulfate, dehydroepiandrosterone sulfate (DHEAS)).

The term "childbirth" includes a live birth, stillbirth and miscarriage.

The term "pregnenolone neurosteroid" means an endogenous or exogenous steroid capable of modulating neuronal excitability by interaction with neuronal membrane receptors and ion channels, principally GABA-A receptors, and encompasses, e.g., endogenous neurosteroids and synthetic neurosteroids synthesized or derived from pregnenolone in vitro and in vivo.

The terms "serum" and "plasma" as disclosed herein may be used interchangeably.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of."

A "bolus dose" is a relatively large dose of medication administered in a short period, for example within 1 to 30 minutes.

The term "AUC" means area under the curve. It represents the total drug exposure across time. $AUC_{12-24}$ is area under the curve for the time period from 12 hours to 24 hours. $AUC_{24-48}$ is area under the curve for the time period from 24 hours to 48 hours. $AUC_{12-48}$ is area under the curve for the time period from 12 hours to 48 hours.

The term "$C_{max}$" is the concentration of ganaxolone in the plasma at the point of maximum concentration.

The term "$C_{ss}$" means steady-state plasma concentration of ganaxolone, e.g., a substantially constant concentration of ganaxolone maintained by intravenous infusion of ganaxolone. The term $C_{ss}$ is different from and not synonymous with the term $C_{max}$.

The term "ganaxolone" means 3α-hydroxy-3β-methyl-5α-pregnan-20-one.

The term "infusion" administration is a non-oral administration, typically intravenous, though other non-oral routes such as epidural administration are included in some embodiments. Infusion administration occurs over a longer period than a bolus administration, for example for a time period of from about 2 hours to about 80 hours.

The term "IV bag" means a glass bottle or plastic bag that is filled a solution, suspension or emulsion containing ganaxolone. The IV bag may have a tubing connected to it, with a hollow needle at the end of the tubing.

The term "patient" or "subject" means a female in need of medical treatment for or at risk of developing postpartum depression. Medical treatment includes treatment of an existing condition, such as a disorder. In certain embodiments treatment also includes prophylactic or preventative treatment.

"Pharmaceutical compositions" are compositions comprising at least one active agent, such as a compound or salt, solvate, or hydrate of ganaxolone, and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a seizure disorder.

"Povidone" also known as polyvidone and polyvinylpyrrolidone (PVP) is a water soluble polymer made from the monomer, N-vinylpyrrolidone. Plasdone C-12 and C-17 are pharmaceutical grade homopolymers of N-vinylpyrrolidone. Plasdone C-12 has a K value of 10-2-13.8 and nominal molecular weight of 4000 d. Plasdone C-17 has a K-value of 15.5-17.5 and nominal molecular weight of 10,000 d.

"Sterilize" means to inactivate substantially all biological contaminates in a sample, formulation, or product. A 1-million fold reduction in the bioburden is also considered "sterilized" for most pharmaceutical applications.

The term "remission" is defined as a Hamilton Rating Scale for Depression (HAM-D) total score of 7 or lower.

A "therapeutically effective amount" or "effective amount" is that amount of ganaxolone to alleviate and/or prevent and/or reduce the severity of a symptom(s) of postpartum depression. The term "therapeutically effective amount" includes, for example, a prophylactically effective amount. An "effective amount" of ganaxolone is an amount needed to achieve a desired pharmacologic effect or therapeutic improvement without undue adverse side effects. The effective amount of ganaxolone will be selected by those skilled in the art depending on the particular patient and the disease. It is understood that "an effective amount" or "a therapeutically effective amount" can vary from subject to subject, due to variation in metabolism of ganaxolone, age, weight, general condition of the subject, the condition being treated, the severity of the condition being treated, and the judgment of the prescribing physician.

"Treat" or "treatment" refers to any treatment of a disorder or disease, such as inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

Unless otherwise specified, efficacy and an improvement in efficacy for the purposes of the present invention are based on a decrease in HAM-D score, based on "PP" (per-protocol analysis).

"Titration" means a gradual increase in dose at the beginning of the dosing interval. For the purposes of the present invention, "titration" does not encompass a bolus dose.

"HAM-D" means 17-item Hamilton Rating Scale for Depression.

"HAM-D response" means a 50%, or greater, reduction from baseline in HAM-D total score.

"HAM-D remission" means achieving HAM-D total score of ≤7.

As used herein, "hr" or "h" means hour.

As used herein, "µg/kg/hr" means microgram per kilogram per hour.

The "60 µg dose brexanolone regimen" means administration of 30 µg/kg/hr brexanolone for the first 4 hours, followed by administration of 60 µg/kg/hr brexanolone for the next 52 hours ($5^{th}$ to $56^{th}$ hours); followed by administration of 30 µg/kg/hr brexanolone for the next four hours ($56^{th}$ to $60^{th}$ hours) of the 60-hour brexanolone intravenous infusion.

The "90 µg dose brexanolone regimen" means administration of a dose of 30 µg/kg/hr brexanolone for the first 4 hours, followed by administration of 60 µg/kg/hr brexanolone for the next 20 hours, followed by administration of 90 µg/kg/hr brexanolone for the next 28 hours ($24'$ to $52^{nd}$ hours); followed by administration of 60 µg/kg/hr brexanolone for the next four hours ($52^{nd}$ to $56^{th}$ hours), and followed by administration of 30 µg/kg/hr brexanolone for the next four hours ($56^{th}$ to $60^{th}$ hours) of the 60-hour brexanolone intravenous infusion.

"PPD" means postpartum depression.

"GNX140 IV" means intravenous administration of 140 µg/kg/hr ganaxolone.

"BRX60" means the "60 µg dose brexanolone regimen."

"SAGE-217" means zuranolone, an orally bioavailable pregnane neurosteroid.

"Robin Study" means a study of 30 mg oral daily administration of zuranolone for 28 days.

"Hummingbird" means a Phase 3, randomized, double-blind trial evaluating the efficacy and safety of brexanolone in the treatment of moderate and severe postpartum depression compared to placebo, as assessed by the Hamilton Rating Scale for Depression (HAM-D).

"Magnolia study," unless otherwise specified, means administration of ganaxolone in accordance with the regimen of Cohort 1, or Cohort 2, or Cohort 3, or Cohort 4, or Cohort 5, or Cohort 6.

"C1" means Cohort 1 of *Magnolia* study.
"C2" means Cohort 2 of *Magnolia* study.
"C3" means Cohort 3 of *Magnolia* study.
"C4" means Cohort 4 of *Magnolia* study.
"C5" means Cohort 5 of *Magnolia* study.
"C6" means Cohort 6 of *Magnolia* study.
"PLC" and "PLX" means placebo.

"mITT" means an intention-to-treat (ITT) analysis of the results of an experiment. mITT is based on the initial treatment assignment and not on the treatment eventually received. mITT set consists of all subjects in the Safety Set who had at least 1 post-randomization efficacy assessment. mITT analysis requires subjects to be included even if they did not fully adhere to the protocol. Subjects who strayed from the protocol (for instance, by not adhering to the prescribed intervention, or by being withdrawn from active treatment) are kept in the analysis. mITT analysis provides information about the potential effects of treatment policy rather than on the potential effects of specific treatment.

"Per Protocol" or "PP" means per-protocol analysis. PP set consists of all subjects in the mITT set who do not have protocol deviations that may affect key efficacy endpoints. This protocol analysis is restricted only to the subjects who fulfill the protocol in the terms of the eligibility, adherence to the intervention, and outcome assessment. A per-protocol analysis provides information about an effect of the specific treatment.

An "average plasma concentration" as used herein means an average of plasma concentrations in an individual subject.

A "mean plasma concentration" means a mean of plasma concentrations obtained from a population of subjects.

A "mean average plasma concentration" means a mean of average plasma concentrations obtained from a population of subjects.

DETAILED DESCRIPTION

Figure 1:
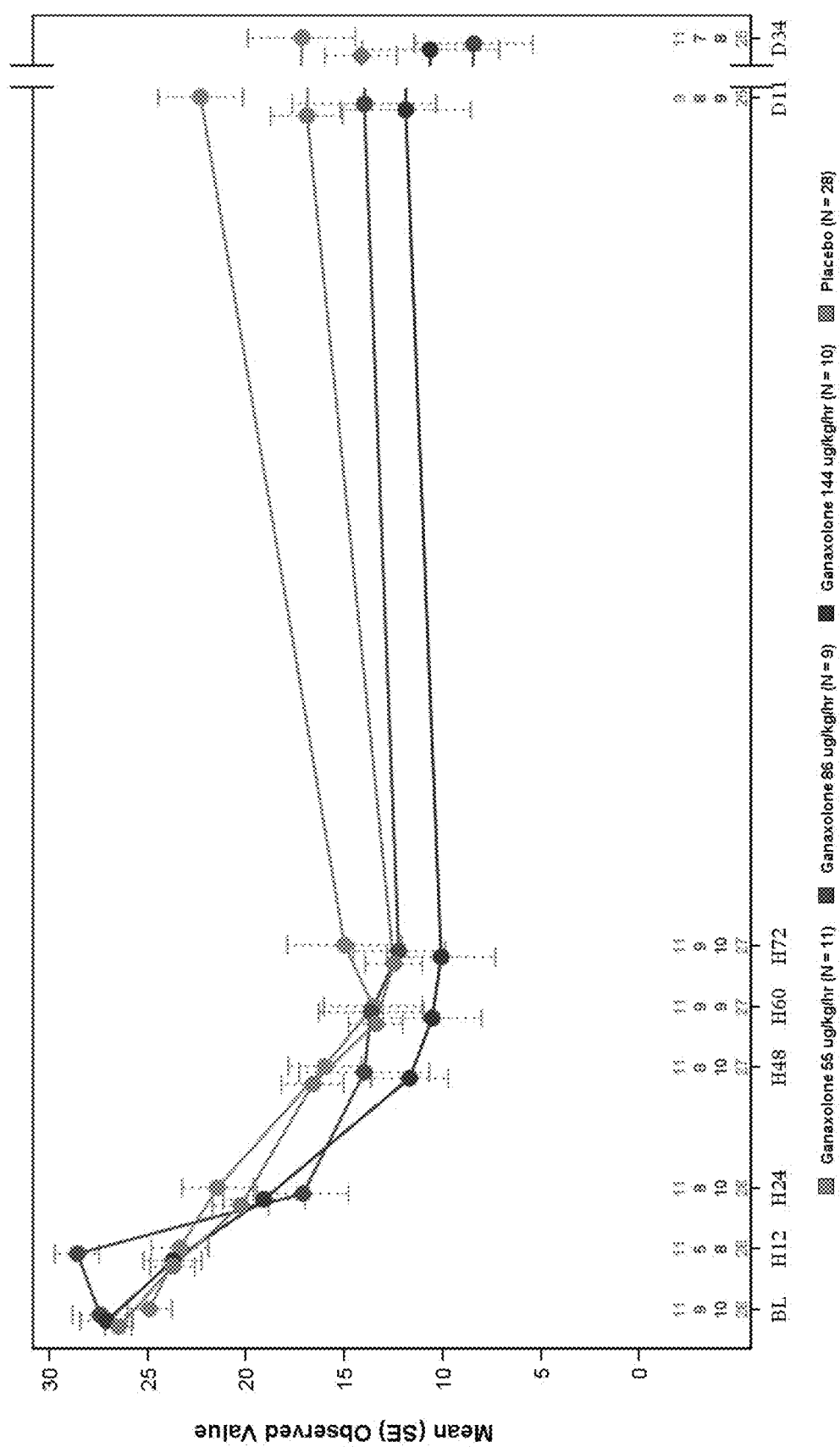
FIG. 1 depicts mean HAM-D17 total score by weight-adjusted dose for Cohorts 1-3.
Figure 2:
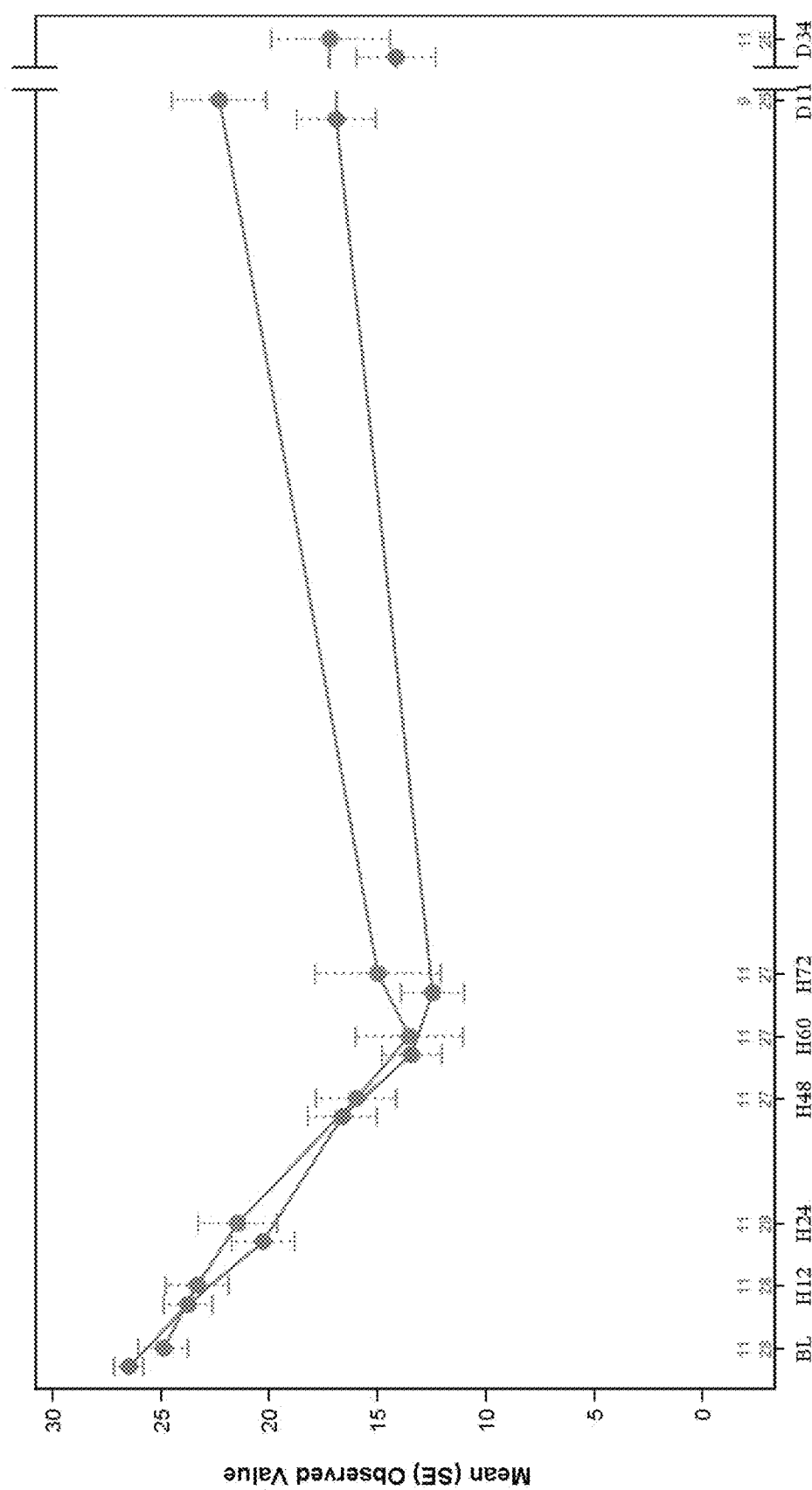
FIG. 2 depicts mean HAM-D17 total score by weight-adjusted dose for Cohorts 1-3, low weight-adjusted dose group (55 µg/kg/hr).
Figure 3:
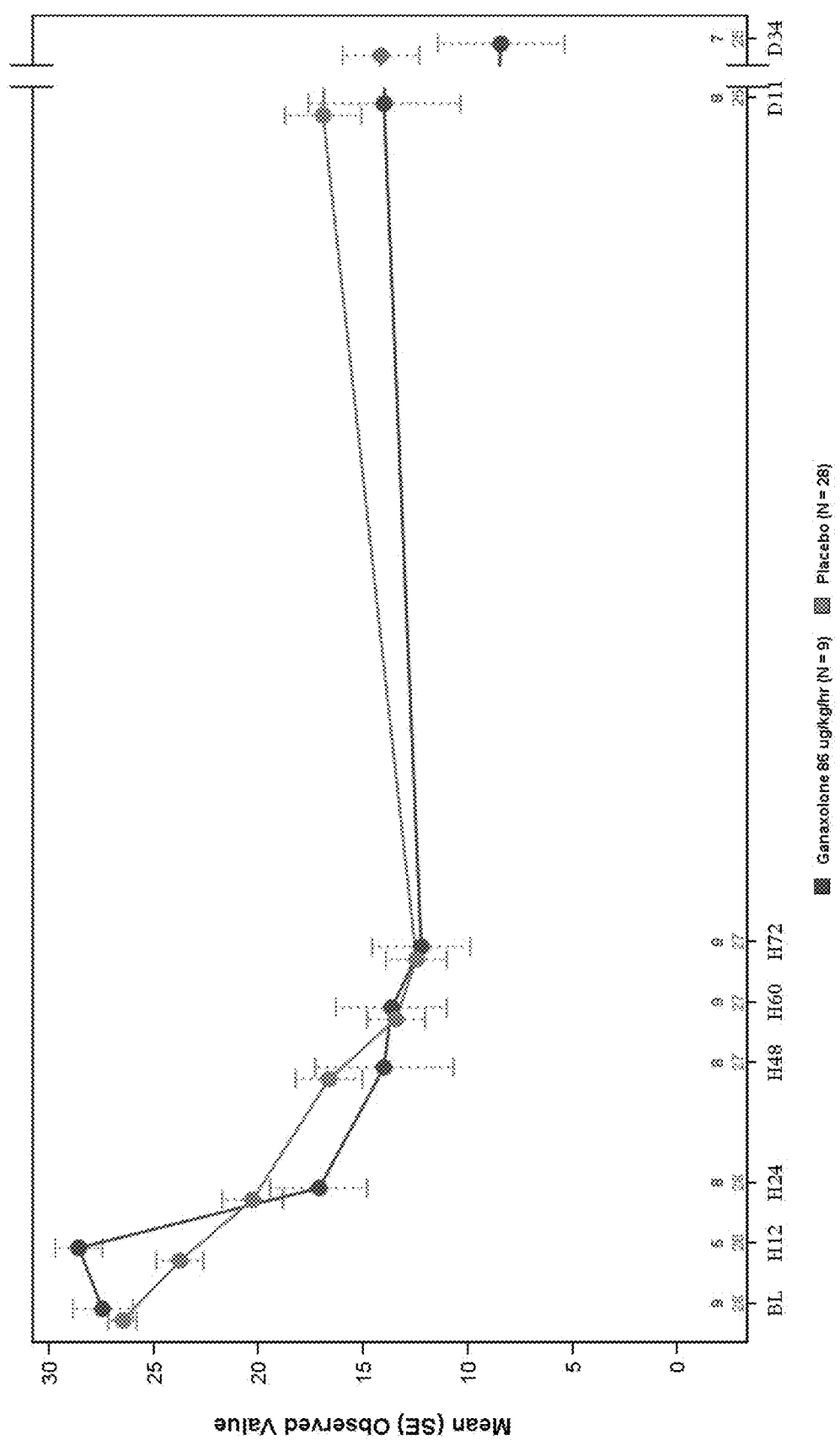
FIG. 3 depicts mean HAM-D17 total score by weight-adjusted dose for Cohorts 1-3, medium weight-adjusted dose group (86 µg/kg/hr).
Figure 4:
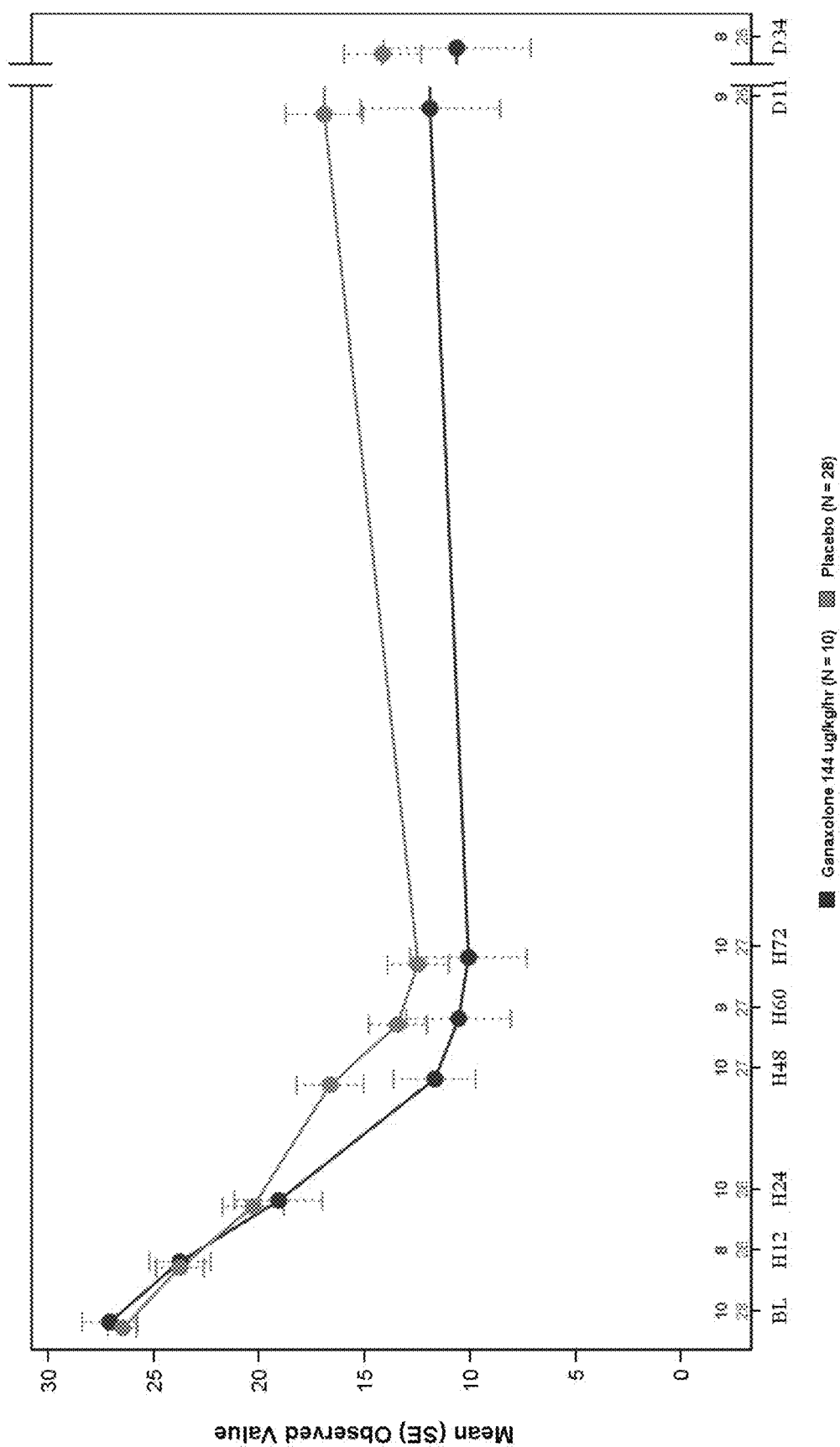
FIG. 4 depicts mean HAM-D17 total score by weight-adjusted dose for Cohorts 1-3, high weight-adjusted dose group (144 µg/kg/hr).
Figure 5:
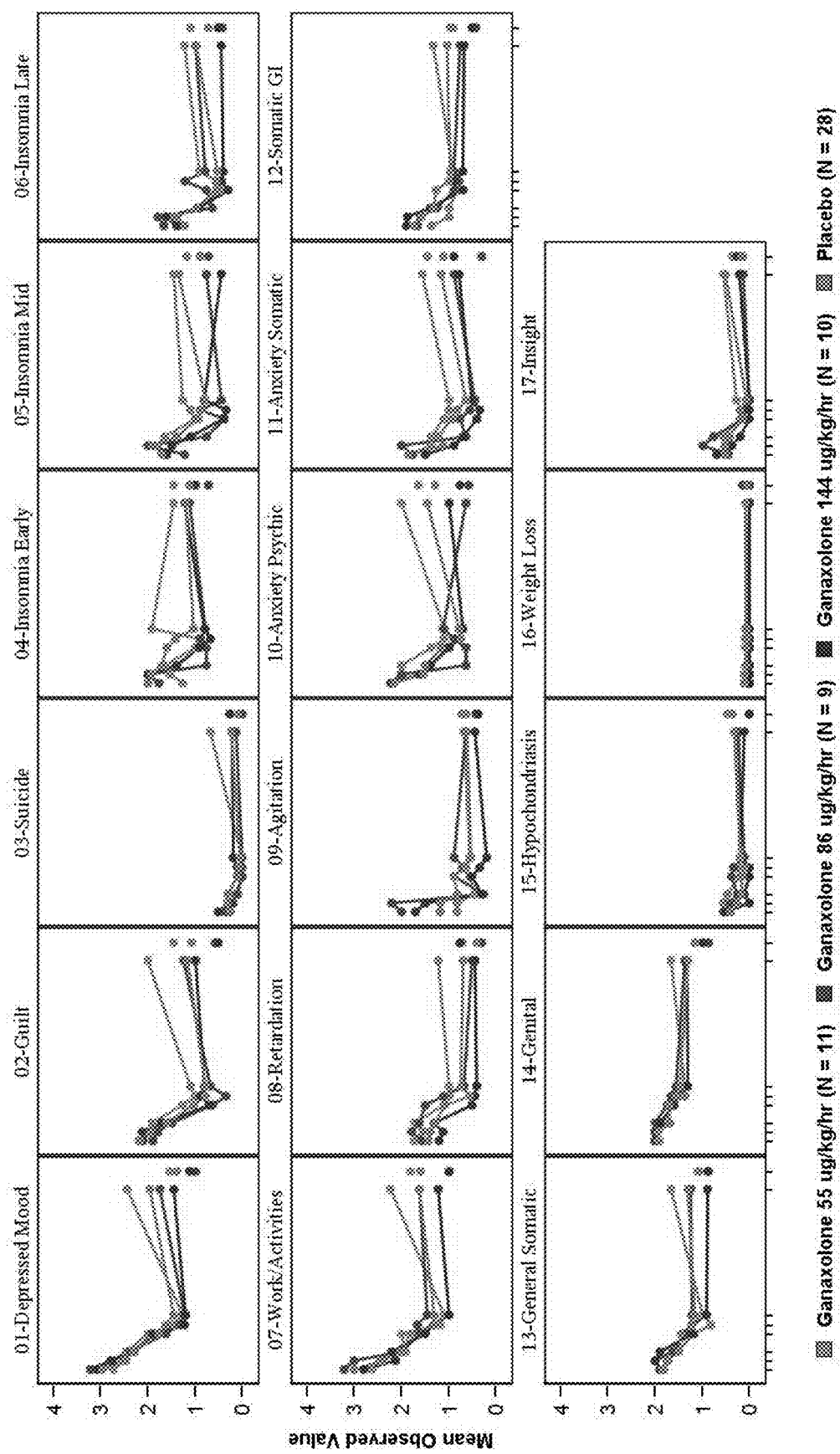
FIG. 5 depicts mean HAM-D17 individual items by weight-adjusted dose for Cohorts 1-3.
Figure 6:
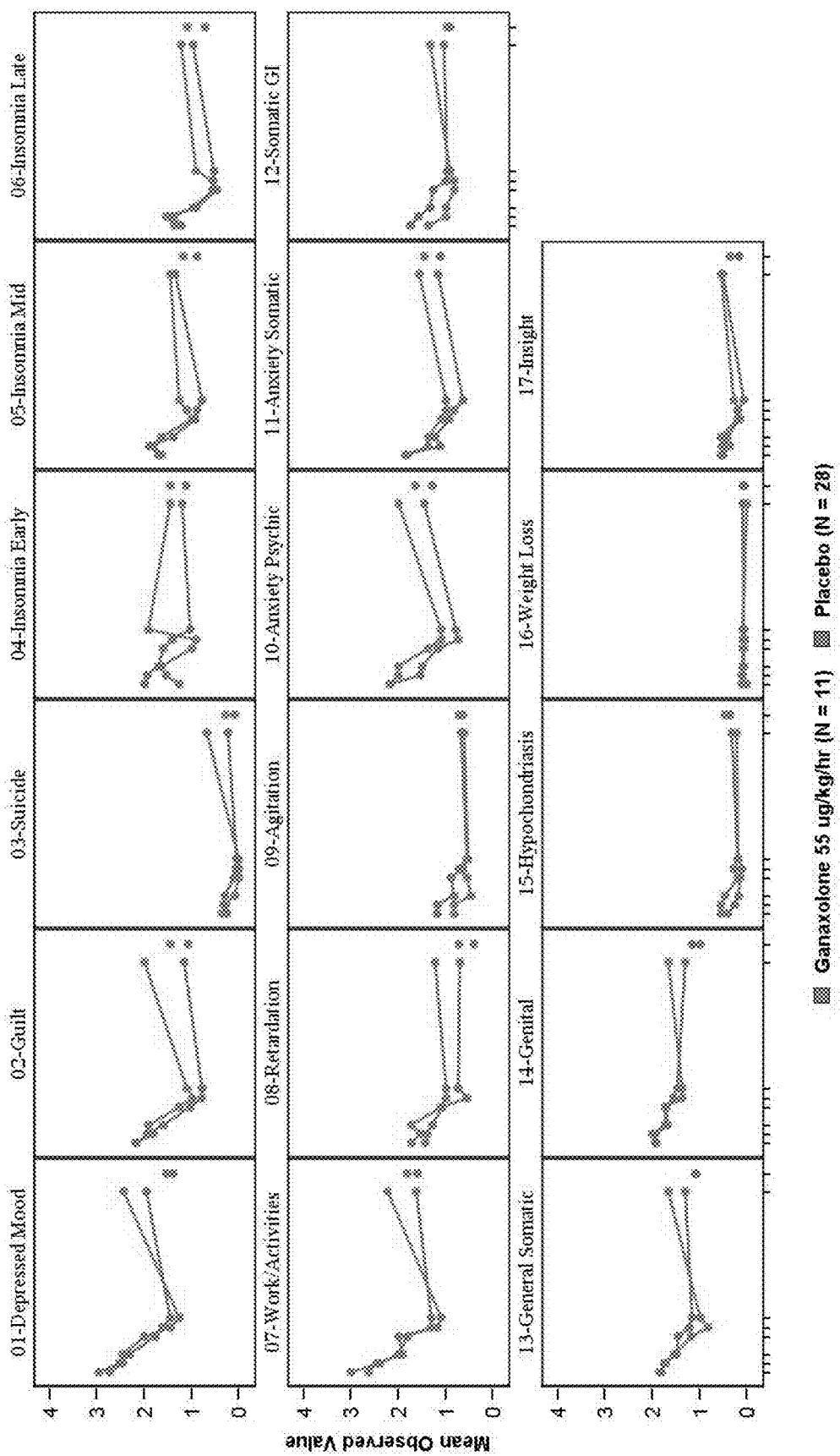
FIG. 6 depicts mean HAM-D17 individual items by weight-adjusted dose, for Cohorts 1-3, low weight-adjusted dose group (55 µg/kg/hr).
Figure 7:
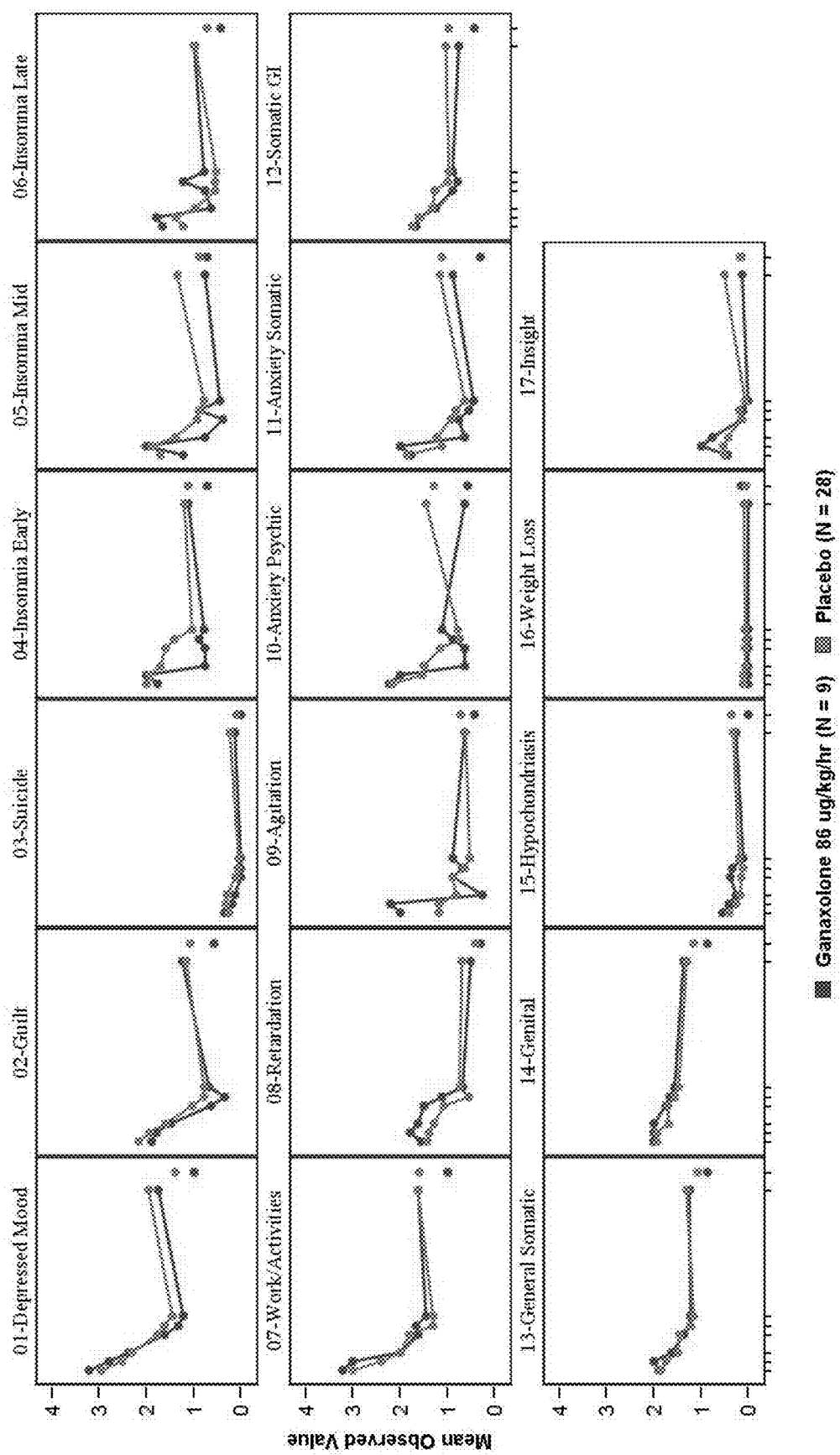
FIG. 7 depicts mean HAM-D17 individual items by weight-adjusted dose for Cohorts 1-3, medium weight-adjusted dose group (86 µg/kg/hr).
Figure 8:
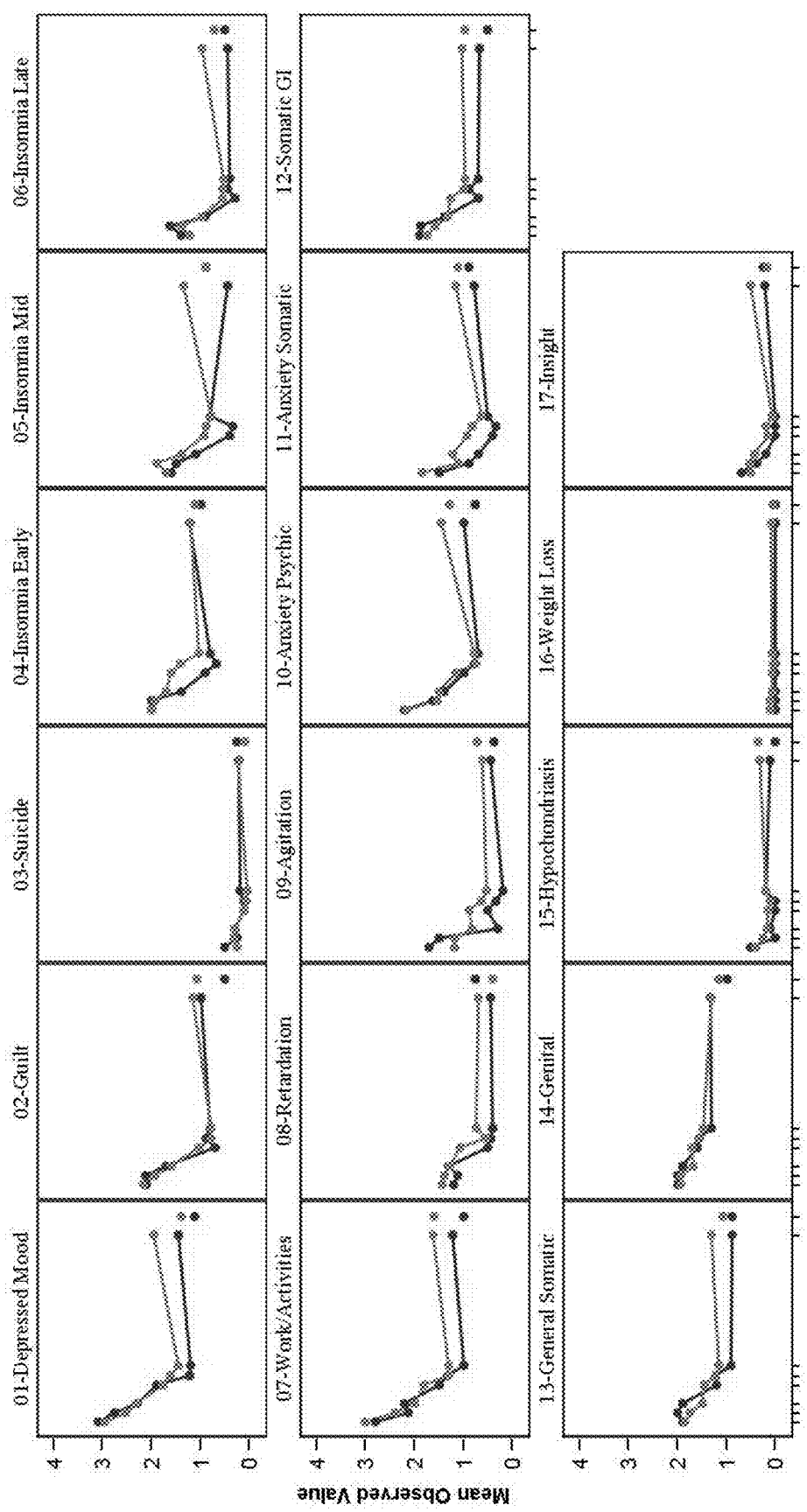
FIG. 8 depicts mean HAM-D17 individual items by weight-adjusted dose for Cohorts 1-3, high weight-adjusted dose group (144 µg/kg/hr).
Figure 9:
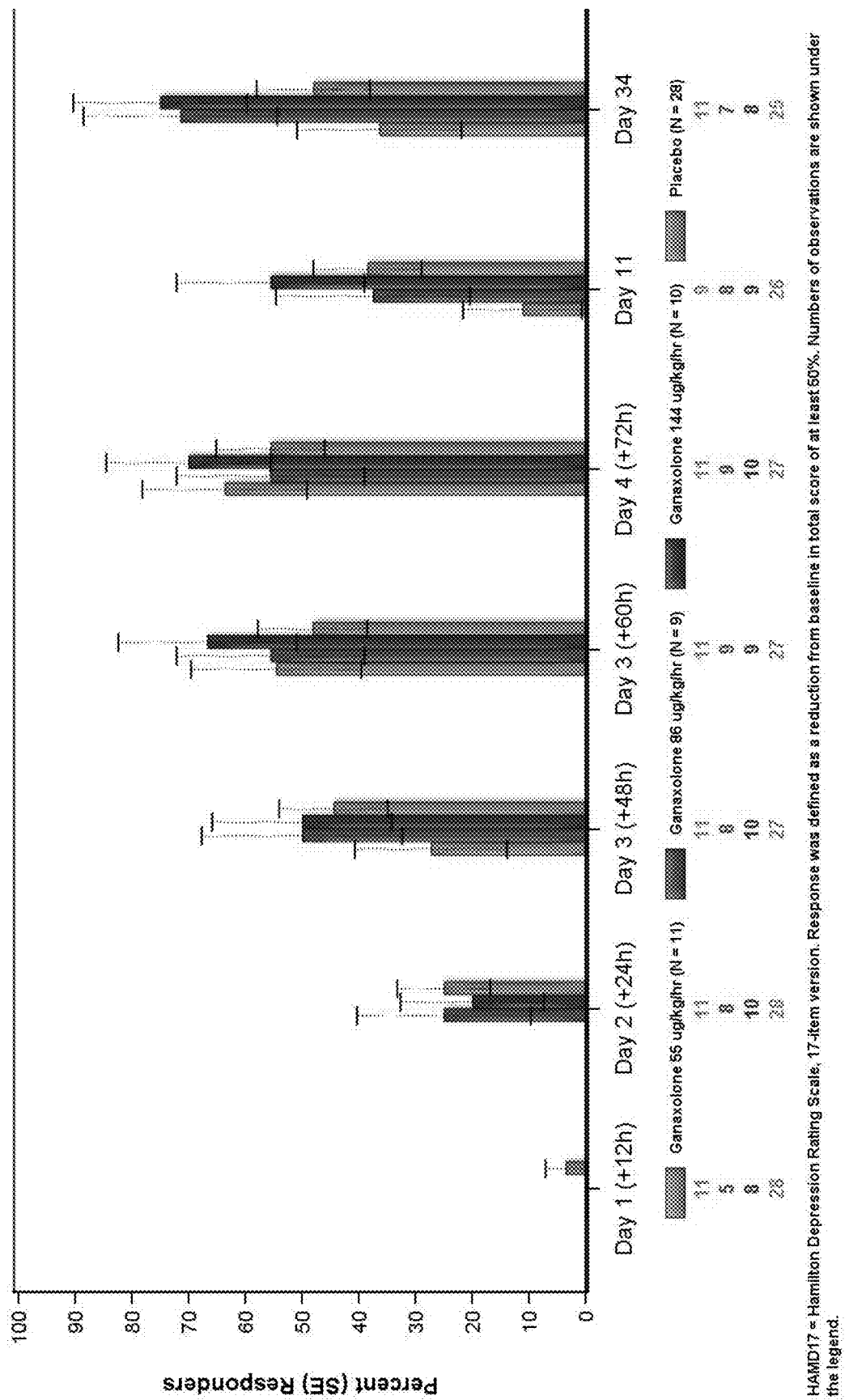
FIG. 9 depicts HAM-D17 total score—response by weight-adjusted dose for Cohorts 1-3.
Figure 10:
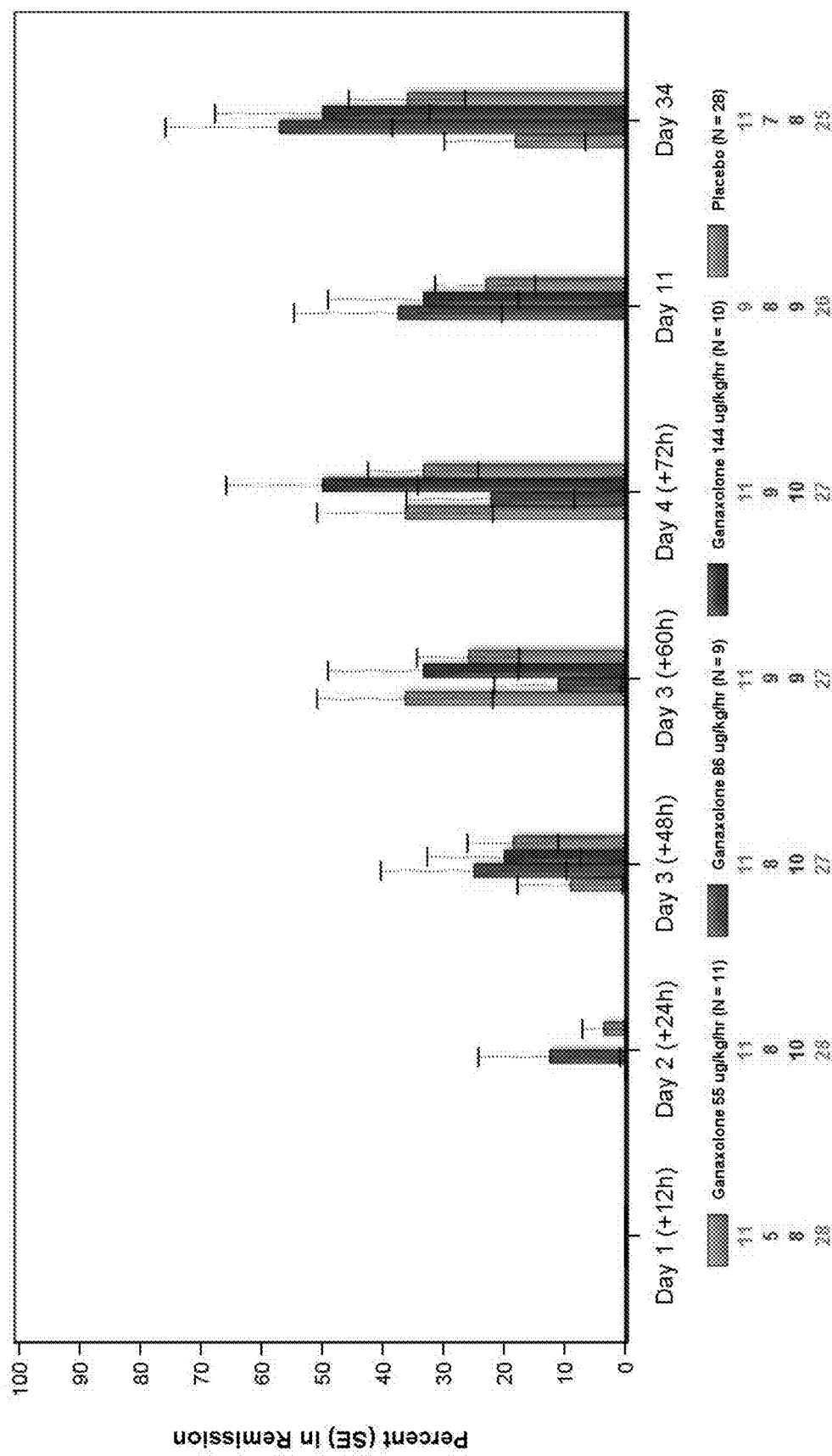
FIG. 10 depicts HAM-D17 total score—remission by weight-adjusted dose for Cohorts 1-3.
Figure 11:
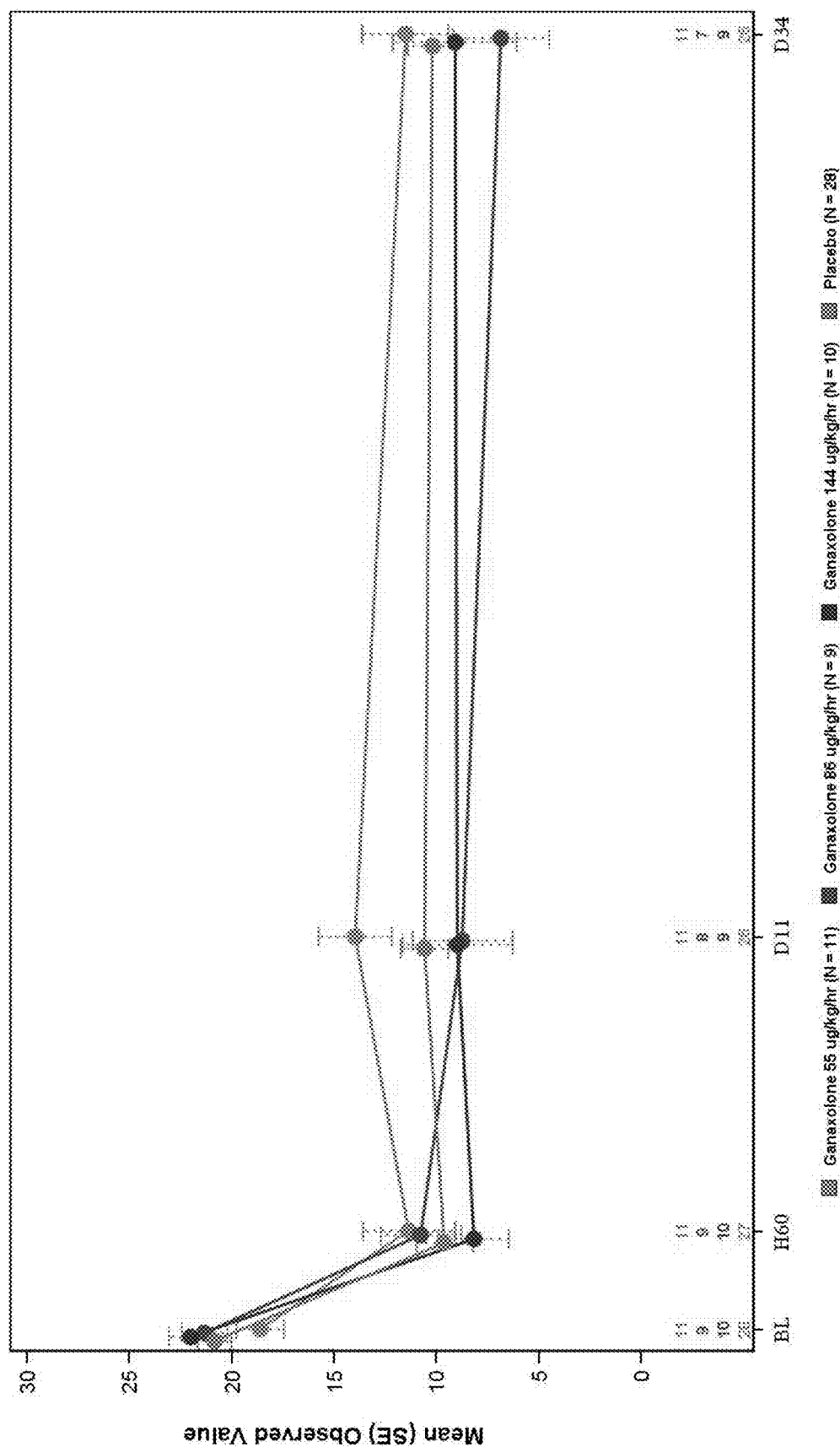
FIG. 11 depicts mean EPDS total score by weight-adjusted dose, for Cohorts 1-3.
Figure 12:
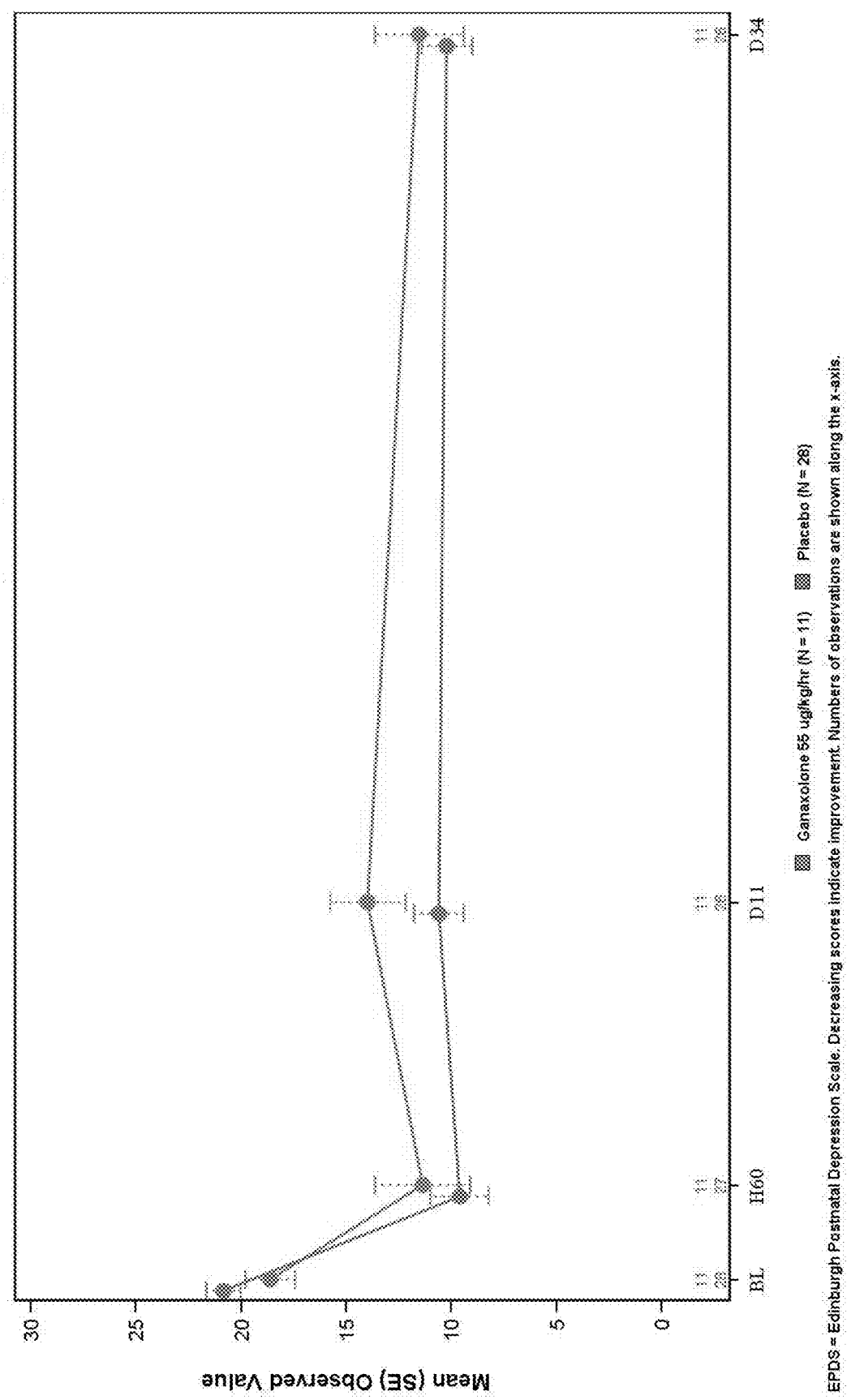
FIG. 12 depicts mean EPDS total score by weight-adjusted dose, for Cohorts 1-3, low weight-adjusted dose group (55 µg/kg/hr).
Figure 13:
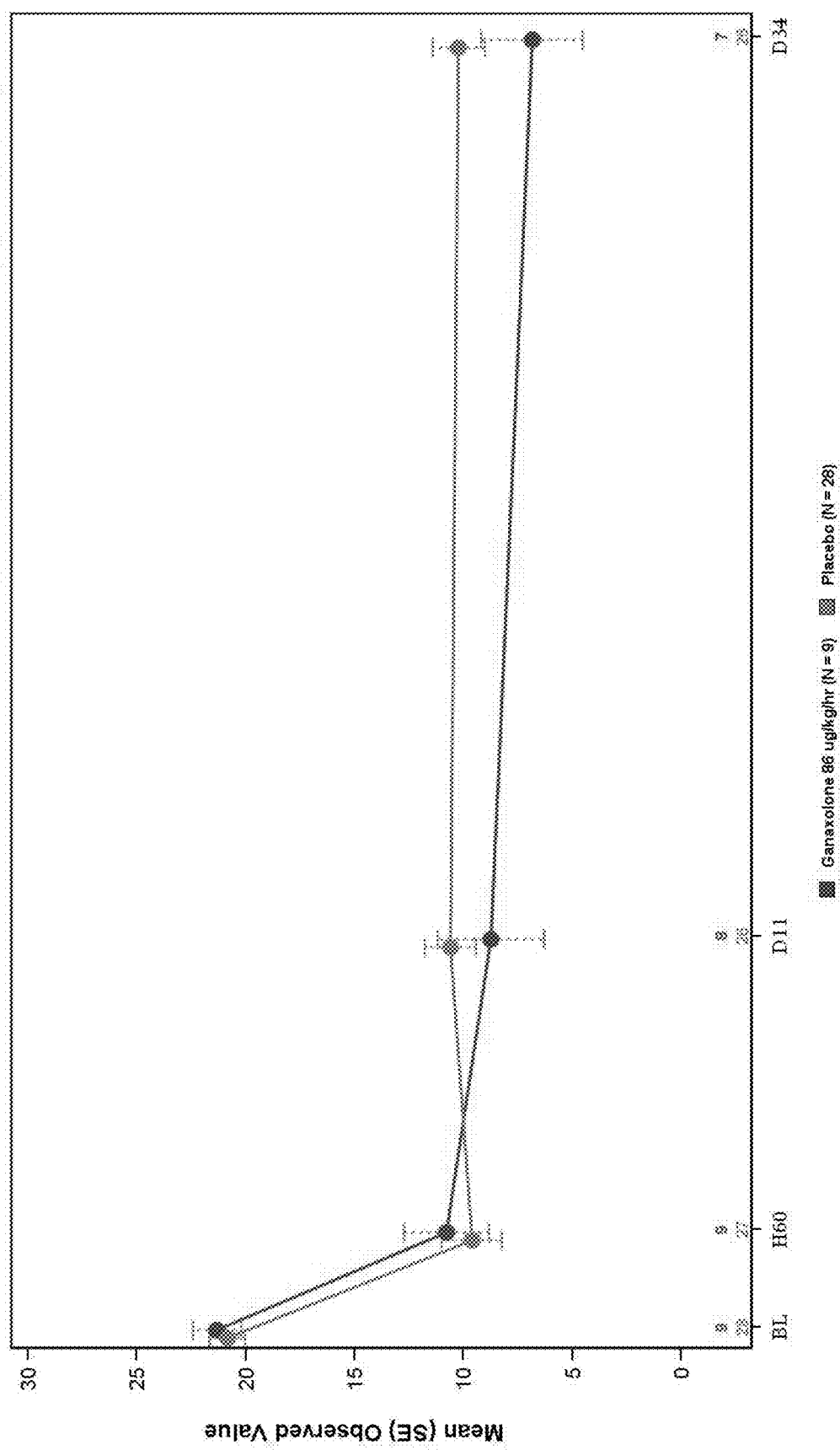
FIG. 13 depicts mean EPDS total score by weight-adjusted dose for Cohorts 1-3, medium weight-adjusted dose group (86 µg/kg/hr).
Figure 14:
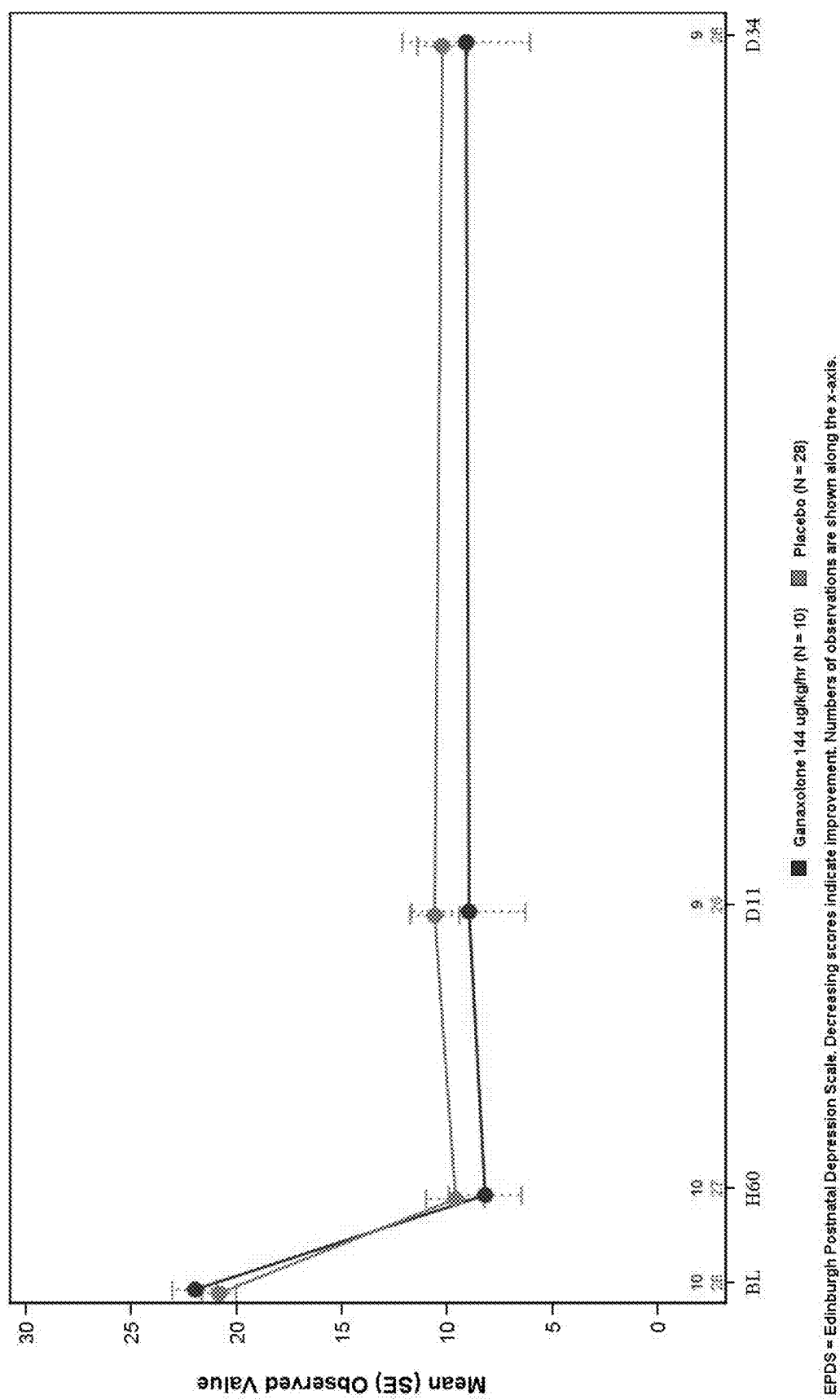
FIG. 14 depicts mean EPDS total score by Weight-Adjusted Dose for Cohorts 1-3, high weight-adjusted dose group (144 µg/kg/hr).
Figure 15:
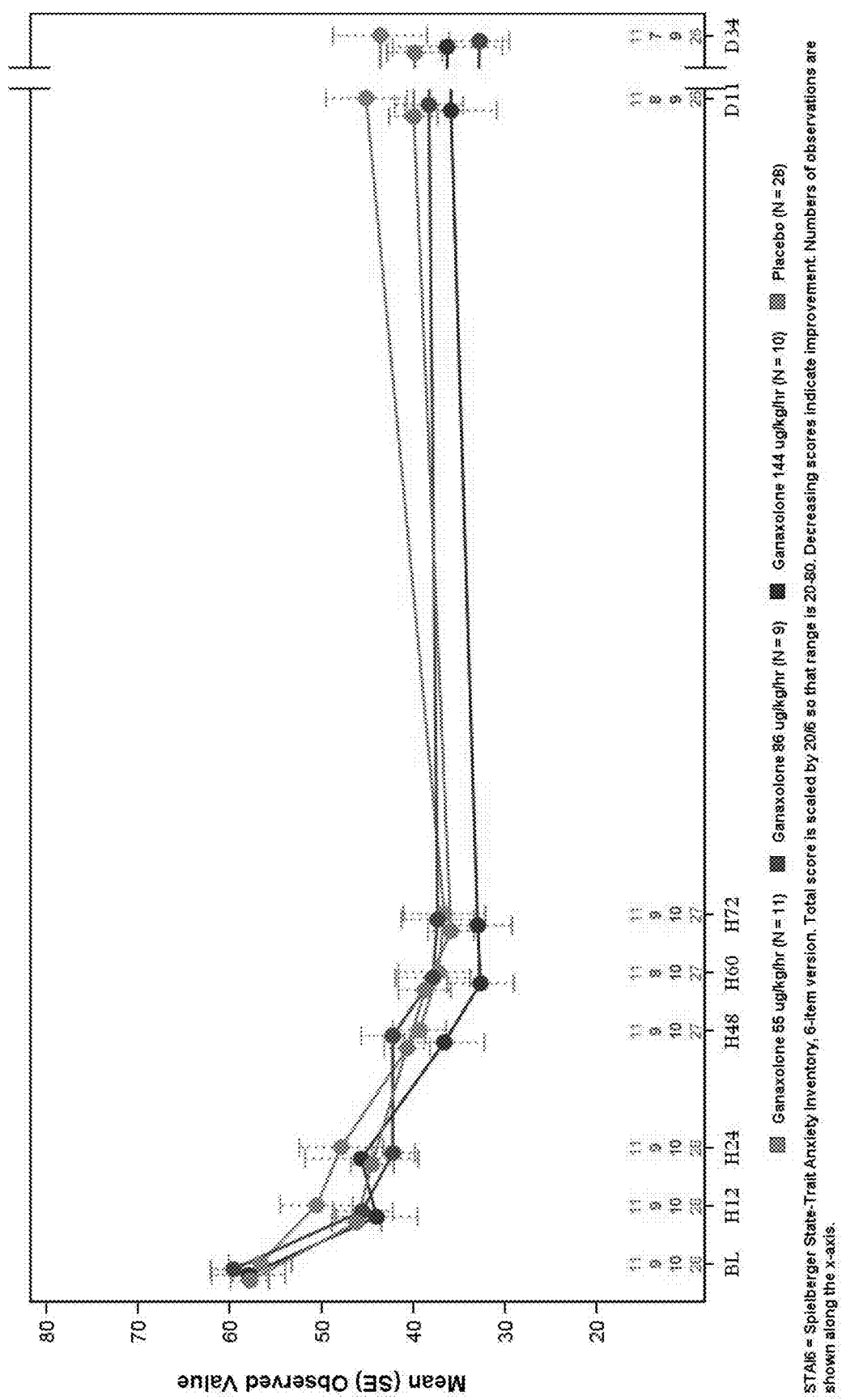
FIG. 15 depicts mean STAI6 scaled total score by weight-adjusted dose for Cohorts 1-3.
Figure 16:
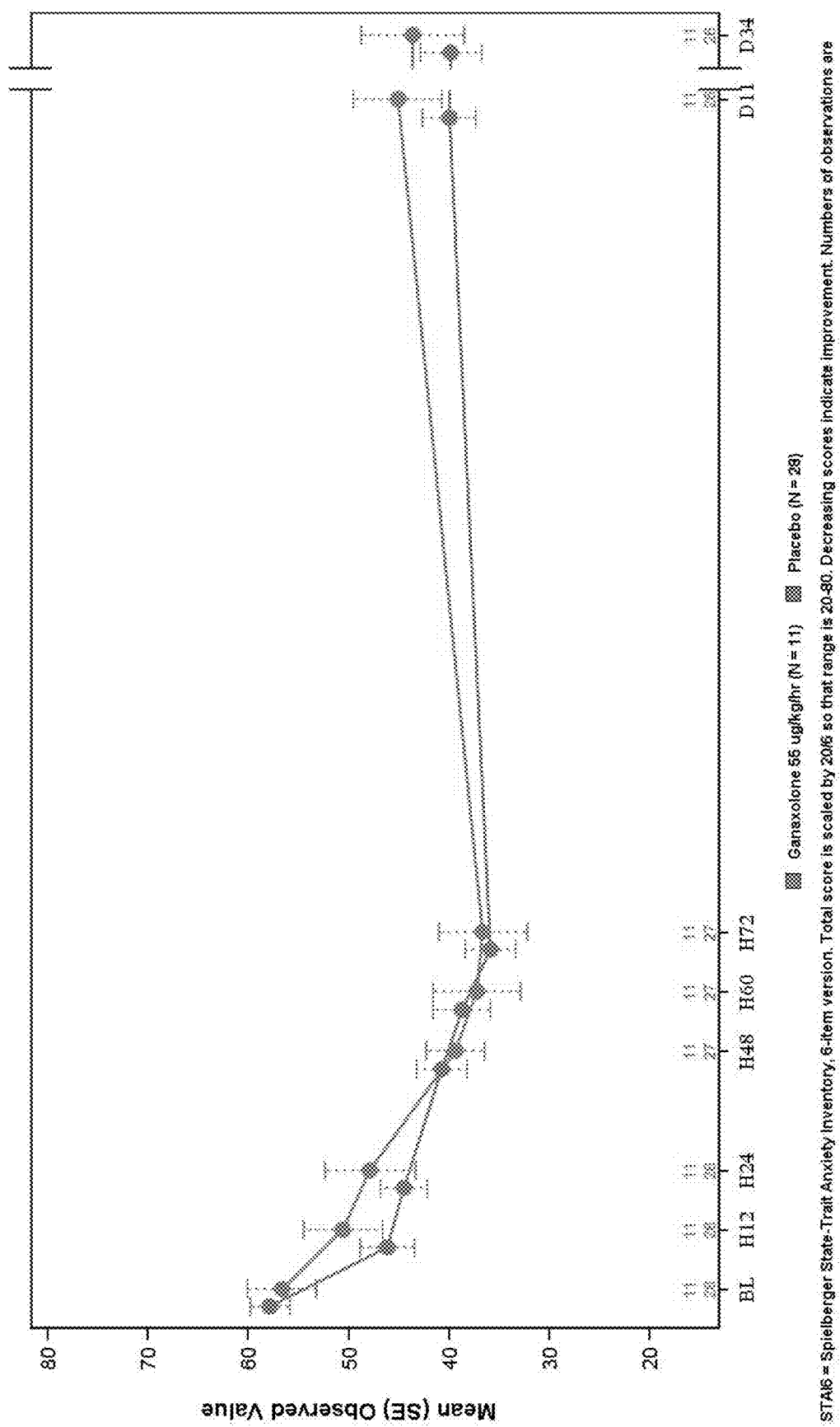
FIG. 16 depicts mean STAI6 scaled total score by weight-adjusted dose for Cohorts 1-3, low weight-adjusted dose group (55 µg/kg/hr).
Figure 17:
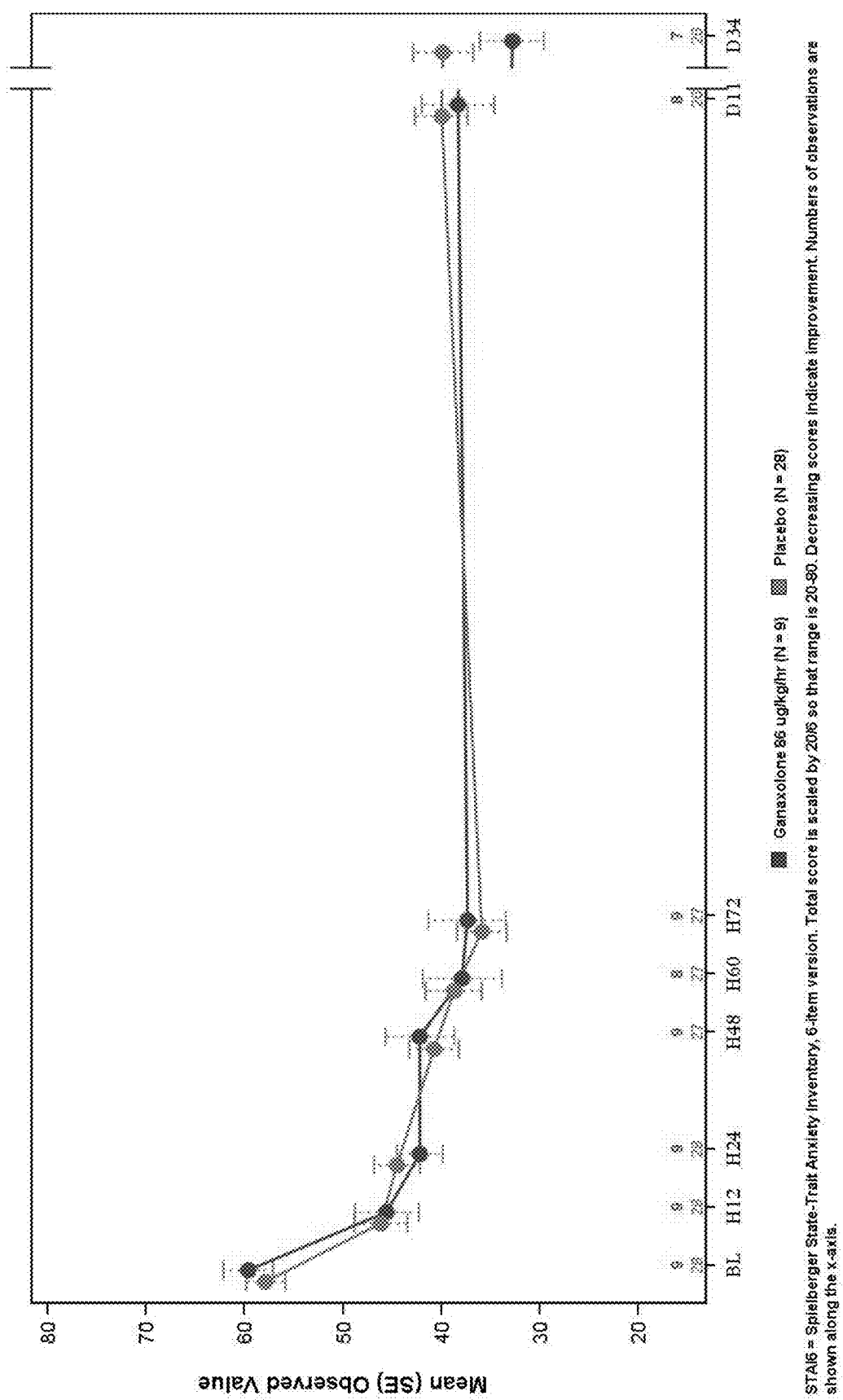
FIG. 17 depicts mean STAI6 scaled total score by weight-adjusted dose for Cohorts 1-3, medium weight-adjusted dose group (86 µg/kg/hr).
Figure 18:
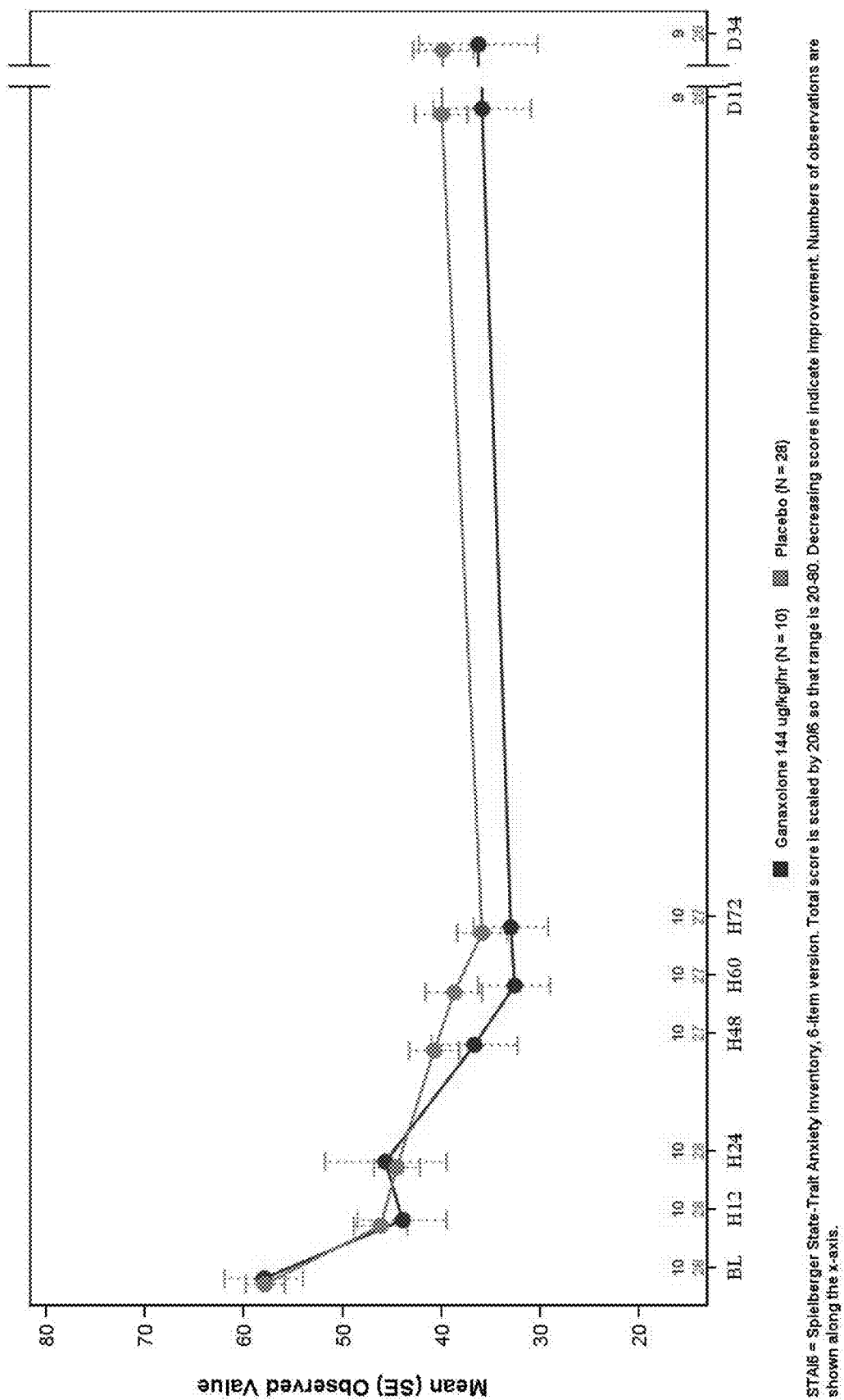
FIG. 18 depicts mean STAI6 scaled total score by weight-adjusted dose for Cohorts 1-3, high weight-adjusted dose group (144 µg/kg/hr).
Figure 19:
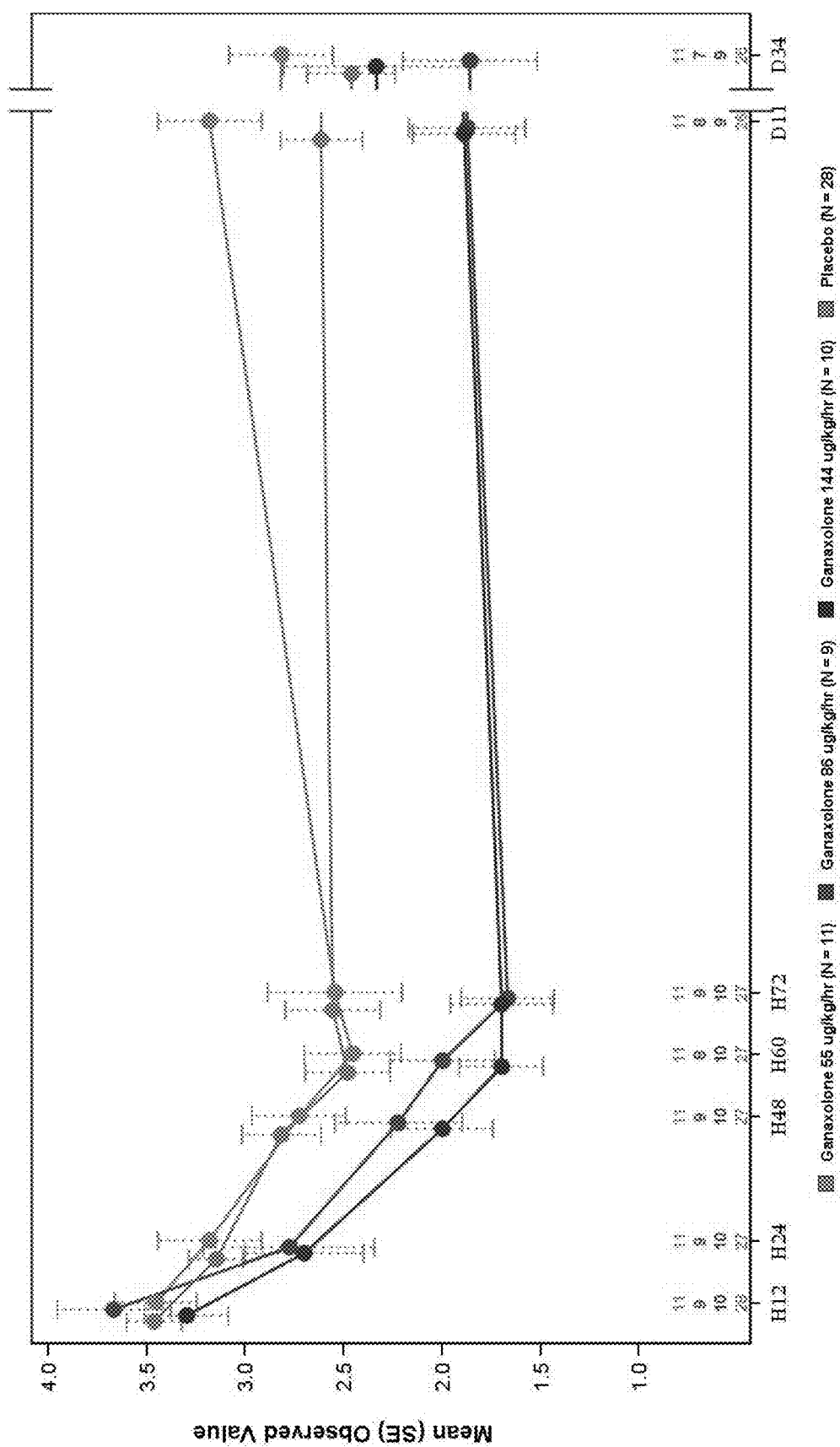
FIG. 19 depicts mean CGI-I scale by weight-adjusted dose for Cohorts 1-3.
Figure 20:
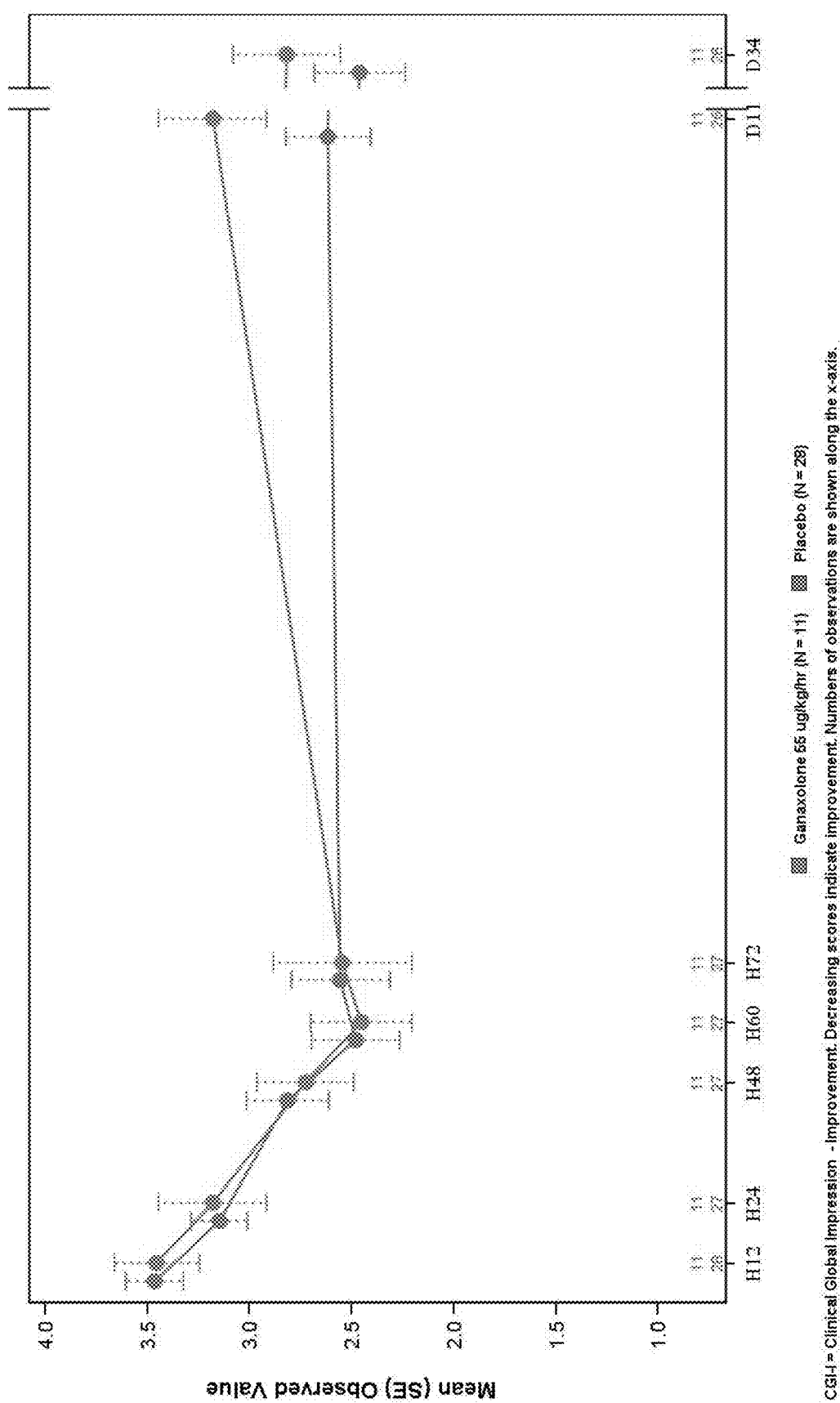
FIG. 20 depicts mean CGI-I Scale by weight-adjusted dose for Cohorts 1-3, low weight-adjusted dose group (55 µg/kg/hr).
Figure 21:
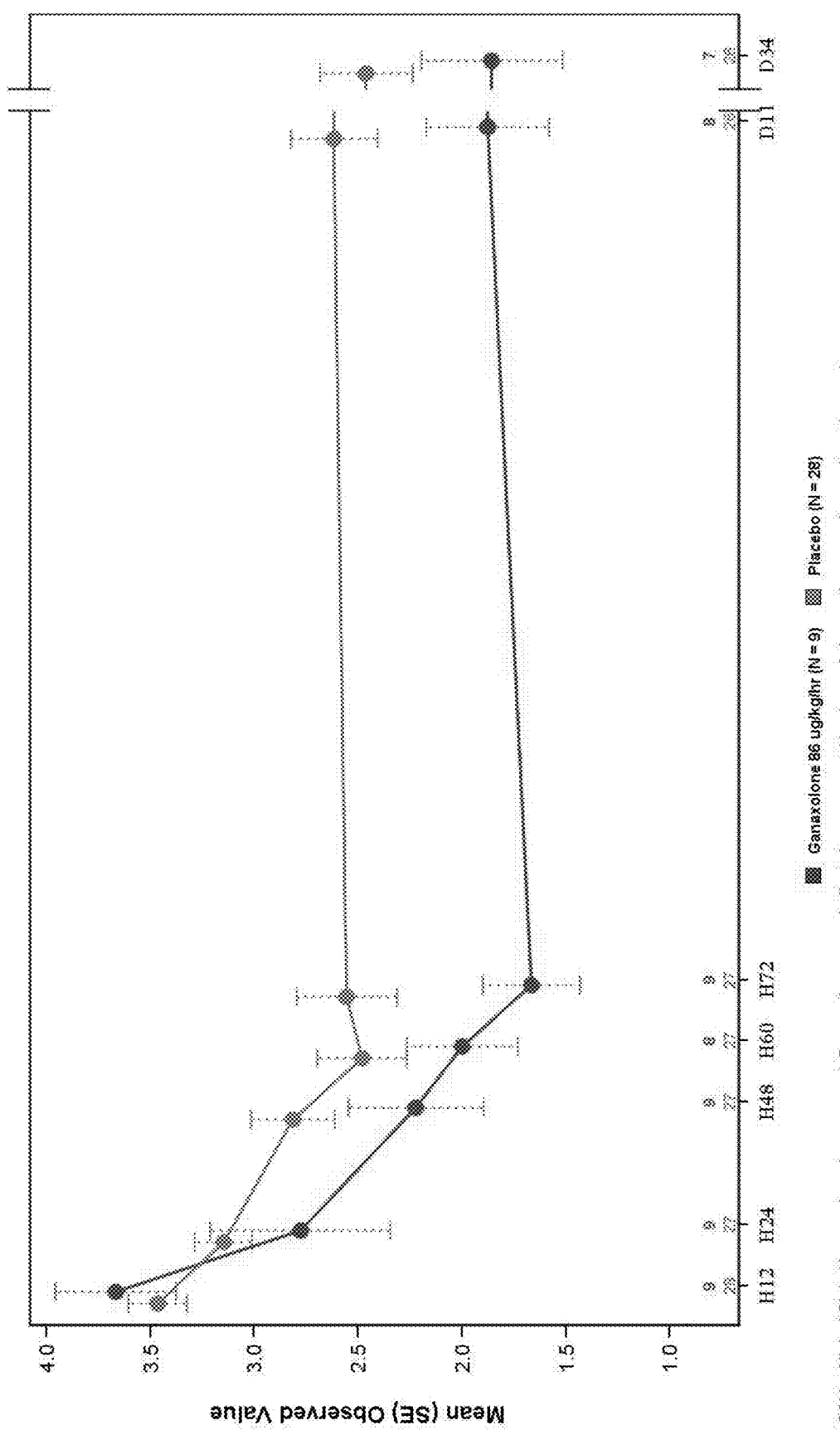
FIG. 21 depicts mean CGI-I Scale by weight-adjusted dose for Cohorts 1-3, medium weight-adjusted dose group (86 µg/kg/hr).
Figure 22:
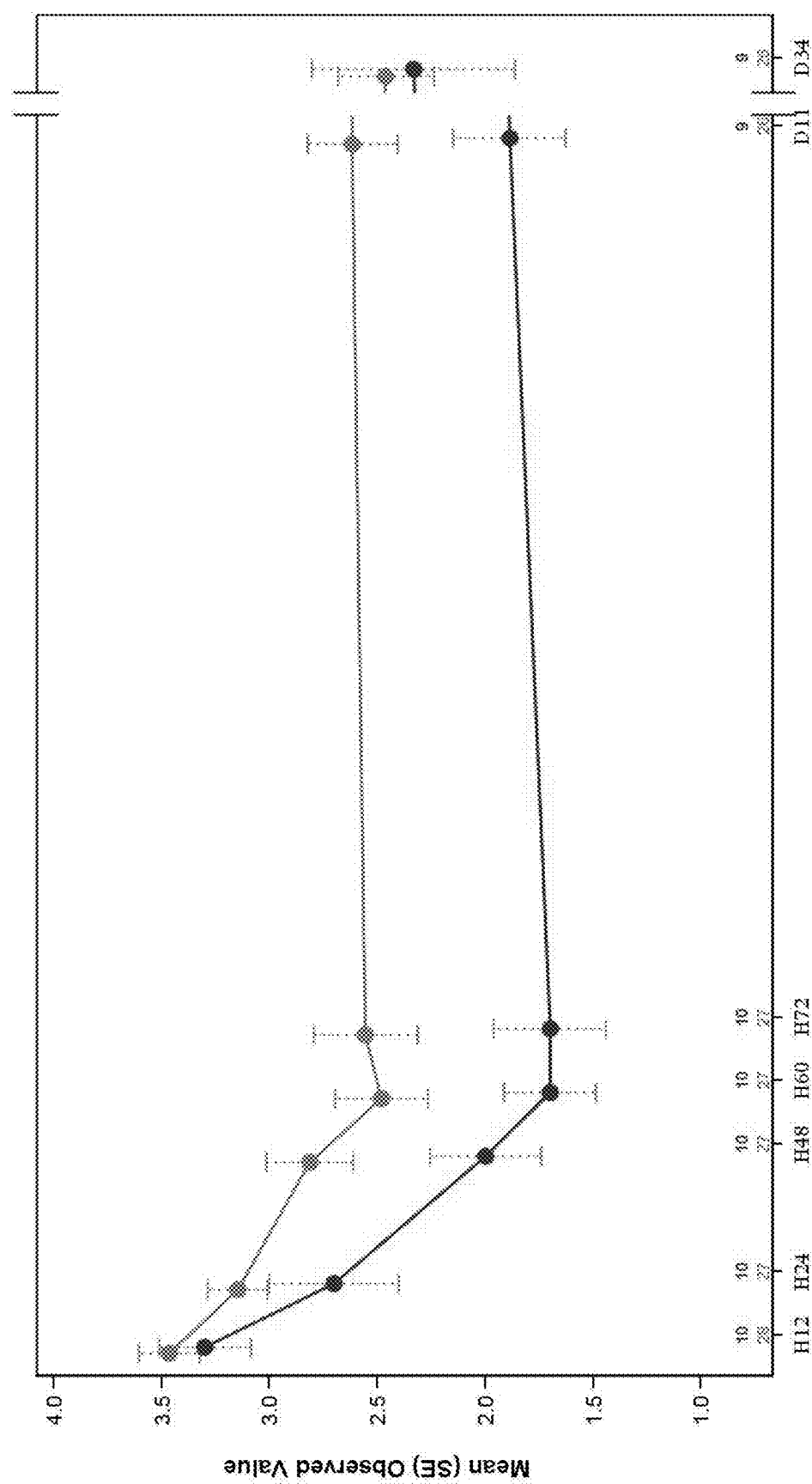
FIG. 22 depicts mean CGI-I Scale by weight-adjusted dose for Cohorts 1-3, high weight-adjusted dose group (144 µg/kg/hr).

Rapid changes in allopregnanolone and other neurosteroid levels during and after pregnancy are thought to contribute to the biological underpinnings of postpartum depression. There are also data suggesting that the sensitivity of the GABA system is altered during pregnancy and after childbirth, possibly as a result of changes in the circulating neurosteroid levels, and that there may be a state of neurosteroid withdrawal after pregnancy. Ganaxolone, when administered in accordance with the methods of the present invention, alleviates and/or reduce the severity of at least one symptom of postpartum depression by increasing neurosteroid activity in the brain, as evidenced, e.g., by a decrease in HAM-D17 score at 48 hours after administration, as compared to HAM-D17 before the start of ganaxolone administration. Plasma concentration of ganaxolone to alleviates and/or reduce the severity of at least one symptom of postpartum depression may, e.g., be from about 45 ng/ml to about 400 ng/ml (e.g., from about 100 ng/ml to about 350 ng/ml).

Ganaxolone

Ganaxolone, a synthetic analog of allopregnanolone, may alleviate symptoms of postpartum depression and provide benefit to women suffering from and/or at risk of developing postpartum depression, when administered in accordance with the methods of the invention.

Ganaxolone (CAS Reg. No. 38398-32-2, 3α-hydroxy-3β-methyl-5α-pregnan-20-one) is the 3β-methylated synthetic analog of the progesterone metabolite allopregnanolone. Allopregnanolone exhibits potent anxiolytic, antidepressant, antiepileptic, and sedative activity by virtue of its GABAA receptor modulating properties. As with allopregnanolone, ganaxolone potentiation of the GABAA receptor occurs at a site distinct from the benzodiazepine site.

Ganaxolone is the 3β-methylated synthetic analog of the endogenous neurosteroid allopregnanolone, an endogenous allosteric modulator of γ-aminobutyric acid type A ($GABA_A$) receptors in the central nervous system (CNS). Ganaxolone has the same core chemical structure as allopregnanolone, but with the addition of a 3β methyl group designed to prevent conversion back to an entity that is active at nuclear hormone receptors, thereby eliminating the opportunity for unwanted hormonal effects while enhancing the bioavailability of the neurosteroid and preserving its desired CNS activity.

The structural formula of ganaxolone is:

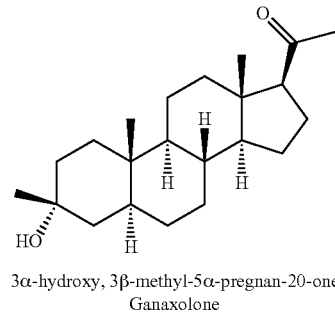

3α-hydroxy, 3β-methyl-5α-pregnan-20-one
Ganaxolone

Like allopregnanolone, ganaxolone, exhibits potent antiepileptic, anxiolytic, sedative and hypnotic activities in animals by allosterically modulating γ-aminobutyric acid type A (GABAA) receptors in the central nervous system (CNS). Ganaxolone has potency and efficacy comparable to allopregnanolone in activating synaptic and extrasynaptic GABAA receptors at a site distinct from the benzodiazepine site.

Ganaxolone works by interacting with both synaptic and extrasynaptic $GABA_A$ receptors at binding sites which are unique to the class. Outside of the synapse, ganaxolone can be absorbed into the cell membrane and diffuse to activate the extrasynaptic $GABA_A$ receptors, providing constant, or tonic, modulation of the GABA inhibitory signal that calms overexcited neurons.

Ganaxolone is insoluble in water. Its solubilities in 95% alcohol, propylene glycol and polyethylene glycol are 13 mg/mL, 3.5 mg/mL and 3.1 mg/mL, respectively.

Ganaxolone is primarily metabolized by the CYP3A family of liver enzymes, but interactions based on hepatic metabolism are limited to those caused by induction or inhibition of CYP3A4/5 by other drugs such as ketoconazole.

In vitro, the clearance of ganaxolone appears to be driven mainly by CYP3A4. In clinical studies in adults, administration of grapefruit increased the exposure of ganaxolone in healthy volunteers. Levels of ganaxolone were reduced in patients treated concomitantly with enzyme-inducing AEDs. These data further support the hypothesis of CYP3A4 being a major contributor to the clearance of ganaxolone in humans.

In the pediatric population, the level of CYP3A4 expression approaches that of adults by approximately 2 years of age (de Wildt et al, 2003), albeit with a high-degree of inter-individual variability. Therefore, patients greater than 2 years of age would be expected to have ganaxolone clearance rates similar to adults.

Ganaxolone has a relatively long half-life—approximately 20 hours in human plasma following oral administration (Nohria, V. and Giller, E., *Neurotherapeutics*, (2007)

4(1): 102-105). Furthermore, ganaxolone has a short $T_{max}$, which means that therapeutic blood levels are reached quickly.

Ganaxolone affects $GABA_A$ receptors by interacting with a recognition site that is distinct from other allosteric $GABA_A$ receptor modulators such as benzodiazepines. Ganaxolone binds to intra- and extrasynaptic receptors, mediating both phasic and tonic modulation, respectively. The unique binding of Ganaxolone to these 2 receptors does not lead to the tolerance seen with benzodiazepines. In contrast to allopregnanolone, ganaxolone is orally bioavailable and cannot be back-converted in the body to intermediates such as progesterone, with classical steroid hormone activity, and as such, does not directly or indirectly via metabolic conversion activate the progesterone receptor.

Ganaxolone has been shown to have anxiolytic properties as well as improve behaviours associated with autism. In a mouse model of posttraumatic stress disorder (PTSD), treatment with ganaxolone decreased aggression and social isolation-induced anxiety-like behaviour (Pinna and Rasmussen, 2014). In another study, ganaxolone treatment improved sociability in the BTBR mouse model of autism (Kazdoba et al, 2016). A clinical study of ganaxolone treatment of children and adolescents with fragile X syndrome (FXS), ganaxolone reduced anxiety and hyperactivity and improved attention in those with higher baseline anxiety (Ligsay et al, 2017).

Safety pharmacology studies were conducted with ganaxolone.

Ganaxolone did not interact with the human ether-a-go-go related gene (hERG) receptor at a measured concentration of 70 nM (n=2). Ganaxolone had no effect on cardiovascular parameters in dogs following a single dose of up to 15 mg/kg (maximum concentration [Cmax] of 1000 ng/mL and area under the concentration time curve (AUC)(0-24) of 10000 ng·h/mL). In the 1-year dog toxicity study (Cmax>1500 ng/mL), transient sinus tachycardia (>190 beats per minute [bpm]) was observed after 3 months of dosing in 4 animals and was accompanied by decreased PR and QT interval but no treatment effect on QRS duration or Q-T interval corrected (QTc). No pulmonary effects were observed in female rats at doses up to 40 mg/kg.

There was a physiologically normal shortening of the PR and QT interval in response to the higher heart rate. There was no effect on QRS duration or QTc interval. No pulmonary effects were observed in female rats at doses up to 40 mg/kg.

Ganaxolone induces major cytochrome P450 (CYP) isoenzymes 1A1/2 and 2B1/2 in female rats but not males. Auto-induction has also been observed in the mouse and rat while no auto-induction has been observed in dogs.

Tissue distribution studies in mice and rats have demonstrated that [$^{14}$C]-ganaxolone was rapidly distributed throughout the body into highly perfused organs, intestine, and adipose tissue, with brain ganaxolone concentrations approximately 5-fold higher than those in plasma.

Most excreted radioactivity in all species is via faeces (>70%) with the remaining excreted in urine.

The most common effect following treatment with ganaxolone in toxicology studies was dose-related sedation, an expected pharmacological effect of a positive modulator of $GABA_A$ receptors. In both the oral and IV programmes, there was little evidence of target organ or systemic toxicity associated with either single- or multiple-dose treatment with ganaxolone. No functional or anatomic changes within haematopoietic tissue or any specific organ such as liver, kidney or gastrointestinal (GI) systems were seen in the repeat-dose studies. In rats, ganaxolone induced hepatic enzymes, with more pronounced effects in females, which were correlated to increased liver weights and dose related hepatocellular hypertrophy in a 6-month study.

In the chronic oral toxicity study in dogs, mean $C_{max}$ levels of greater than 1500 ng/mL (10 and 15 mg/kg/day) were associated with increased weight and total plasma cholesterol levels.

When given IV to rats and dogs, the main dose limiting toxicity finding was sedation. The no observed adverse effect level (NOAEL) after IV dosing in rats for 14 days was established at 42 mg/kg/day for males and 30 mg/kg/day for females. The NOAEL in dog after administration of ganaxolone by IV bolus followed by continuous IV infusion for 28 days was 7.20 mg/kg/day, which corresponded to a steady-state concentration of approximately 330 ng/mL and 333 ng/mL. There were no findings in a local tolerance study in rabbits. Finally, in vitro ganaxolone did not cause haemolysis and was compatible with human plasma.

Ganaxolone was not teratogenic in rats or mice and did not significantly affect the development of offspring. Ganaxolone had no effects on fertility and early embryonic development in rats. No potential for mutagenicity was detected. Treatment of neonatal rats with ganaxolone produced expected signs of sedation but did not affect development or demonstrate any post-mortem changes.

Ganaxolone Summary of Safety

Across all placebo-controlled studies, there were no events of loss of consciousness related to ganaxolone. There were no events of pre-syncope reported; and the incidence of syncope was low and reported by comparable number of subjects in ganaxolone (0.2%; 2/993) and placebo (0.2%; 1/637) groups.

As of Oct. 10, 2017, 1557 unique subjects have received ganaxolone ranging in duration from 1 day to more than 2 years using doses from 50 to 2000 mg/day in completed studies. Of these subjects, 1527 subjects received oral ganaxolone and 30 subjects received intravenous (IV ganaxolone).

In 20 completed Phase 1 studies, 319 healthy subjects received ganaxolone oral doses of 50 to 2,000 mg/day for periods of up to 2 weeks or IV bolus doses ranging from 10 to 30 mg over durations of 2 minutes to 1 hour or a bolus dose of 6 mg over 5 minutes followed with a continuous infusion of 20 mg per hour for 4 hours.

In the 20 completed Phase 2/3 clinical studies, 1238 unique subjects have received oral ganaxolone in studies of adult subjects with epilepsy, pediatric subjects with seizure disorders, pediatric subjects with FXS, adult subjects with PTSD, and adult subjects with migraine.

Ganaxolone Summary of Adverse Effects

In clinical trials of ganaxolone, adverse events (AEs) related to the GABAergic mechanism of action in the CNS were reported more commonly in subjects receiving ganaxolone than placebo. In general, the frequency of these events has been dose related. Most of these effects were reported as mild or moderate and were reversible after dose decrease or drug discontinuation.

In all completed placebo-controlled studies, 61.7% (613/993) of subjects who received ganaxolone and 51.8% (330/637) of subjects who received placebo experienced at least 1 treatment emergent adverse event (TEAE). In these studies, the most frequently reported (i.e., in ≥5% of subjects), TEAEs in ganaxolone-treated subjects were CNS-related: somnolence (22.0% ganaxolone, 6.4% placebo), dizziness (13.0% ganaxolone, 4.2% placebo), fatigue (9.7% ganaxolone, 5.2% placebo), and headache (5.5% ganaxolone, 7.7% placebo). All of these events, except headache, occurred more frequently in ganaxolone-treated subjects than placebo subjects.

In placebo-controlled studies adverse event of rash led to discontinuations in ganaxolone-treated subjects in 6 cases (6/993; 0.6%) compared to no cases (0/637; 0%) in placebo-treated subjects. One of the events was also reported as an SAE. In addition, in one ongoing study, an additional event of rash was reported as an SAE. Both SAEs resolved after discontinuation of the study drug. There have been no cases of Stevens-Johnson syndrome, toxic epidermal necrolysis or any other clinically important rashes reported in the clinical development program.

Summary of safety of IV ganaxolone

Preclinical studies and a study in 36 healthy volunteers assessing safety, pharmacokinetics and pharmacodynamics of intravenously administered ganaxolone has been completed. Preclinical toxicity studies showed intravenous (IV) ganaxolone to be generally safe and adverse events consistent with expected dose-related sedation. In rats continuously dosed with IV ganaxolone for 14 days, no ganaxolone-related changes were noted in clinical pathology parameters or histopathology examination. There was no evidence of local irritation when ganaxolone was given intra- or perivenously in preclinical studies. Furthermore, IV ganaxolone did not cause hemolysis and was compatible with human plasma.

The safety, pharmacokinetics and pharmacodynamics of IV ganaxolone were investigated in healthy 36 volunteers, in which ganaxolone was administered as a bolus dosing (Stage 1) or as a bolus dose followed by a continuous infusion (Stage 2). Ten of the 36 subjects enrolled were women. Stage 1 enrolled and dosed subjects in 4 cohorts (A-D): 6 subjects in Cohort A (10 mg ganaxolone IV bolus in 3 subjects and 30 mg ganaxolone bolus in 3 subjects over 5-minutes), 8 subjects in Cohort B (20 mg ganaxolone bolus over 2-minutes), 8 subjects in Cohort C (30 mg ganaxolone bolus over 1-hour) and 8 subjects in Cohort D (10 mg ganaxolone bolus over 1-hour). Cohorts B, C and D included 2 placebo subjects in each cohort. Stage 2 of the study dosed a total of 6 subjects with a 6 mg bolus followed by a 4-hour infusion at 20 mg/h. Ten of the 36 subjects enrolled in the study were women.

A total of 35 of the 36 subjects enrolled in Stages 1 and 2 completed the study as planned while 1 subject withdrew their consent. Six subjects reported treatment emergent AEs in Stage 1 and 2. No single AE was seen twice. Only one event, headache, was considered by the investigator to be related to ganaxolone. None of the treatment emergent AEs were serious, and all were of mild intensity. No clinically meaningful mean changes in laboratory test results, vital signs, or ECG parameters occurred in any cohort.

Pharmacokinetic data shows that a bolus infusion of 30 mg ganaxolone over 5-minutes led to peak concentration levels (Cmax) of >1,000 ng/ml with no safety concerns (except sedation). Infusion of 30 mg/hr for 1 hour, 20 mg over 2 minutes and 20 mg/hr for 4 hours led to peak concentrations of 258 ng/mL, 441 ng/mL and 215 ng/mL, respectively, again without any safety concerns. This is consistent with findings from previous studies with the oral formulation of ganaxolone, in which Cmax levels of up to 200 to 300 ng/mL were commonly observed and were not associated with major safety findings or toxicity (apart from sedation-related effects).

Other Ganaxolone Safety Information

Ganaxolone is metabolized by CYP3A4/5, and in vitro data and human PK data from subjects taking strong CYP inducers (carbamazepine and phenytoin) has shown increased ganaxolone clearance with approximately a 45% lowering in overall ganaxolone levels and exposure.

In the ganaxolone development program overall, no clinically significant trends in electrocardiogram (ECG) intervals, vital signs, or physical or neurological examinations have been noted, and no mean changes from baseline in clinical laboratory results have been identified. In the completed placebo-controlled Phase 1, 2, and 3 studies, 0.32% of subjects who received ganaxolone and 0.46% of subjects who received placebo developed elevated LFTs during the study (>3×ULN AST and/or ALT). A subject participating in the ganaxolone pediatric epilepsy study developed liver failure, which was not considered to be related to ganaxolone. The subject was diagnosed with short bowel syndrome, liver steatosis and IgG-cholangitis, which were considered to be the causal factors for the subject's liver failure. There have been no other cases of Hy's Law or liver failure in the ganaxolone development program.

It is not known if ganaxolone is excreted to breast milk. After cessation of the dosing, plasma ganaxolone levels are expected to drop rapidly, but it is possible that low sub-therapeutic levels persist for several days as ganaxolone is slowly released from tissues.

Previous toxicology studies in animals focusing on pre-natal and neonatal development have not demonstrated toxicities associated with ganaxolone. Ganaxolone has been administered to infants with severe forms of epilepsy as early as 4 months of age.

In clinical trials involving administration of ganaxolone over several weeks, the study drug has been tapered off over a 1 to 2-week period. There have been no reports of withdrawal symptoms emerging after cessation of ganaxolone.

Diagnosis and Efficacy Assessment

Hamilton Depression Rating Scale HAM-D

The Hamilton Depression Rating Scale (HAM-D) is a commonly-used semi-structured clinician-rated instrument which assesses the range of symptoms that are most frequently observed in subjects with major depression. HAM-D has undergone a considerable amount of psychometric study and is accepted as a valid standard of symptom outcome assessment in studies of major depression. In the examples disclosed herein HAM-D was scored using the original 17-item HAM-D scale (HAM-D17).

Reduction in Mean HAM-D Score (i.e., Least-Squares (LS) Mean Reduction)

Administration of ganaxolone in accordance with the methods of the present invention provides a reduction in HAM-D score at about 6 hours and/or at about 12 hours and/or about 24 hours (about 1 day) and/or about 48 hours (about 2 days) and/or about 60 hours (about 2.5 days) and/or about 72 hours (about 3 days) and/or about 11 days and/or about 30 days and/or about 34 days, as compared to the baseline HAM-D score (i.e., the HAM-D score at the time of initiation of the infusion (at 0 hours)). In certain embodiments, administration of ganaxolone in accordance with the methods of the invention provides a reduction in HAM-D score at 2 days, 3 days and 11 days. In certain embodiments, administration of ganaxolone in accordance with the methods of the present invention provides a reduction in HAM-D score at about 6 hours, 2 days, 3 days and 11 days. In certain embodiments, administration of ganaxolone in accordance with the methods of the present invention provides a reduction in HAM-D score at about 7 hours, 2 days, 3 days and 11 days. In certain embodiments, administration of ganaxolone in accordance with the methods of the present invention provides a reduction in HAM-D score at about 8 hours, 2 days, 3 days and 11 days. The difference in mean HAM-D total score between the score at the time of the injection and a subsequent time point (e.g., about 6 hours and/or at about 12 hours and/or about 24 hours (about 1 day) and/or about 48 hours (about 2 days) and/or about 60 hours (about 2.5 days) and/or about 72 hours (about 3 days) and/or about 11 days and/or about 30 days and/or about 34 days) may e.g., be a reduction of 1, 2, 3, or 4 to 28 points. In the preferred embodiments, the reduction in mean HAM-D total score achieved by administration of ganaxolone is 2, 2.5 or 3 points greater than the reduction in mean HAM-D total score achieved after administration of placebo.

In certain embodiments, administration of ganaxolone in accordance with the methods of the present invention provides a reduction in HAM-D score at about 6 hours, as compared to HAM-D score at 0 hours. In these embodiments, ganaxolone is generally administered via a single intravenous infusion of ganaxolone at a dose and rate of greater than 30 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, administration of ganaxolone in accordance with the methods of the present invention provides a reduction in HAM-D score at about 12 hours, as compared to HAM-D score at 0 hours. In these embodiments, ganaxolone is generally administered via a single intravenous infusion at a dose and rate of greater than 30 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, administration of ganaxolone in accordance with the methods of the present invention provides a reduction in HAM-D score at about 24 hours, as compared to HAM-D score at 0 hours. In these embodiments, ganaxolone is generally administered via a single intravenous infusion at a dose and rate of 75 μg/kg/hr or greater wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 to 12 hours of the infusion. The infusion may be for a time period of from 1 hour to 80 hours.

In certain embodiments, the administration of ganaxolone in accordance with the methods of the present invention provides a reduction in HAM-D score at about 48 hours, as compared to HAM-D score at 0 hours. In these embodiments, ganaxolone is generally administered via a single intravenous infusion at a dose and rate of 75 μg/kg/hr or greater, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the administration of ganaxolone in accordance with the methods of the present invention provides a reduction in HAM-D score at about 60 hours, as compared to HAM-D score at 0 hours. In these embodiments, ganaxolone is generally administered via a single intravenous infusion at a dose and rate of greater than 115 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the administration of ganaxolone in accordance with the methods of the present invention provides a reduction in HAM-D score at about 34 days, as compared to HAM-D score at 0 hours. In these embodiments, ganaxolone is generally administered via a single intravenous infusion at a dose and rate of greater than 75 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 to 12 hours of the infusion. The infusion may be for a time period of from 1 hour to 80 hours.

In certain embodiments, the administration of ganaxolone in accordance with the methods of the present invention provides a reduction in HAM-D score at about 60 hours, about 11 days and about 34 days, all as compared to HAM-D score at 0 hours. In these embodiments, ganaxolone is generally administered via a single intravenous infusion at a dose and rate of greater than 115 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the baseline HAM-D score is from 11 to 50, and the HAM-D score at the end of the treatment is 10 or less (e.g., 9, 8, 7, 6, 5, 4, 3, 2, 1, or 0).

Mean Change in HAM-D Score

Administration of ganaxolone in accordance with the methods of the present invention may provide a mean change in HAM-D score (i.e., least-squares (LS) mean reduction) at about 6 hours and/or at about 12 hours and/or about 24 hours (about 1 day) and/or about 48 hours (about 2 days) and/or about 60 hours (about 2.5 days) and/or about 72 hours (about 3 days) and/or about 11 days and/or about 30 days and/or about 34 days of from about 2 to about 17. In the preferred embodiments, the mean change in HAM-D score is greater than placebo.

In certain embodiments, the administration of ganaxolone in accordance with the methods of the present invention provides a mean change in HAM-D score at 12 hours of about 1, about 2, about 3, about 4, about 5, or greater. In the preferred embodiments, the improvement is greater than with a placebo. In these embodiments, ganaxolone is generally administered at a dose and rate of greater than 115 μg/kg/hr.

In certain embodiments, the administration of ganaxolone in accordance with the methods of the present invention provides a mean change in HAM-D score at about 24 hours of about 2, about 3, about 4, about 5, about 6, about 7, about 8, about 10, or greater. In the preferred embodiments, the improvement is greater than with a placebo. In these embodiments, ganaxolone is generally administered at a dose and rate of greater than 75 μg/kg/hr.

In certain embodiments, the administration of ganaxolone in accordance with the methods of the present invention provides a mean change in HAM-D score at about 48 hours of about 8, about 9, about 10, about 11, about 12, about 14, about 15, about 16, or greater. In the preferred embodiments, the improvement is greater than with a placebo. In these embodiments, ganaxolone is generally administered at a dose and rate of greater than 75 μg/kg/hr.

In certain embodiments, the administration of ganaxolone in accordance with the methods of the present invention provides a mean change in HAM-D score at 60 hours of about 10, about 11, about 12, about 13, about 14, about 15, about 16 or about 17, or greater. In the preferred embodiments, the improvement is greater than with a placebo. In these embodiments, ganaxolone is generally administered via a single intravenous infusion at a dose and rate of greater than 115 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 to 12 hours of the infusion. The infusion may be for a time period of from 1 hour to 80 hours.

In certain embodiments, the administration of ganaxolone in accordance with the methods of the present invention provides a mean change in HAM-D score at about 72 hours of about 10, about 11, about 12, about 13, about 14, about 15, about 16 or about 17, or greater. In the preferred embodiments, the improvement in the HAM-D score is greater than with a placebo. In these embodiments, ganaxolone is generally administered via a single intravenous infusion at a dose and rate of greater than 75 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the administration of ganaxolone in accordance with the methods of the present invention provides a mean change in HAM-D score at about 11 days of about 3, about 4, about 5, about 6, about 7, about 8, about 9, about 10, about 11, about 12, about 13, about 14, or greater. In the preferred embodiments, the improvement in the HAM-D score is greater than with a placebo. In these embodiments, ganaxolone is generally administered via a single intravenous infusion at a dose and rate of greater than 75 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the administration of ganaxolone in accordance with the methods of the present invention provides a mean change in HAM-D score at about 11 days of from about 12 to about 17, or greater. In the preferred embodiments, the improvement in the HAM-D score is greater than with a placebo. In these embodiments, ganaxolone is generally administered via a single intravenous infusion at a dose and rate of greater than 144 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, the administration of ganaxolone in accordance with the methods of the present invention provides a mean change in HAM-D score at about 34 days of about 8, about 9, about 10, about 11, about 12, about 14, about 15, about 16, about 17, or greater. In the preferred embodiments, the improvement in the HAM-D score is greater than with a placebo. In these embodiments, ganaxolone is generally administered via a single intravenous infusion at a dose and rate of greater than 75 μg/kg/hr, wherein from about 70% to about 95% of the dose is administered at a first constant rate (mg/hr) for the first 1 to 48 hours of the infusion, and from about 5% to about 30% of the dose is administered at a second constant rate (mg/hr) for the last 1 to 12 hours of the infusion. The infusion may be for a time period of from 1 hour to 80 hours.

In certain embodiments, administration of ganaxolone provides an improvement over placebo, the difference between ganaxolone and placebo treatment groups being 0.7, 1.5, 5.6, 4.2, 2.9, 5.9, and 4.1 at 12 hours, 24 hours, 48 hours, 60 hours, 72 hours, 11 days, and 34 days.

In certain embodiments, administration of ganaxolone may provide a mean Δ HAM-D difference from placebo (improvement over placebo) at about 4 at about 60 hours, about 6 at about 11 days and 5 at about 34 days. In these embodiments, ganaxolone is generally administered via a single intravenous infusion at a dose and rate of greater than 115 μg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hours to 12 hours of the infusion. The infusion may be for a time period of from 1 hour to 80 hours.

HAM-D Response

Administration of ganaxolone in accordance with the methods of the present invention may result in a greater proportion of patients achieving a HAM-D response, as compared to placebo, at about 6 hours and/or at about 12 hours and/or about 24 hours (about 1 day) and/or about 48 hours (about 2 days) and/or about 60 hours (about 2.5 days) and/or about 72 hours (about 3 days) and/or about 11 days and/or about 30 days and/or about 34 days.

In certain embodiments, from about 56% to about 95% of patients receiving ganaxolone achieve HAM-D response at about 48 hours, whereas only from 45% to 48% of patients receiving placebo achieve HAM-D response at about 48 hours. In these embodiments, ganaxolone is generally administered at a dose and rate of 75 μg/kg/hr or greater (e.g., 86 μg/kg/hr, 144 μg/kg/hr, etc.).

In certain embodiments, from about 63% to about 95% of patients receiving ganaxolone achieve HAM-D response at about 60 hours, whereas only from 48% to 49% of patients achieve HAM-D response at about 60 hours. In these embodiments, ganaxolone is generally administered via a single intravenous infusion at a dose and rate of 55 μg/kg/hr or greater (e.g., 86 μg/kg/hr, 144 μg/kg/hr, etc.), wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 50% to about 95% of patients receiving ganaxolone achieve HAM-D response at about 72 hours, whereas only from 55% to 56% of patients receiving placebo achieve HAM-D response at about 72 hours. In these embodiments, ganaxolone is generally administered via a single intravenous infusion at a dose and rate of 55 µg/kg/hr or 115 µg/kg/hr, or greater, (e.g., 144 µg/kg/hr), wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 50% to about 95% of patients receiving ganaxolone achieve a HAM-D response at about 11 days, whereas only 38% to 39% of patients receiving placebo achieve HAM-D response at about 11 days. In these embodiments, ganaxolone is generally administered via a single intravenous infusion at a dose and rate of greater than 115 µg/kg/hr (e.g., 144 µg/kg/hr), wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 65% to about 95% of patients receiving ganaxolone achieve a HAM-D response at about 34 days, whereas only from 47% to 49% of patients receiving placebo achieve HAM-D response at about 34 days. In these embodiments, ganaxolone is generally administered via a single intravenous infusion at a dose and rate of 75 µg/kg/hr or greater (e.g., 86 µg/kg/hr, 144 µg/kg/hr, etc.), wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

% Remission

Administration of ganaxolone in accordance with the methods of the present invention may result in a greater proportion of patients achieving HAM-D remission, as compared to placebo, at about 6 hours and/or at about 12 hours and/or about 24 hours (about 1 day) and/or about 48 hours (about 2 days) and/or about 60 hours (about 2.5 days) and/or about 72 hours (about 3 days) and/or about 11 days and/or about 30 days and/or about 34 days.

In certain embodiments, from about 22% to about 80% of patients receiving ganaxolone achieve HAM-D remission at about 48 hours, whereas from 18% to 19% of patients receiving placebo achieve HAM-D remission at about 48 hours. In these embodiments, ganaxolone is generally administered at a dose and rate of 75 µg/kg/hr, or greater.

In certain embodiments, from about 34% to about 80% of patients receiving ganaxolone achieve HAM-D remission at about 60 hours, whereas only from 25% to 26% of patients receiving placebo achieve HAM-D remission at about 60 hours. In these embodiments, ganaxolone is generally administered via a single intravenous infusion at a dose and rate of 55 µg/kg/hr or greater than 115 µg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 43% to about 80% of patients receiving ganaxolone achieve a HAM-D remission at about 72 hours, whereas only from 33% to 34% of patients receiving placebo achieve HAM-D remission at about 72 hours. In these embodiments, ganaxolone is generally administered via a single intravenous infusion at a dose and rate of greater than 115 µg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour 12 hours of the infusion. The infusion may be for a time period of from 1 hour to 80 hours.

In certain embodiments, from about 30% to about 80% of patients receiving ganaxolone achieve a HAM-D remission at about 11 days, whereas only from 23% to 24% of patients receiving placebo achieve HAM-D remission at about 11 days. In these embodiments, ganaxolone is generally administered via a single intravenous infusion at a dose and rate of greater than 115 µg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 43% to about 80% of patients receiving ganaxolone achieve a HAM-D remission at about 34 days, whereas only 36% of patients receiving placebo achieve HAM-D remission at about 34 days. In these embodiments, ganaxolone is generally administered via a single intravenous infusion at a dose and rate of greater than 75 µg/kg/hr (e.g., 86 µg/kg/hr, 144 µg/kg/hr, etc.), wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

In certain embodiments, from about 38% to about 80% of patients receiving ganaxolone achieve HAM-D remission at about 60 hours, and remain in remission at about 11 days and about 34 days. In these embodiments, ganaxolone is generally administered via a single intravenous infusion at a dose and rate of greater than 75 µg/kg/hr, wherein from about 70% to about 95% of the dose is administered at a first constant rate (mg/hr) for the first 1 hour to 48 hours of the infusion, and from about 5% to about 30% of the dose is administered at a second constant rate (mg/hr) for the last 1 hour to 12 hours of the infusion. The infusion may be for a time period of from 1 hour to 80 hours.

Stanford Sleepiness Scale

Stanford Sleepiness Scale (SSS) is a simple 8-item self-rated scale measuring level of sleepiness the subject is feeling. Level 1 is "feeling active, vital, alert or wide-awake"; and level 7 is "no longer fighting sleep, sleep onset soon; having dream-like thoughts"; and level 8 is sleeping.

Administration of ganaxolone in accordance with the methods of the present invention, preferably, results in an improvement in SSS level.

Clinical Global Impression-Improvement (CGI-I) and Clinical Global Impression-Severity (CGI-S)

The Clinical Global Impression-Improvement scale (CGI-I) is a 7-point scale that asks the clinician to assess how much the subject's illness has improved or worsened relative to a baseline state at the beginning of the intervention. It is rated as: 1, very much improved; 2, much improved; 3, minimally improved; 4, no change; 5, minimally worse; 6, much worse; or 7, very much worse. The Clinical Global Impression-Severity scale (CGI-S) is a 7-point scale that asks the clinician to rate the severity of the subject's depression at the time of assessment, relative to the clinician's past experience with subjects who have the same diagnosis. Considering total clinical experience, a subject is assessed on the severity of depression at the time of rating 1, normal, not at all ill; 2, borderline mentally ill; 3, mildly ill; 4, moderately ill; 5, markedly ill; 6, severely ill; or 7, extremely ill.

Administration of ganaxolone in accordance with the methods of the present invention, preferably, results in an improvement in CGI-I and CGI-T scores.

In certain embodiments, administration of ganaxolone in accordance with the methods of the present invention provides an improvement in CGI-I score (i.e., LS mean reduction from baseline) at about 12 hours of at least about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 48 hours of at least about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 48 hours of at least about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 60 hours of at least about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 72 hours of at least about 1, about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 11 days of at least about 2, about 3, about 4, about 5, or greater. In the preferred embodiments, the improvement is greater than with the placebo.

In certain embodiments, administration of ganaxolone in accordance with the methods of the present invention provides an improvement in CGI-I score (i.e., LS mean reduction from baseline) at about 34 days of at least about 2, about 3, about 4, about 5, or greater. In the preferred embodiments, the improvement is greater than with the placebo.

Edinburgh Postnatal Depression Scale (EPDS)

The (EPDS) is a 10-question self-rated instrument for assessment symptoms of PPD, such as worry, sleep, mood and enjoyment. Two questions assessing obsessive thoughts are added to this questionnaire ("How much of your time is occupied by obsessive thoughts over the past 24h?" and "How much distress do your obsessive thoughts cause you?"), but they are not counted towards the total score in the statistical analysis. These 2 questions are rated on a 5-point scale.

Administration of ganaxolone in accordance with the methods of the present invention, preferably, results in an improvement in EPDS score.

In certain embodiments, administration of ganaxolone in accordance with the methods of the present invention provides an improvement in EPDS score (i.e., LS mean reduction from baseline) at about 60 hours of at least about 5, about 6, about 7, about 8, about 9, about 10, about 11, about 12, about 13, about 14, about 15, or greater. In the preferred embodiments, the improvement is greater than with the placebo. In these embodiments, ganaxolone is generally administered at a dose and rate of about 115 µg/kg/hr, or greater.

In certain embodiments, administration of ganaxolone in accordance with the methods of the present invention provides an improvement in EPDS score (i.e., LS mean reduction from baseline) at about 11 days of at least about 5, about 6, about 7, about 8, about 9, about 10, about 11, about 12, about 13, about 14, about 15, or greater. In the preferred embodiments, the improvement is greater than with the placebo. In these embodiments, ganaxolone is generally administered at a dose and rate of about 75 µg/kg/hr, or greater.

In certain embodiments, administration of ganaxolone in accordance with the methods of the present invention provides an improvement in EPDS score (i.e., LS mean reduction from baseline) at about 34 days of at least about 5, about 6, about 7, about 8, about 9, about 10, about 11, about 12, about 13, about 14, about 15, or greater. In the preferred embodiments, the improvement is greater than with the placebo. In these embodiments, ganaxolone is generally administered at a dose and rate of about 75 µg/kg/hr, or greater.

Spielberg Trait-State Anxiety Inventory, 6 Item Version

The Spielberg Trait-State Anxiety Inventory, six item version (STAI6) is a short questionnaire evaluating anxiety state. The STAI6 has 6 questions, such as "I feel calm" and "I feel tense," which the subject rates on a scale corresponding to "not at all," "somewhat," "moderately," and "very much."

Administration of ganaxolone in accordance with the methods of the present invention, preferably, results in an improvement in STAI score.

In certain embodiments, administration of ganaxolone in accordance with the methods of the present invention provides an improvement in STAI6 score (i.e., LS mean reduction from baseline) at 12 hours of at least about 5, about 6, about 7, about 8, about 9, about 10, about 11, about 12, about 13, about 15, about 16, about 17, or greater. In the preferred embodiments, the improvement is greater than with the placebo. In these embodiments, ganaxolone is generally administered at a dose and rate of about 75 µg/kg/hr, or greater.

In certain embodiments, administration of ganaxolone in accordance with the methods of the present invention provides an improvement in STAI6 score (i.e., LS mean reduction from baseline) at 24 hours of at least about 5, about 6, about 7, about 8, about 9, about 10, about 11, about 12, about 13, about 15, about 16, about 17, or greater. In the preferred embodiments, the improvement is greater than with the placebo. In these embodiments, ganaxolone is generally administered at a dose and rate of about 86 µg/kg/hr.

In certain embodiments, administration of ganaxolone in accordance with the methods of the present invention provides an improvement in STAI6 score (i.e., LS mean reduction from baseline) at 48 hours of at least about 10, about 11, about 12, about 13, about 14, about 15, about 16, about 17, about 18, about 19, about 20, about 21, or greater. In the preferred embodiments, the improvement is greater than with the placebo. In these embodiments, ganaxolone is generally administered at a dose and rate of about 75 µg/kg/hr, or greater.

In certain embodiments, administration of ganaxolone in accordance with the methods of the present invention provides an improvement in STAI6 score (i.e., LS mean reduction from baseline) at 60 hours of at least about 15, about 16, about 17, about 18, about 19, about 20, about 21, about 22, about 23, about 24, about 25, about 26, or greater. In the preferred embodiments, the improvement is greater than with the placebo. In these embodiments, ganaxolone is generally administered at a dose and rate of about 144 µg/kg/hr, or greater.

In certain embodiments, administration of ganaxolone in accordance with the methods of the present invention provides an improvement in STAI6 score (i.e., LS mean reduction from baseline) at 72 hours of at least about 15, about 16, about 17, about 18, about 19, about 20, about 21, about 22, about 23, about 24, about 25, about 26, or greater. In the preferred embodiments, the improvement is greater than with the placebo. In these embodiments, ganaxolone is generally administered at a dose and rate of about 144 µg/kg/hr, or greater.

In certain embodiments, administration of ganaxolone in accordance with the methods of the present invention provides an improvement in STAI6 score (i.e., LS mean reduction from baseline) at about 11 days of at least about 8, about 10, about 12, about 14, about 16, about 16, about 18, about 20, about 21, about 22, about 23, about 24, or greater. In the preferred embodiments, the improvement is greater than with the placebo. In these embodiments, ganaxolone is generally administered at a dose and rate of about 75 µg/kg/hr, or greater.

In certain embodiments, administration of ganaxolone in accordance with the methods of the present invention provides an improvement in STAI6 score (i.e., LS mean reduction from baseline) at about 34 days of at least about 10, about 12, about 14, about 16, about 16, about 18, about 20, about 21, about 22, about 23, about 24, about 25, about 26, or greater. In the preferred embodiments, the improvement is greater than with the placebo. In these embodiments, ganaxolone is generally administered at a dose and rate of from about 75 µg/kg/hr, or greater.

SAFER Interview

SAFER interview (State versus trait; Assessability; Face validity; Ecological Validity; and Rule of 3 Ps (pervasive, persistent, and pathological)) can be used to confirm validity of the diagnosis of PPD and eligibility for the study from depression perspective.

Columbia Suicide Severity Rating Scale (CSSRS)

The CSSRS is a unique, simple, and short method of assessing both behavior and ideation that tracks all suicidal events, and provides a summary of suicidality. It assesses the lethality of attempts and other features of ideation (frequency, duration, controllability, reasons for ideation, and deterrents) that are significantly predictive of completed suicide.

Administration of ganaxolone in accordance with the methods of the present invention, preferably, results in an improvement in CSSRS score.

Patient

A patient in the methods of the present invention is a female. The female may be, e.g., from about 12 years to about 55 years old, from about 13 years to about 50 years old, from about 13 years to about 45 years old, from about 14 years to about 45 years old, from about 15 years to about 45 years old, from about 16 years to about 45 years old, from about 17 years to about 45 years old, or from about 18 years to about 45 years old.

Treatment may be initiated during third trimester of pregnancy or after the female gives birth.

Treatment may be initiated when the female has HAM-D score of from 10 to 19, which indicates that the female is mildly depressed; HAM-D score of from 20 to 25, which indicates that the female is moderately depressed; or HAM-D score of 26 or greater, which indicates that the female is severely depressed.

Treatment may also be initiated prophylactically, e.g., when allopregnanolone plasma levels drops in the female below about 60 pg/ml, below about 55 pg/ml, below about 50 pg/ml, below about 45 pg/ml, below about 40 pg/ml, below about 35 pg/ml, below about 30 pg/ml, below about 25 pg/ml, below about 20 pg/ml, below about 15 pg/ml, below about 10 pg/ml, or below about 5 pg/ml.

Treatment may also be initiated prophylactically, e.g., when the female exhibits an increase in HAM-D score of 5 or more during the third trimester of pregnancy or after the female gives birth. The increase the HAM-D score may be over a time period of from about 1 week to about 12 months.

Dosage

Ganaxolone is lipophilic and may accumulate in adipose tissue. Thus, in certain embodiments, ganaxolone's dose is based on the female's weight for all or part of the dose regimen, e.g., to account for ganaxolone's distribution to the adipose tissue and ensure adequate exposure to ganaxolone.

The amount of ganaxolone administered to the female per day in the intravenous infusion in the methods of the present invention may range, e.g., from about 150 mg to about 900 mg. For example, 216 mg, 432 mg or 660 mg may be administered parenterally to the female over a time period of from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 60 hours) at a rate of less than about 75 µg/kg/hr, from about 75 µg/kg/hr to about 250 µg/kg/hr, from about 80 µg/kg/hr to about 250 µg/kg/hr, from about 75 µg/kg/hr to about 240 µg/kg/hr, from about 75 µg/kg/hr to about 230 µg/kg/hr, from about 75 µg/kg/hr to about 220 µg/kg/hr, from about 75 µg/kg/hr to about 210 µg/kg/hr, from about 75 µg/kg/hr to about 200 µg/kg/hr, from about 75 µg/kg/hr to about 190 µg/kg/hr, from about 75 µg/kg/hr to about 185 µg/kg/hr, from about 75 µg/kg/hr to about 180 µg/kg/hr, from about 75 µg/kg/hr to about 170 µg/kg/hr, from about 75 µg/kg/hr to about 160 µg/kg/hr, from about 80 µg/kg/hr to about 160 µg/kg/hr, from about 80 µg/kg/hr to about 155

µg/kg/hr, from about 75 µg/kg/hr to about 115 µg/kg/hr, from about 90 µg/kg/hr to about 155 µg/kg/hr, from about 95 µg/kg/hr to about 155 µg/kg/hr, from about 100 µg/kg/hr to about 155 µg/kg/hr, from about 105 µg/kg/hr to about 155 µg/kg/hr, from about 110 µg/kg/hr to about 155 µg/kg/hr, from about 115 µg/kg/hr to about 155 µg/kg/hr, from about 120 µg/kg/hr to about 155 µg/kg/hr, or from about 120 µg/kg/hr to about 150 µg/kg/hr.

If a subject experiences excessive sedation or dizziness during the infusion, the dose of ganaxolone may be adjusted, e.g., by stopping the infusion for a minimum of 1 hour or until the effects resolve and then restarting the infusion at half the rate that caused the sedation or dizziness. For example, if sedation is observed at the rate of 4 mg/hr (16 ml/h), the infusion can be stopped for 1 hour and, then, restarted at 2 mg/hr (8 ml/h).

If the subject experiences excessive sedation or dizziness during the administration of the bolus dose, the dosing may be stopped immediately. After a minimum of 1 hour or when the effects resolve, the intravenous infusion may be started at the doses and rates of less than about 75 µg/kg/hr, from about 75 µg/kg/hr to about 250 µg/kg/hr, from about 80 µg/kg/hr to about 250 µg/kg/hr, from about 75 µg/kg/hr to about 240 µg/kg/hr, from about 75 µg/kg/hr to about 230 µg/kg/hr, from about 75 µg/kg/hr to about 220 µg/kg/hr, from about 75 µg/kg/hr to about 210 µg/kg/hr, from about 75 µg/kg/hr to about 200 µg/kg/hr, from about 75 µg/kg/hr to about 190 µg/kg/hr, from about 75 µg/kg/hr to about 185 µg/kg/hr, from about 75 µg/kg/hr to about 180 µg/kg/hr, from about 75 µg/kg/hr to about 170 µg/kg/hr, from about 75 µg/kg/hr to about 160 µg/kg/hr, from about 80 µg/kg/hr to about 160 µg/kg/hr, from about 80 µg/kg/hr to about 155 µg/kg/hr, from about 75 µg/kg/hr to about 115 µg/kg/hr, from about 90 µg/kg/hr to about 155 µg/kg/hr, from about 95 µg/kg/hr to about 155 µg/kg/hr, from about 100 µg/kg/hr to about 155 µg/kg/hr, from about 105 µg/kg/hr to about 155 µg/kg/hr, from about 110 µg/kg/hr to about 155 µg/kg/hr, from about 115 µg/kg/hr to about 155 µg/kg/hr, from about 120 µg/kg/hr to about 155 µg/kg/hr, or from about 120 µg/kg/hr to about 150 µg/kg/hr.

In certain embodiments, the intravenous infusion of ganaxolone is followed by oral administration of ganaxolone. In these embodiments, ganaxolone may be administered orally with or without food. However, when administered orally, ganaxolone is preferably administered within 15 minutes of a fatty meal or snack (e.g., fatty yogurt, nuts, avocado) and/or with 240 mL (8 oz.) of water at dinner time. The amount of ganaxolone administered orally may range from about 200 mg to about 2000 mg per day. For example, an oral daily dose of ganaxolone may be, e.g., about 200 mg, about 220 mg, about 400 mg, about 440 mg, about 600 mg, about 660 mg, about 800 mg, about 900 mg, or about 1000 mg.

In certain embodiments, the oral dose daily dose of ganaxolone is administered in two, three or four divided doses.

In certain embodiments, the oral daily dose of ganaxolone is administered in two divided doses about 2 hours to about 12 hours, about 2 hours to 10 hours, about 2 hours to about 8 hours, about 2 hours to about 6 hours, about 2 hours to about 5 hours, or about 2 hours to about 4 hours apart. Each dose may independently comprise from about 200 mg to about 1000 mg, from about 200 mg to about 800 of ganaxolone. In some embodiments, both doses are administered within about 6 hours, about 5 hours, about 4 hours, or about 3 hours of bedtime.

The dose of the oral ganaxolone may be adjusted, e.g., by lowering the dose from 900 mg to 675 mg or 450 mg, if the subject experiences adverse effects (e.g., sedation in the morning after the dose).

Treatment Duration

Treatment in according with the methods of present invention may be started during third trimester of pregnancy or after the female gives birth.

The intravenous infusion of ganaxolone in the methods of present invention may be over a time period of from about 1 hour to about 85 hours, from about 2 hours to about 80 hours, from about 3 hours to about 80 hours, from about 4 hours to about 80 hours, from about 5 hours to about 80 hours, from about 6 hours to about 80 hours, from about 8 hours to about 80 hours, from about 10 hours to about 80 hours, from about 12 hours to about 80 hours, from about 18 hours to about 75 hours, from about 24 hours to about 70 hours, from about 48 hours to about 70 hours, or from about 54 hours to about 65 hours (e.g., over about 60 hours). For example, intravenous infusion may be over about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 49 hours, about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, or about 72 hours. In the preferred embodiments, a single intravenous infusion of ganaxolone is sufficient to provide an improvement in the female, as evidenced by, e.g., a decrease in HAM-D score at the end of the treatment period.

In certain embodiments, the intravenous infusion of ganaxolone in the method of the present invention is from about 1 hour to about 24 hours, from about 1.5 hours to about 22 hours, from about 2 hours to about 20 hours, from about 2 hours to about 18 hours, from about 2 hours to about 16 hours, from amount 2 hours to about 14 hours, from about 2 hours to about 12 hours, from about 2 hours to about 10 hours, from about 2 hours to about 8 hours, or from about 2 hours to about 7 hours.

In certain embodiments, the intravenous infusion of ganaxolone in the method of the present invention is from about 2 hours to about 7 hours, from about 2.5 hours to about 7 hours, from about 3 hours to about 7 hours, from about 3.5 hours, to about 6.5 hours, or from about 4 hours to about 6.5 hours.

If necessary however, the treatment may be continued with an oral formulation of ganaxolone for a time period of from about 7 days to about 12 months, from about 7 days to about 11 months, from about 14 days to about 10 months, from about 14 days to about 9 months, from about 14 days to about 8 months, from about 14 days to about 6 months, from about 14 days to about 5 months, from about 14 days to about 4 months, from about 14 days to about 3 months, from about 21 days to about 3 months, from about 21 days to about 2 months, from about 21 days to about 6 weeks, or from about 21 days to about 4 weeks. In these embodiments, from about 450 mg to about 900 mg administered orally (e.g., at dinner time for 28 days). In some of the embodiments, the oral dose of ganaxolone is tapered over 1 to 7 days, 2 to 6 days, or 3 to 5 days, prior to the discontinuation.

In certain embodiments, oral administration of ganaxolone is continued until the female is symptom free and/or has a HAM-D score of seven or less for four weeks.

Formulations

The formulations of the present invention comprise a therapeutically effective amount of ganaxolone to treat one or more symptom(s) of postpartum depression and one or more pharmaceutically acceptable excipient(s).

A formulation for the intravenous infusion is preferably a sterile liquid (e.g., an aqueous liquid encompassing suspensions, solutions and the like). In certain embodiments, IV solution is a sterile 3 mg/ml ganaxolone in Captisol® (Sulfobutylether-β-Cyclodextrin), which may or may not be may be diluted with 0.9% saline.

In certain embodiments, the formulation for the intravenous infusion may be a formulation as described and prepared in Applicant's prior U.S. Patent Publication No. 2017/0258812 (U.S. Ser. No. 15/294,135, filed Oct. 14, 2016), entitled "Injectable Neurosteroid Formulations Containing Nanoparticles," hereby incorporated by reference in its entirety, or a formulation as described and prepared in Applicant's prior U.S. Patent Publication No. 2016/0228454, entitled "Intravenous ganaxolone formulations and methods of use in treating status epilepticus and other seizure disorders," hereby incorporated by reference in its entirety. However, formulations for the intravenous infusion may be prepared in accordance with other methods known to those skilled in the art.

Ganaxolone formulations suitable for parenteral administration in the methods of the present invention may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethyleneglycol, glycerol, cremophor and the like), suitable mixtures thereof, vegetable oils (such as olive oil) and injectable organic esters such as ethyl oleate. Additionally, ganaxolone can be dissolved at concentrations of >1 mg/ml using water soluble beta cyclodextrins (e.g. beta-sulfobutyl-cyclodextrin and 2-hydroxypropylbetacyclodextrin). A particularly suitable cyclodextrin is a substituted-β-cyclodextrin is Captisol®. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

A formulation for oral administration may be an oral solid dosage form (e.g., an oral capsule or tablet) or a liquid (e.g., an oral suspension comprising ganaxolone). In certain embodiments, the oral suspension is administered to the patient via the use of an oral syringe.

In certain embodiments, the liquid formulation of the present invention may be a formulation as described and prepared in Applicant's prior U.S. Pat. No. 8,022,054, entitled "Liquid Ganaxolone Formulations and Methods for the Making and Use Thereof", hereby incorporated by reference in its entirety. However, the oral liquid (e.g., suspension) formulation of ganaxolone may be prepared in accordance with other methods known to those skilled in the art.

As described in U.S. Pat. No. 8,022,054, the liquid formulation may be an aqueous dispersion of stabilized particles comprising ganaxolone, a hydrophilic polymer, a wetting agent, and an effective amount of a complexing agent that stabilizes particle growth after an initial particle growth and endpoint is reached, the complexing agent selected from the group of small organic molecules having a molecular weight less than 550 and containing a moiety selected from the group consisting of a phenol moiety, an aromatic ester moiety and an aromatic acid moiety, wherein the stabilized particles have a volume weighted median diameter (D50) of the particles from about 50 nm to about 500 nm, the complexing agent being present in an amount from about 0.05% to about 5%, w/w based on the weight of particles, the particles dispersed in an aqueous solution which further contains at least two preservatives in an amount sufficient to inhibit microbial growth. The hydrophilic polymer may be in an amount from about 3% to about 50%, w/w, based on the weight of the solid particles. The wetting agent may be an amount from about 0.01% to about 10%, w/w, based on the weight of the solid particles. The pregnenolone neurosteroid (e.g., ganaxolone) may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropylmethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. The aqueous dispersion may further comprise a sweetener, e.g., sucralose. The preservative is selected from the group consisting of potassium sorbate, methylparaben, propylparaben, benzoic add, butylparaben, ethyl alcohol, benzyl alcohol, phenol, benzalkonium chloride, and mixtures of any of the foregoing.

In some embodiments, liquid ganaxolone formulations are provided comprising the ganaxolone particles described herein and at least one dispersing agent or suspending agent for oral administration to a subject. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments the aqueous dispersion or suspension is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of pregnenolone neurosteroid (e.g., ganaxolone) at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, ganaxolone formulations are powders for aqueous dispersion and comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid ganaxolone formulation for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, $2^{nd}$ Ed., pp. 754-757 (2002). In addition to ganaxolone particles, the liquid dosage forms may comprise additives, such as: (a) disintegrating agents, (b) dispersing agents; (c) wetting agents; (d) at least one preservative, (e) viscosity enhancing agents, (f) at least one sweetening agent, (g) at least one flavoring agent, (h) a complexing agent. and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide), and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet), maltol, mannitol, maple, marshmallow, menthol, mint cream, mixed berry, neohesperidine DC, neotame, orange, pear, peach, peppermint, peppermint cream, Prosweet®. Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid ganaxolone formulations can also comprise inert diluents commonly used in the art, such as water or other solvents, solubilizing agents, and emulsifiers.

In some embodiments, the ganaxolone formulations can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960,563, each of which is specifically incorporated by reference.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In certain preferred embodiments, the liquid pharmaceutical formulation comprising ganaxolone, hydroxypropyl methylcellulose, polyvinyl alcohol, sodium lauryl sulfate, simethicone, methyl paraben, propyl paraben, sodium benzoate, citric acid, and sodium citrate at pH 3.8-4.2. The suspension may comprise ganaxolone at a concentration of 50 mg/ml. The formulation may further comprise a pharmaceutically acceptable sweetener (e.g., sucralose) and/or a pharmaceutically acceptable flavorant (e.g., cherry). The formulation may be enclosed, e.g., in a 120 mL, 180 mL, 240 mL, or 480 mL bottle.

In certain preferred embodiments, the oral solid formulation of the present invention may be a formulation as described and prepared in Applicant's prior U.S. Pat. No. 7,858,609, entitled "Solid Ganaxolone Formulations and Methods for the Making and Use Thereof", hereby incorporated by reference in its entirety. However, the oral solid dosage formulation of ganaxolone may be prepared in accordance with other methods known to those skilled in the art.

For example, as disclosed in U.S. Pat. No. 7,858,609, the oral solid formulation may comprise stabilized particles comprising ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm, the complexing agent being present in an amount from about 0.05% to about 5% w/w, based on the weight particles of the solid. The hydrophilic polymer may be in an amount from about 3% to about 50%, w/w, based on the weight of the solid particles. The wetting agent may be an amount from about 0.01% to about 10%, w/w, based on the weight of the solid particles. Ganaxolone may be in an amount from about 10% to about 80% (and in certain embodiments form about 50% to about 80%) based on the weight of the stabilized particles. The stabilized particles may exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm. The stabilized particles may exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SW is less than about 750 nm. The solid stabilized particles may be combined with optional excipients and prepared for administration in the form of a powder, or they may be incorporated into a dosage form selected from the group consisting of a tablet or capsule. The complexing agent may be a paraben, benzoic acid, phenol, sodium benzoate, methyl anthranilate, and the like. The hydrophilic polymer may be a cellulosic polymer, a vinyl polymer and mixtures thereof. The cellulosic polymer may be a cellulose ether, e.g., hydroxypropylmethylcellulose. The vinyl polymer may be polyvinyl alcohol, e.g., vinyl pyrrolidone/vinyl acetate copolymer (S630). The wetting agent may be sodium lauryl sulfate, a pharmaceutically acceptable salt of docusate, and mixtures thereof. When the particles are incorporated into a solid dosage form, the solid dosage form may further comprise at least one pharmaceutically acceptable excipient, e.g., an ionic dispersion modulator, a water soluble spacer, a disintegrant, a binder, a surfactant, a plasticizer, a lubricant, a diluent and any combinations or mixtures thereof. The water soluble spacer may be a saccharides or an ammonium salt, e.g., fructose, sucrose, glucose, lactose, mannitol. The surfactant may be, e.g., polysorbate. The plasticizer may be, e.g., polyethylene glycol. The disintegrant may be cross-linked sodium carboxymethylcellulose, crospovidone, mixtures thereof, and the like.

A capsule may be prepared, e.g., by placing the bulk blend ganaxolone formulation, described herein, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the ganaxolone formulation is delivered in a capsule form.

In certain embodiments, each capsule contains either 200 mg or 225 mg ganaxolone, and hydroxypropyl methylcellulose, sucrose, polyethylene glycol 3350, polyethylene glycol 400, sodium lauryl sulfate, sodium benzoate, citric acid anhydrous, sodium methyl paraben, microcrystalline cellulose, 30% Simethicone Emulsion, gelatin capsules, polysorbate 80, and sodium chloride. In some of the embodiments, the size of the capsule is 00.

Alternatively, the oral dosage forms of the present invention may be in the form of a controlled release dosage form, as described in U.S. Pat. No. 7,858,609, herein incorporated by reference.

Oral dosage forms described in U.S. application Ser. No. 16/185,677, entitled "GANAXOLONE FOR USE IN TREATING GENETIC EPILEPTIC DISORDERS", filed on Nov. 9, 2018, herein incorporated by reference, may also be used in the methods of present invention.

Combination Treatment

The disclosure includes embodiments in which ganaxolone is the only active agent and embodiments in which ganaxolone is administered in combination with one or more additional active agents. Ganaxolone may be administered while the additional active agent (concurrent administration) or may be administered before or after the additional active agent is administered (sequential administration).

The disclosure includes embodiments in which the additional active agent is a benzodiazepine, a selective serotonin reuptake inhibitors ("SSRIs") and/or serotonin and norepinephrine reuptake inhibitors (SNRIs).

SSRIs include, e.g., citalopram, escitalopram, fluoxetine, paroxetine, sertraline, ilazodone.

SNRIs include, e.g., desvenlafaxine, duloxetine, levomilnacipran, and venlafaxine.

Benzodiazepines include, e.g., alprazolam, bretazenil, bromazepam, brotizolam, chloridazepoxide, cinolazepam, clonazepam, chorazepate, clopazam, clotiazepam, cloxazolam, delorazepam, diazepam, estazolam, etizolam, ethyl loflazepate, flunitrazepam, flurazepam, flutoprazepam, halazepam, ketazolam, loprazolam, lorazepam, lormetazepam, medazepam, midazolam, nimetazeparn, nitrazepam, nordazepam, oxazepam, phenenazepam, pinazepam, prazepam, premazepam, pyrazolam, quazepam, temazepam, tatrazepam, and triazolam.

In certain embodiments, ganaxolone may be administered concurrently or sequentially with diphenhydramine (25 mg to 50 mg) and/or trazodone (25 mg to 50 mg) and/or doxepin (3 mg to 5 mg) and/or quetiapine (50 mg) and/or aripiprazole (15 mg).

DETAILED DESCRIPTION OF PREFERRED EMBODIMENTS

The following examples of formulations in accordance with the present invention are not to be construed as limiting the present invention in any manner and are only samples of the various formulations described herein.

Example 1 (Dose Justification)

A Phase 1 study in healthy volunteers investigating the safety of IV ganaxolone, infusion of 30 mg/hr for 1 hour, 20 mg over 2 minutes and 20 mg/hr for 4 hours led to peak concentrations of 258, 441 and 215 ng/mL, respectively, without any safety concerns. Sedation was assessed using the Modified Observers Assessment of Alertness/Sedation (MOAAS) scale. On this scale, score 5 indicates no sedation (responds readily to name spoken in normal tone) while score 1 indicates deep sedation (responds only after painful trapezius squeeze). In these cohorts, vast majority of the scores were 5 with few exceptions of 4 (lethargic response to name spoken in normal tone) and 3 (responds only after name is called loudly or repeatedly). The sedation scores reversed quickly after the infusion was stopped. The highest bolus dose tested was 30 mg, which was infused over 5-minutes. This dose led to peak concentration levels (Cmax) of >1,000 ng/mL with no safety concerns (except sedation).

Six subjects reported treatment emergent AEs. No single AE was seen twice. Only one event, headache, was considered by the investigator to be related to ganaxolone. None of the treatment emergent AEs were serious, and all were of mild intensity. No clinically meaningful mean changes in laboratory test results, vital signs, or ECG parameters occurred in any cohort.

Example 2

A Phase 2A, Double-Blind, Placebo-Controlled, Multiple-Dose Escalation Study to Evaluate Safety, Pharmacokinetics and Efficacy of Intravenously and Orally Administered Ganaxolone in Women with Postpartum Depression An objective of the study is to assess the safety and tolerability of escalating doses of intravenously and orally administered ganaxolone as determined by adverse events and changes from baseline in laboratory measures, vital signs, Columbia Suicide Severity Rating Scale (CSSRS), electrocardiogram (ECG), Stanford Sleepiness Scale (SSS), and physical examination.

Another objective of the study is to explore the efficacy of escalating doses of intravenously and orally administered ganaxolone in the treatment of PPD with the Hamilton Depression Rating Scale 17-item version (HAM-D17), Edinburgh Postnatal Depression Scale (EPDS), Spielberger State-Trait Anxiety Inventory 6-item version (STAI6) and Clinical Global Impression-Improvement (CGI-I) scale.

Approximately 200 women with PPD 18 to 45 years of age are screened to randomize up to 100 subjects across up to 6 cohorts. Approximately 10-30 subjects are randomized into each cohort. Randomized subjects receive the investigational product (IP), ganaxolone or matching placebo in a 1:1 ratio. In Cohorts 1-5 the IP is administered intravenously over 60 hours. In Cohort 6 the dosing is initiated with a 6-hour intravenous (IV) infusion followed by oral dosing for 28 days plus 3-day taper.

The screening period for each cohort is up to 2 weeks. In Cohorts 1-5 the screening period is followed by a 60-hour infusion treatment with or without initial bolus dosing during the 4-day inpatient treatment phase at a hospital or clinical pharmacology unit. The subjects are discharged from the unit on the morning of Day-4. There are 2 safety follow-up visits after inpatient discharge on post-treatment Weeks 1 and 4. The total duration of the study is up to 7 weeks for Cohorts 1-5. For Cohort 6 there is an initial infusion treatment and oral dose during the approximately 24-hour inpatient dosing phase followed by 27 days of oral treatment as outpatient. There are 3 safety follow-up visits after the outpatient treatment period on posttreatment Weeks 1, 4, and 6. The total duration of the study is up to 12 weeks for subjects participating in Cohort 6.

The goal of Cohorts 1-6 is to determine safety, tolerability, PK and efficacy of the IV formulation (and in Cohort 6, the IV formulation followed by oral formulation) of ganaxolone in PPD subjects administered at a predicted dose regimen mimicking the levels of allopregnanolone at the end of pregnancy, or higher.

Cohort 1

Ganaxolone is infused at a rate of 4 mg/hr (16 ml/h of ganaxolone 0.25 mg/ml solution) for 48 hours and then, to minimize any risks for withdrawal or rebound of anxiety and depression symptoms, at a rate of 2 mg/hr for the next 12 hours. The infusion is stopped at 60 hours. Total of 9 subjects are dosed for this cohort. There are no serious adverse events or adverse events leading to discontinuation, and no subject needed a dose adjustment.

The targeted ganaxolone plasma concentration at steady state (Css) in this cohort is 52 ng/ml, which is estimated to be achieved with a ganaxolone infusion rate of 4 mg/hr (16 ml/h of ganaxolone 0.25 mg/ml solution). Steady state is expected to be achieved within 24 hours. The target ganaxolone exposure level of approximately 52 ng/ml for Cohort 1 is chosen to achieve a level similar to that of allopregnanolone at the end of pregnancy. Allopregnanolone levels increase gradually throughout pregnancy reaching a peak mean concentration at the end of pregnancy of about 15 to 60 ng/ml. The levels then drop precipitously after the delivery. It was hypothesized that substitution of the low allopregnanolone levels with ganaxolone would alleviate or reverse the symptoms of postpartum depression.

Cohort 2

Ganaxolone is infused at a rate of 8 mg/hr (16 ml/h of ganaxolone 0.5 mg/ml solution) for 48 hours and then at a rate of 4 mg/hr for the next 12 hours. This dose is approximately double the expected plasma exposure as compared to Cohort 1 at steady state (Cohort 2 expected plasma concentration ~100-120 ng/mL). The infusion is stopped at 60 hours.

Cohort 3

Twelve mg bolus of ganaxolone is initially given over 2 minutes followed by ganaxolone infusion at a rate of 12 mg/hr (24 ml/h of ganaxolone 0.5 mg/ml solution) for 48 hours. The rate is then reduced to 6 mg/hr for the next 12 hours, which is done to minimize any risks for withdrawal or rebound of anxiety and depression symptoms. The infusion is stopped at 60 hours.

This dose increases the expected maximum plasma exposure by about 1.5-fold as compared to Cohort 2 at steady state during the infusion. The expected maximum plasma concentrations is about 180 ng/ml during the infusion. During the initial 2-minute ganaxolone bolus, the peak plasma concentrations are expected to increase up to 300 ng/ml transiently, and then fall rapidly below 100 ng/ml after the bolus dose is completed.

The bolus dose is justified to provide a rapid loading dose of ganaxolone, which is hypothesized to expedite the onset of antidepressant activity. Based on prior studies with the oral formulation and results from Phase 1 in healthy volunteers using the IV formulation of ganaxolone, the Cohort 3 dose and associated plasma exposure is expected to be generally safe and well tolerated.

The doses administered and plasma concentrations obtained in Cohorts 1-3 are provided in Table 1A below:

TABLE 1A

| Cohort | Subject | WEIGHT (kg) | Dose (µg/hr/kg) | Time(hr): 12 | 24 | 48 | 72 |
|---|---|---|---|---|---|---|---|
| | | | | GNX Concentration (ng/mL) | | | |
| 1 | 102-109 | 82.8 | 48.3 | 61.6 | 59 | 68.7 | 8.97 |
| 1 | 104-101 | 82.9 | 48.3 | 43.7 | 52.7 | 69.9 | 10.8 |
| 1 | 104-117 | 86.8 | 46.1 | 40.6 | 53.8 | 63.5 | 9.32 |
| 1 | 107-111 | 57.7 | 69.3 | 65.7 | 80.8 | 78.9 | 12.5 |
| 1 | 112-116 | 67.1 | 59.6 | 58.8 | 72.6 | 78.1 | 10.1 |
| 2 | 107-225 | 92.8 | 86.2 | 107 | 125 | 120 | 27.1 |
| 2 | 112-246 | 83.5 | 95.8 | 70.8 | 92 | 136 | 26.4 |
| 2 | 112-262 | 87.5 | 91.4 | 111 | 140 | 102 | 30.1 |
| 2 | 114-248 | 50 | 160.0 | 150 | 45.5 | 197 | 28.2 |
| 2 | 116-237 | 67 | 119.4 | 107 | 75.7 | 120 | 11.9 |
| 2 | 116-240 | 84.5 | 94.7 | 115 | 106 | 92 | 23.9 |
| 2 | 116-244 | 109.4 | 73.1 | 63.3 | 96.5 | 77.8 | 23.1 |
| 2 | 116-247 | 88 | 90.9 | 69.3 | 1590* | 73.9 | 26.8 |
| 2 | 116-254 | 74.2 | 107.8 | 116 | 142 | 118 | 25.6 |
| 2 | 116-259 | 85.7 | 93.3 | 49.5 | 80.6 | 73.1 | 19.4 |
| 2 | 116-266 | 62.3 | 128.4 | 146 | 175 | 131 | 46.2 |
| 2 | 116-267 | 47.3 | 169.1 | 183 | 174 | 298 | 26.9 |
| 2 | 116-268 | 47.3 | 169.1 | 140 | 162 | 132 | 21.5 |
| 2 | 117-251 | 99.9 | 80.1 | 71.5 | 89.3 | 93.6 | 18.1 |
| 2 | 117-253 | 100.3 | 79.8 | 77.6 | 26100* | 7390* | 27.5 |
| 3 | 108-395 | 85.1 | 141.0 | 137 | 164 | 207 | 49.3 |
| 3 | 112-393 | 98.6 | 121.7 | 100 | 125 | 146 | 26.1 |
| 3 | 114-369 | 90.6 | 132.5 | 106 | 148 | 212 | 30 |
| 3 | 116-374 | 98.9 | 121.3 | 118 | 163 | 66.4 | 46.2 |
| 3 | 116-377 | 88.6 | 135.4 | 138 | 165 | 211 | 44.6 |
| 3 | 116-379 | 44.8 | 267.9 | 230 | 254 | 213 | 42.8 |
| 3 | 116-380 | 76.4 | 157.1 | 126 | 144 | 4160* | 30.2 |
| 3 | 116-388 | 70.9 | 169.3 | 204 | 250 | 209 | 31.7 |
| 3 | 117-381 | 118.6 | 101.2 | 61.1 | 56 | 85 | 17.5 |
| 3 | 117-384 | 100.7 | 119.2 | | 16 | | 15.2 |

*erroneous measurement

Ratios of ganaxolone plasma concentrations to the ganaxolone doses calculated from the measured ganaxolone plasma concentraations. Erroneous measurements (*) were excluded for the purposes of these calculations. The calculated ratios are provided in Table 1B below.

TABLE 1B

| Time hrs | | | |
|---|---|---|---|
| 12 | 24 | 48 | 72 |
| GNX Concentration (ng/mL)/(µg/hr/kg) | | | |
| 1.28 | 1.22 | 1.42 | 0.19 |
| 0.91 | 1.09 | 1.45 | 0.22 |
| 0.88 | 1.17 | 1.38 | 0.20 |
| 0.95 | 1.17 | 1.14 | 0.18 |
| 0.99 | 1.22 | 1.31 | 0.17 |
| 1.24 | 1.45 | 1.39 | 0.31 |
| 0.74 | 0.96 | 1.42 | 0.28 |
| 1.21 | 1.53 | 1.12 | 0.33 |
| 0.94 | 0.28 | 1.23 | 0.18 |
| 0.90 | 0.63 | 1.01 | 0.10 |
| 1.21 | 1.12 | 0.97 | 0.25 |
| 0.87 | 1.32 | 1.06 | 0.32 |
| 0.76 | | 0.81 | 0.29 |
| 1.08 | 1.32 | 1.09 | 0.24 |
| 0.53 | 0.86 | 0.78 | 0.21 |
| 1.14 | 1.36 | 1.02 | 0.36 |
| 1.08 | 1.03 | 1.76 | 0.16 |
| 0.83 | 0.96 | 0.78 | 0.13 |
| 0.89 | 1.12 | 1.17 | 0.23 |
| 0.97 | | | 0.34 |
| 0.97 | 1.16 | 1.47 | 0.35 |
| 0.82 | 1.03 | 1.20 | 0.21 |
| 0.80 | 1.12 | 1.60 | 0.23 |
| 0.97 | 1.34 | 0.55 | 0.38 |
| 1.02 | 1.22 | 1.56 | 0.33 |
| 0.86 | 0.95 | 0.80 | 0.16 |
| 0.80 | 0.92 | | 0.19 |
| 1.21 | 1.48 | 1.23 | 0.19 |
| 0.60 | 0.55 | 0.84 | 0.17 |
| | | 0.13 | 0.13 |
| Mean (ng/mL)/(µg*hr/kg) 0.946 | 1.061 | 1.169 | 0.234 |

Mean average ganaxolone plasma concentrations provided by administration of ganaxolone doses of 86 µg/kg/hr, 150 µg/kg/hr, 160 µg/kg/hr, 170 µg/kg/hr, 180 µg/kg/hr, 190 µg/kg/hr, 200 µg/kg/hr, 210 µg/kg/hr, 220 µg/kg/hr, and 260 µg/kg/hr were calculated for 12 hours, 24 hours, 48 hours, and overall (12, 24 and 48 hours) were calculated. The mean average plasma concentrations are provided in Table 1C below.

TABLE 1C

| Dose µg/kg/hr | GNX Concentration (ng/mL) Time (hr): | | | |
|---|---|---|---|---|
| | 12 | 24 | 48 | Overall |
| 86 | 81.4 | 91.2 | 100.5 | 91 |
| 150 | 141.9 | 159.1 | 175.3 | 159 |
| 160 | 151.4 | 169.8 | 187.0 | 169 |
| 170 | 160.9 | 180.4 | 198.7 | 180 |
| 180 | 170.3 | 191.0 | 210.4 | 191 |
| 190 | 179.8 | 201.6 | 222.1 | 201 |
| 200 | 189.2 | 212.2 | 233.8 | 212 |
| 210 | 198.7 | 222.8 | 245.5 | 222 |
| 220 | 208.2 | 233.4 | 257.2 | 233 |
| 260 | 246.0 | 275.9 | 303.9 | 275 |

$AUC_{12\text{-}24}$ and $AUC_{24\text{-}48}$ were then calculated by multiplying the average of the two concentrations (e.g., 12 and 24 hours) by their time difference (e.g., 12 hours for the AUC12-24); and $AUC_{12\text{-}48}$ was calculated by adding $AUC_{12-24}$ and $AUC_{24-48}$. The calculated $AUC_{12-24}$, $AUC_{24-48}$ and $AUC_{12-48}$ are provided in Table 1D below.

TABLE 1D

| $AUC_{12-24}$ (ng*hr/ml) | $AUC_{24-48}$ (ng*hr/ml) | $AUC_{12-48}$ (ng*hr/ml) |
| --- | --- | --- |
| 1035.6 | 2301.6 | 3337.2 |
| 1806 | 4012.8 | 5818.8 |
| 1927.2 | 4281.6 | 6208.8 |
| 2047.2 | 4548 | 6595.2 |
| 2167.2 | 4816.8 | 6984 |
| 2288.4 | 5083.2 | 7371.6 |
| 2408.4 | 5352 | 7760.4 |
| 2529.6 | 5618.4 | 8148 |
| 2649.6 | 5887.2 | 8536.8 |
| 3130.8 | 6957.6 | 10088.4 |

Cohorts 4-5

Ganaxolone is infused at a rate of 16 mg over 2 minutes, or less, and the maximum infusion rate does not exceed 16 mg/hr (not including any ganaxolone given by bolus).

Cohort 6

For Cohort 6, the goal of initiation of treatment with IV infusion followed by oral capsules is to maximize the speed of onset of antidepressant activity while providing the convenience of oral dosing for the remainder of the treatment period.

In this cohort dosing is initiated with ganaxolone infusion at a rate of 20 mg/hr (40 ml/h of ganaxolone 0.5 mg/ml solution or matching placebo) for 6 hours followed by ganaxolone 900 mg (four 225 mg capsules per dose) or matching placebo capsules given orally at dinner time for 28 days followed by a 3-day taper (three, two, and one 225 mg capsule(s) per day, respectively).

This initial infusion is targeted to provide a fast onset of antidepressant activity by delivery of rapid plasma exposures to ganaxolone. Then, at dinner time of Day 1 the subjects take their first oral dose of ganaxolone 900 mg (four 225 mg capsules) or matching placebo (4 capsules). This dose is expected to provide mean Cmax plasma concentrations of approximately 250-300 ng/mL and mean steady state levels between 90 and 150 ng/mL, which may be mildly sedating. In previous studies, ganaxolone has been given up to a daily dose of 2000 mg, and at single doses of 1000 mg. Based on the previous experience this dose is expected to be safe.

At subsequent nights (Days 2-28), the target ganaxolone dose is 900 mg or matching placebo (4 225 mg capsules) or oral ganaxolone suspension at dinner time followed by a 3-day taper (e.g., 3, 2, and 1 capsule/s per day, respectively). However, based on the assessment of the investigator the dose may be maintained at 675 mg or 450 mg (or matching placebo) in case of adverse events, such as grogginess in the morning. In the case of 3 capsules per day on day 28 the taper consists of 2, 2, and 1 capsule/s on days 29, 30, and 31, respectively. In the case of 2 capsules per day on day 28 the taper consists of 1 capsule on days 29, 30, and 31. If the subject cannot tolerate 450 mg (or matching placebo) per dose the investigator contacts the Medical Monitor to discuss dosing options.

Subjects randomized to placebo will receive an initial infusion with matching IV placebo (at 40 ml/hr) followed by matching oral placebo (four 225 mg capsules per dose) for 28 days followed by a 3-day taper (three, two, and one 225 mg capsule(s) per day, respectively). The placebo infusion and placebo capsules are identical to the ganaxolone infusion and ganaxolone capsules, respectively, in their appearance.

Pharmacokinetics

Six samples are collected for pharmacokinetic analysis in Cohorts 1-5 and 12 samples in Cohort 6. Maximal plasma concentration (Cmax), concentration at steady-state (Css, determined by the mean concentrations once steady-state is achieved by visual inspection), $AUC_{0-24}$ (calculated as Css multiplied by 24 hours) is estimated. Seven samples are collected during the inpatient phase of Cohort 6 (including 6 samples on Day 1) followed by collection of 5 samples during the outpatient phase during the study visits for a total of 12 samples in Cohort 6.

The following pharmacokinetics parameters are estimated for each subject receiving ganaxolone, if sufficient data are available: Maximal plasma concentration (Cmax), concentration at steady-state (Css, determined by the mean concentrations once steady-state is achieved by visual inspection), $AUC_{0-24}$ (calculated as Css multiplied by 24 hours). PK samples are collected from subjects participating in Cohort 6 after the IV infusion, before and during the oral dosing portion of the study.

Efficacy Analyses

Primary Endpoint

The primary efficacy endpoint is HAM-D17 total score change from baseline to 60 hours post-infusion (on Day 3) for Cohorts 1-3 and to Day 29 for Cohort 6. The primary analysis in each cohort is done using the mITT set. Although the trial is not powered for inferential analysis and there is no consideration for control of type 1 error across multiple cohorts, a clinically meaningful numeric difference in means of 3-4 points, based on mITT analysis, between ganaxalone and placebo treatment groups is considered an indication of acceptable efficacy and is be the most influential outcome in the overall assessment of the efficacy of ganaxolone in treating PPD.

Secondary Endpoints

The trial also evaluates the following secondary endpoints at each post-baseline data collection time point to provide additional evidence of the efficacy of ganaxolone in treating PPD:

Change from baseline in HAM-D17 total score other than at 60 hours post-infusion (on Day 3) for Cohorts 1-3 and to Day 29 for Cohort 6

Change from baseline in EPDS total score

Change from baseline in STAI6

CGI-I.

Exploratory Endpoints

Several endpoints are evaluated for signals of efficacy to explore whether any should be elevated in importance in subsequent trials. Change from baseline to each post-baseline data collection time point is summarized for the following exploratory endpoints:

HAM-D6 (Bech) subscale of HAM-D17: depressed mood, feelings of guilt, work and activities, retardation, anxiety psychic, and general somatic symptoms (Items 1, 2, 7, 8, 10, 13)

Anxiety/Somatization subscale of HAM-D17: anxiety psychic, anxiety somatic, somatic symptoms gastrointestinal, general somatic symptoms, hypochondriasis, and insight (Items 10-13, 15, 17)

Gibbons Global Depression Severity subscale of HAM-D17: depressed mood, feelings of guilt, suicide, work and activities, agitation, anxiety psychic, anxiety somatic, genital symptoms (Items 1-3, 7, 9-11, 14)

HAM-D17 individual items

Anxiety subscale derived from EPDS Items 3-5 ("I have blamed myself unnecessarily when things went wrong," "I have been anxious or worried for no good reason," "I have felt scared or panicky for no very good reason")

EPDS individual items

HAM-D6

The 6-item version of this scale, known as HAM-D6, is derived and used as an additional measure of changes in symptoms of depression. The items on the HAM-D6 scale are as follows: depressed mood, work and interests, general somatic symptoms (tiredness), anxiety, guilt feelings, and psychomotor retardation. Both HAM-D6 and HAM-D17 have been validated and used in many clinical trials of antidepressant medications. The use of the 6-item scale is justified because many items on the 17-item version cannot be expected to change over short period of time (e.g. weight or sleep).

Results for Cohort 6

Figure 23B:
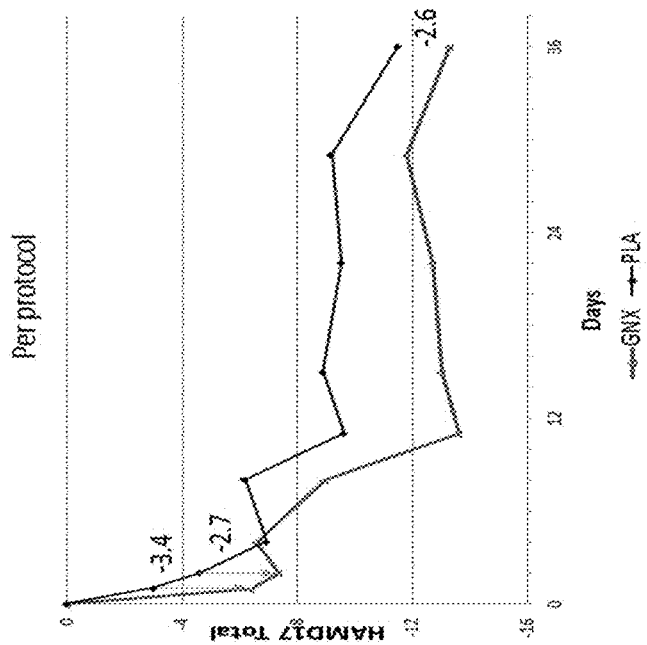
FIG. 23B depicts per protocol HAMD17 (LS Mean) for Cohort 6.
Figure 23A:
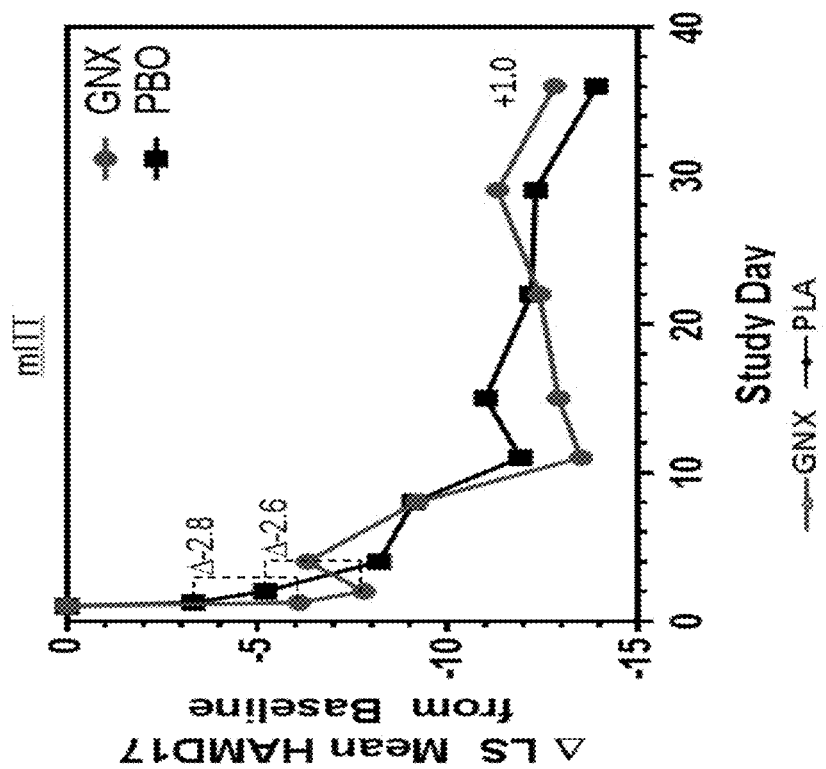
FIG. 23A depicts mITT HAM-D17 (LS Mean) from baseline for Cohort 6.
Figures 24A, 24B:
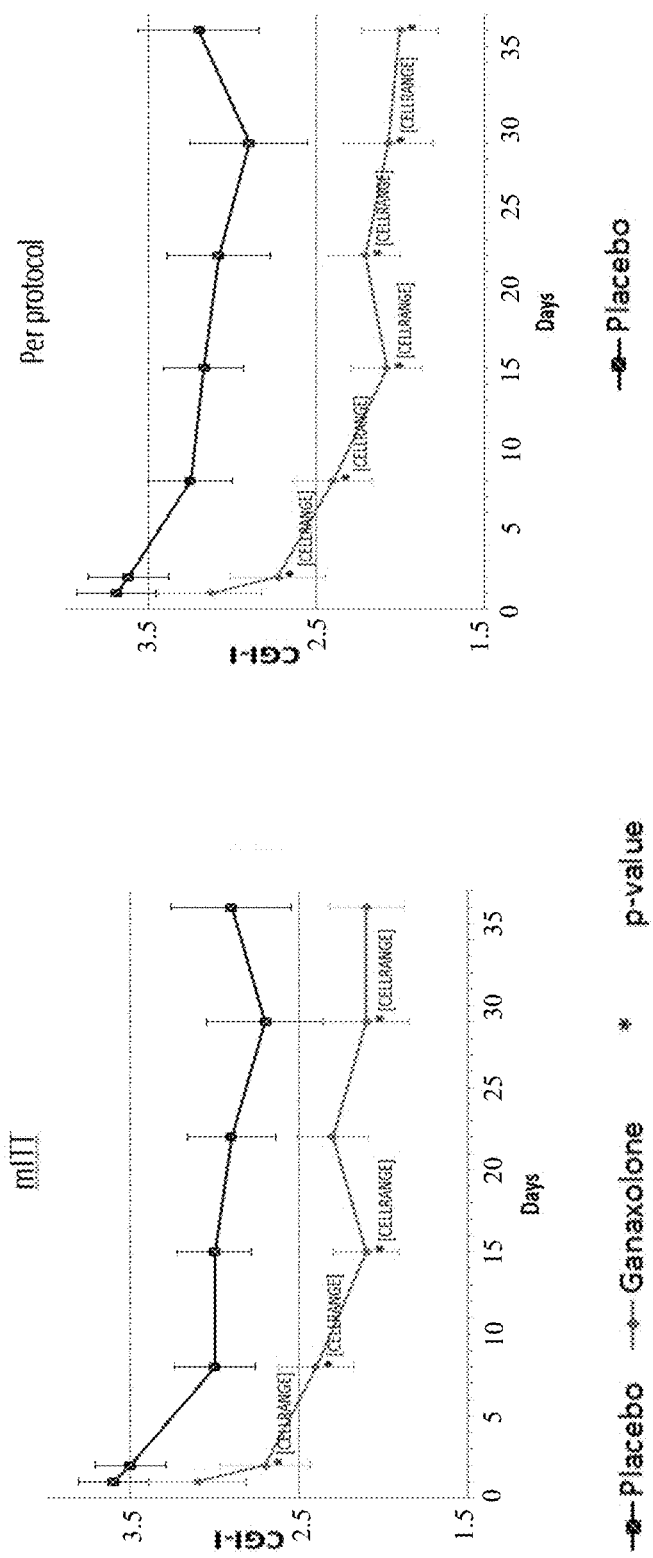
FIG. 24A depicts mITT CGI-I (LS Mean) from baseline for Cohort 6.
FIG. 24B depicts per protocol CGI-I (LS Mean) from baseline for Cohort 6.
Figure 25:
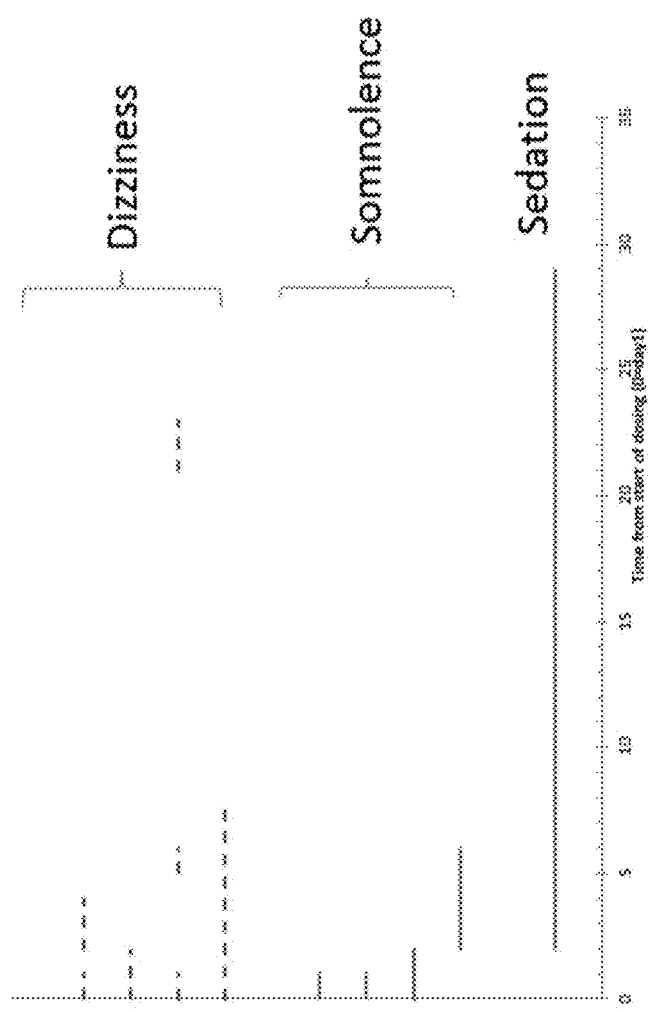
FIG. 25 depicts temporal relationship between treatment and special AEs (Sedation, Somnolence, and Dizziness) for Cohort 6.
Figure 26:
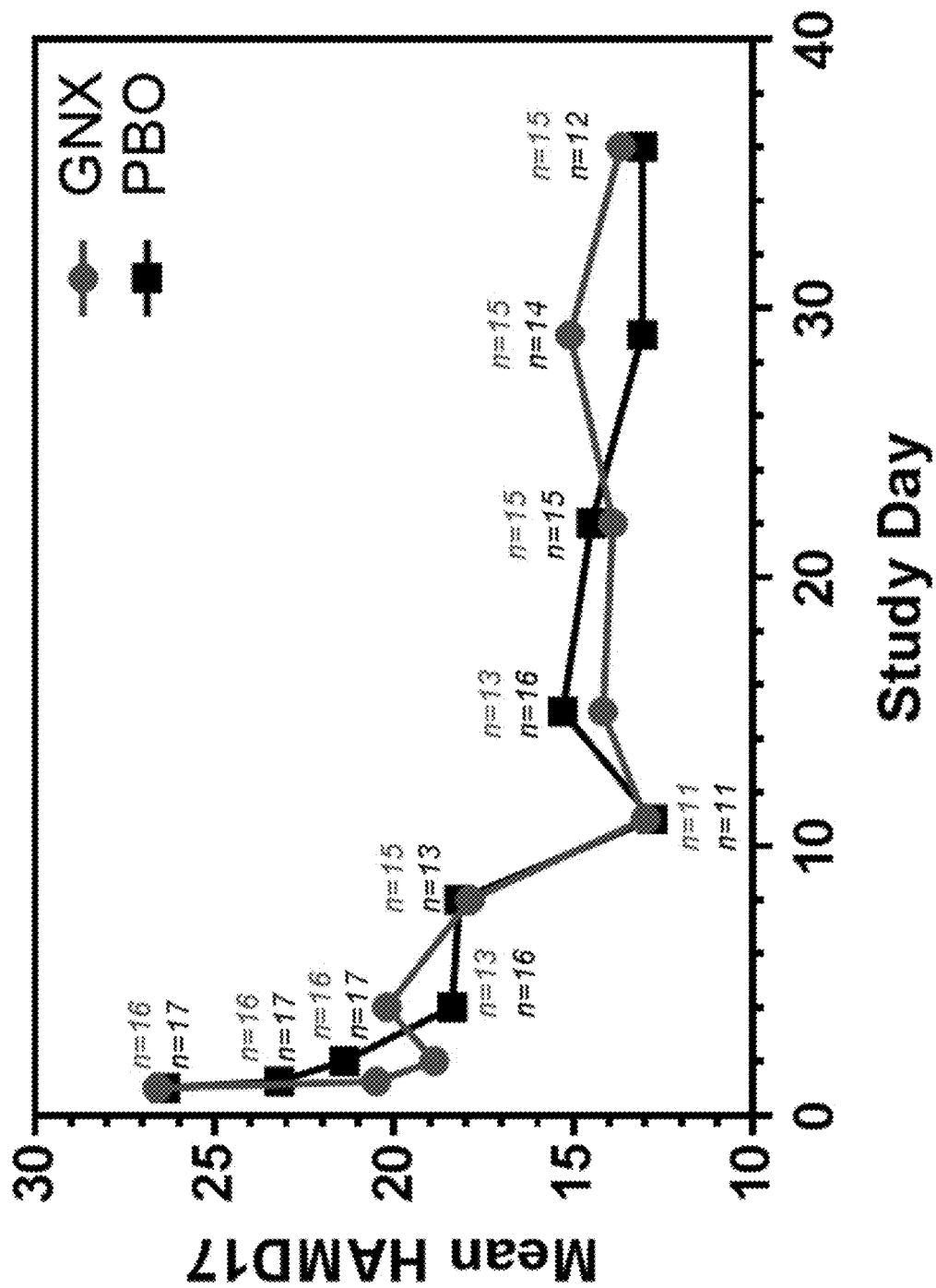
FIG. 26 depicts Mean HAM-D17 scores for Cohort 6.
Figure 27:
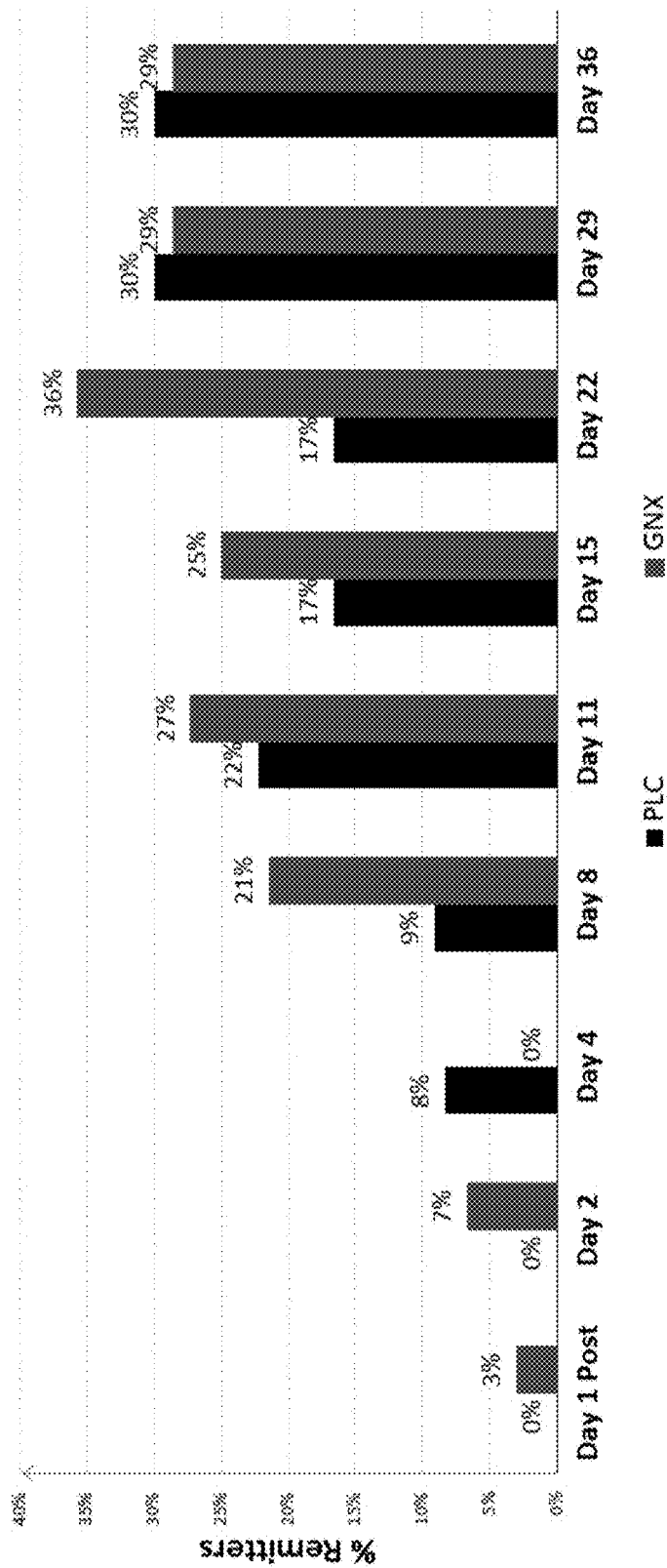
FIG. 27 depicts HAMD17 remission rates per protocol population, and excluding patient 112-699, for Cohort 6. Patient 112-699 was excluded for not complying with the protocol, for example, missing 18 capsules of medication and screening positive (urine) for a prohibitied concomitant medication (benzodiazepine).
Figure 28:
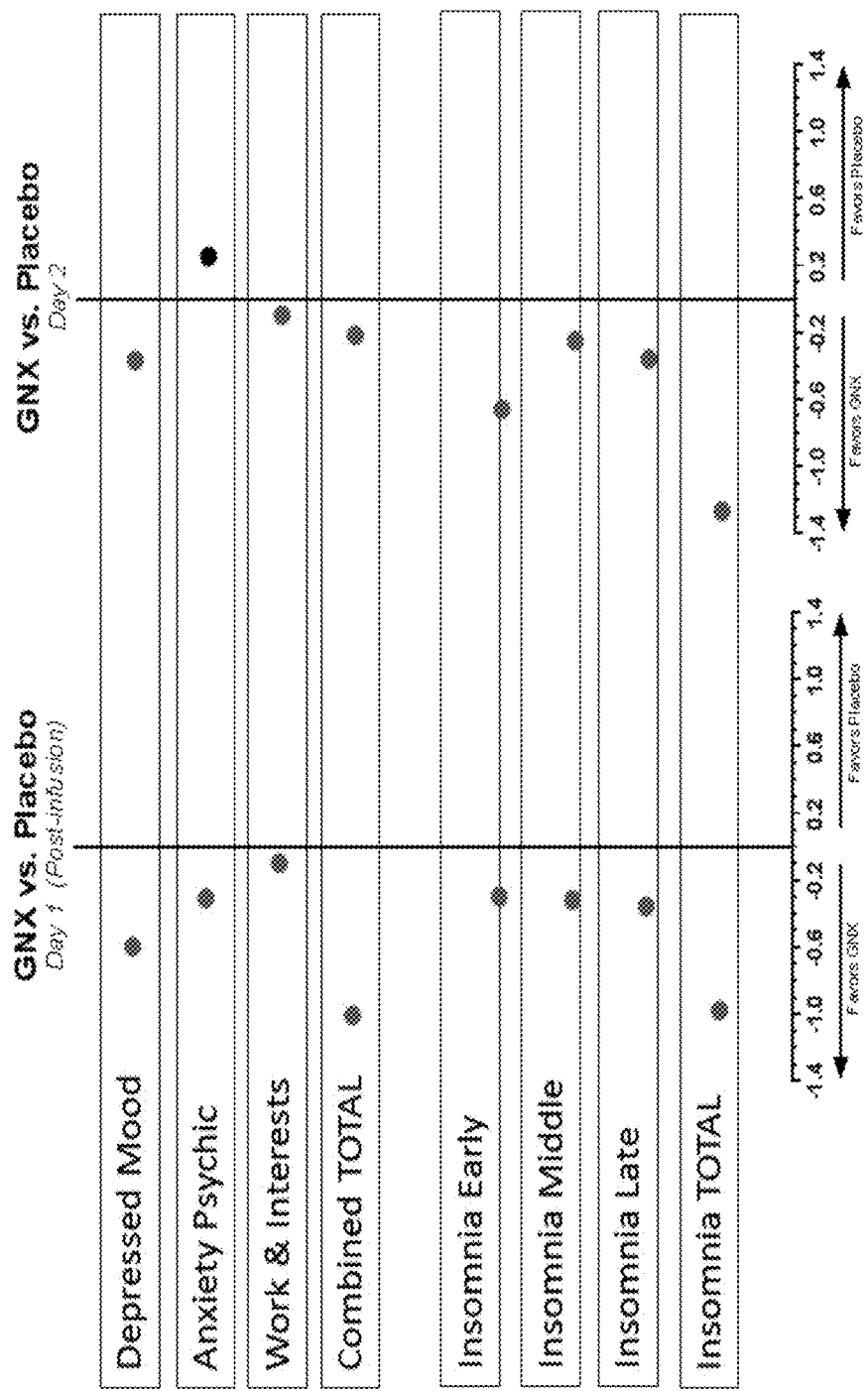
FIG. 28 depicts HAM-D17 item analysis at early time-points for Cohort 6.
Figure 29:
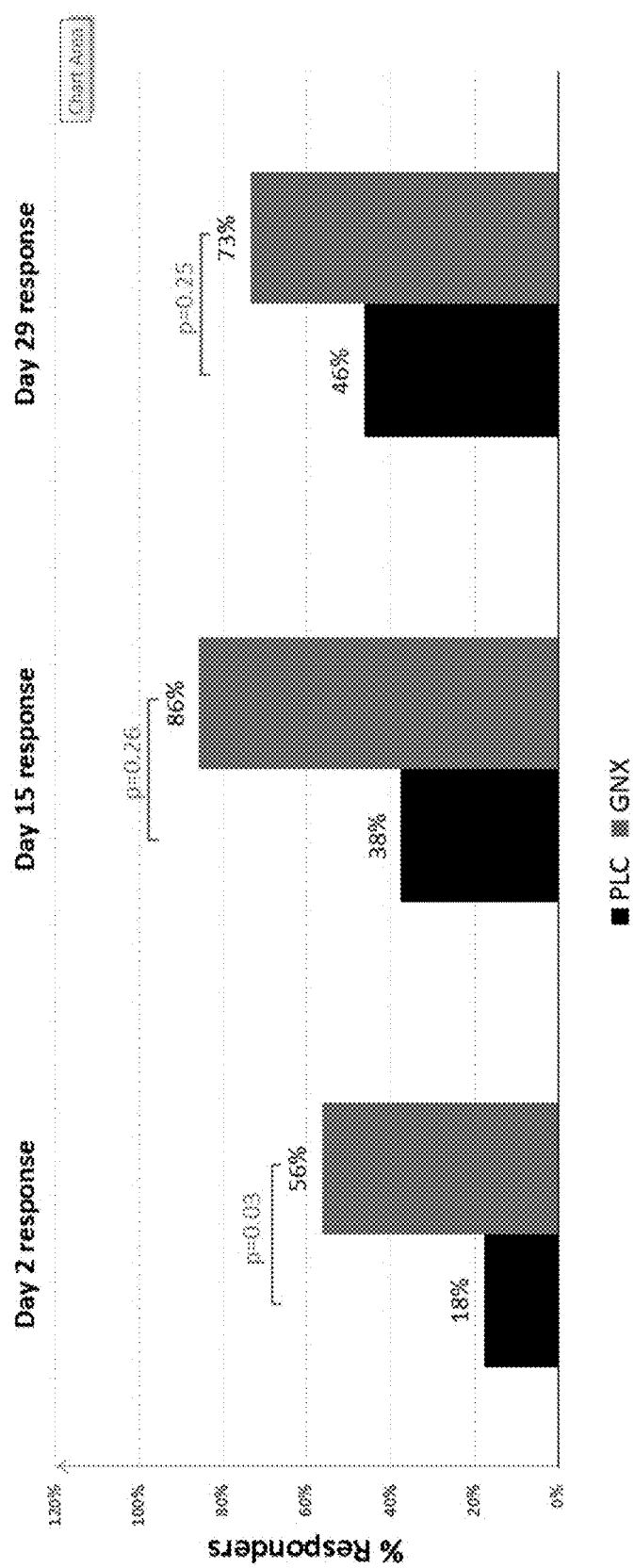
FIG. 29 depicts CGI-I mITT response rates at Day 2, Day 15 and Day 29 of Cohort 6.
Figure 30:
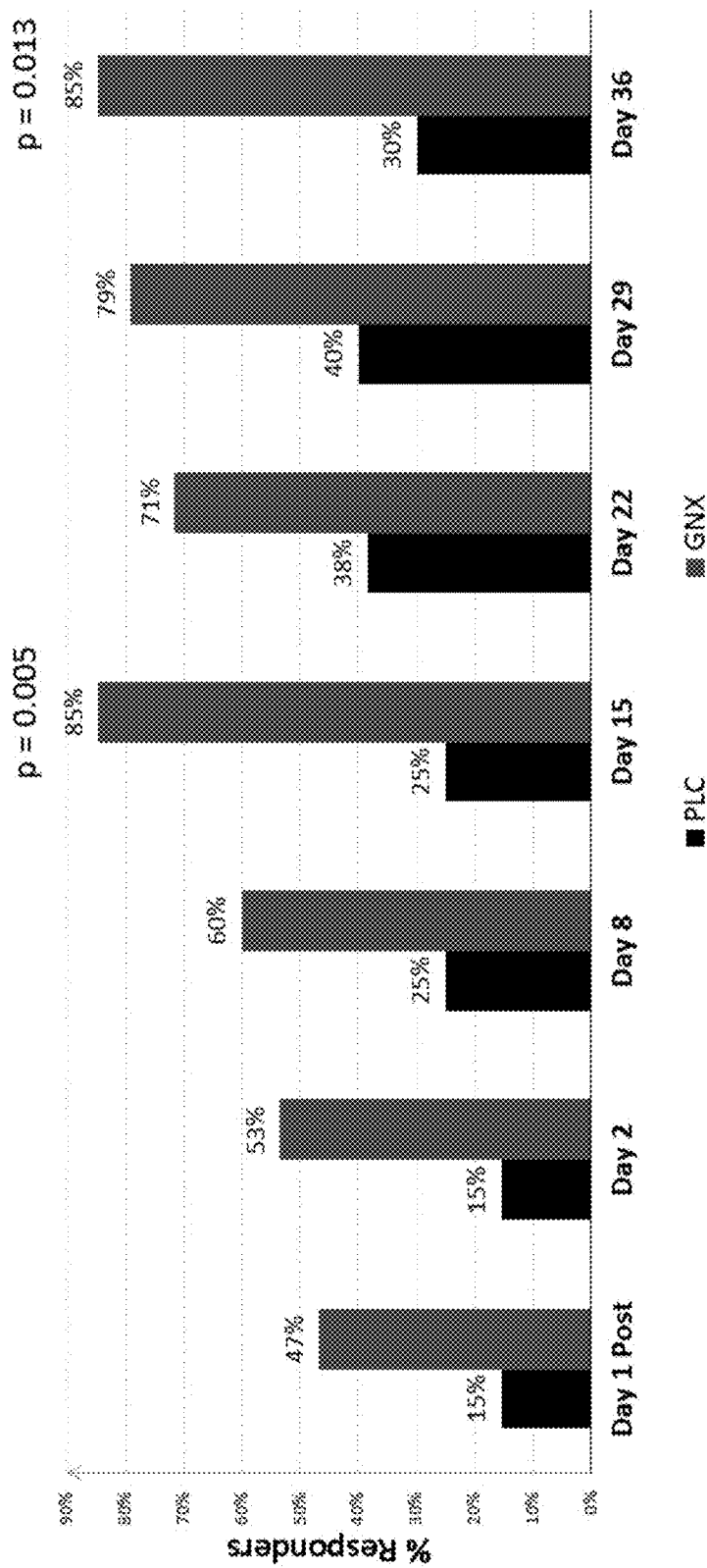
FIG. 30 depicts CGI-I response rates per protocol population and excluding patient 112-699.
Figure 31B:
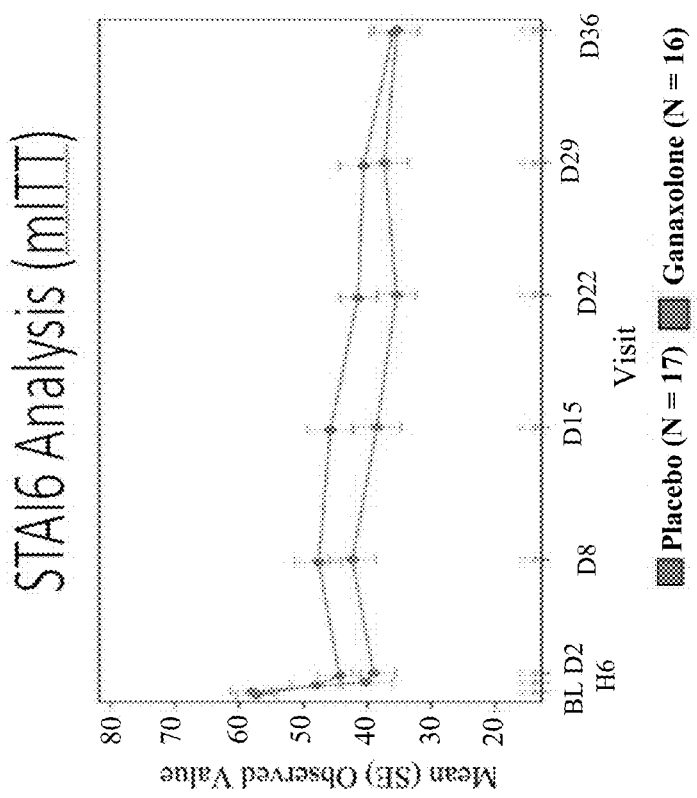
FIG. 31B depicts STAI6 Analysis (mITT). STAI6 is Spielverger State-Trait Anxiety Inventory, 6-item version. Post-baseline means are standard errors (SEs) are from a mixed model repeated measures (MMRM) analysis with baseline as a covariate. Decreasing scores indicate improvement. Numbers of observations are shown along the x-axis.
Figure 31A:
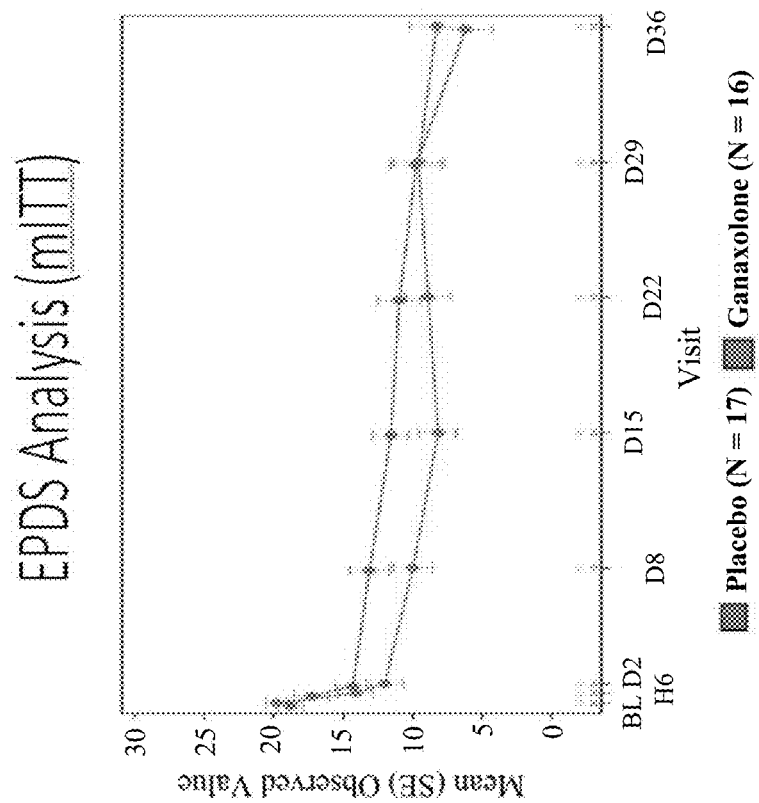
FIG. 31A depicts EPDS Analysis (mITT). EPDS is Edinburg Postnatal Depression Scale. Post-baseline means are standard errors (SEs) are from a mixed model repeated measures (MMRM) analysis with baseline as a covariate.
Figure 32:
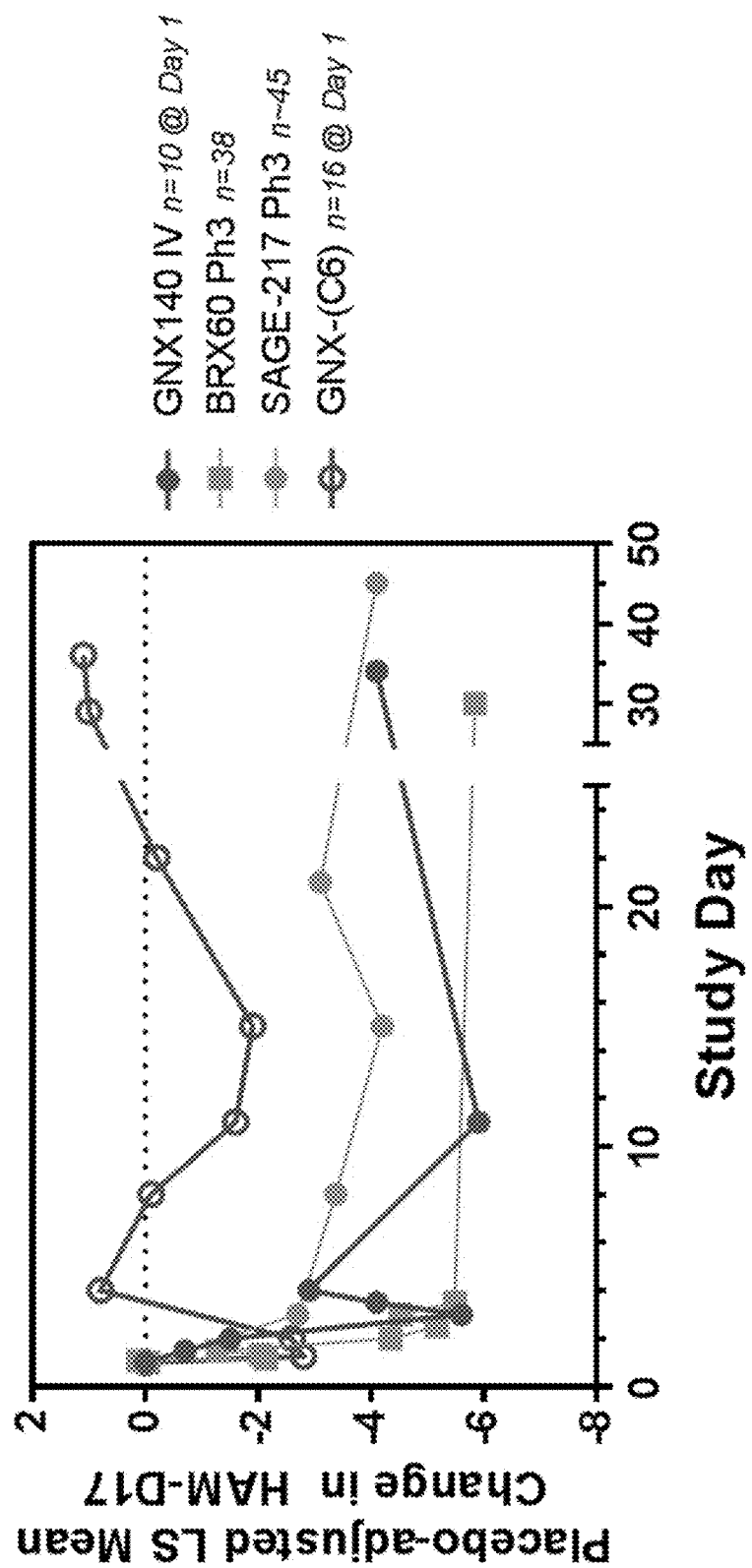
FIG. 32 depicts efficacy comparison across studies: active arms placebo adjusted LS Mean Change in HAM-D17. Sage-217 is zuranolone.
Figure 33:
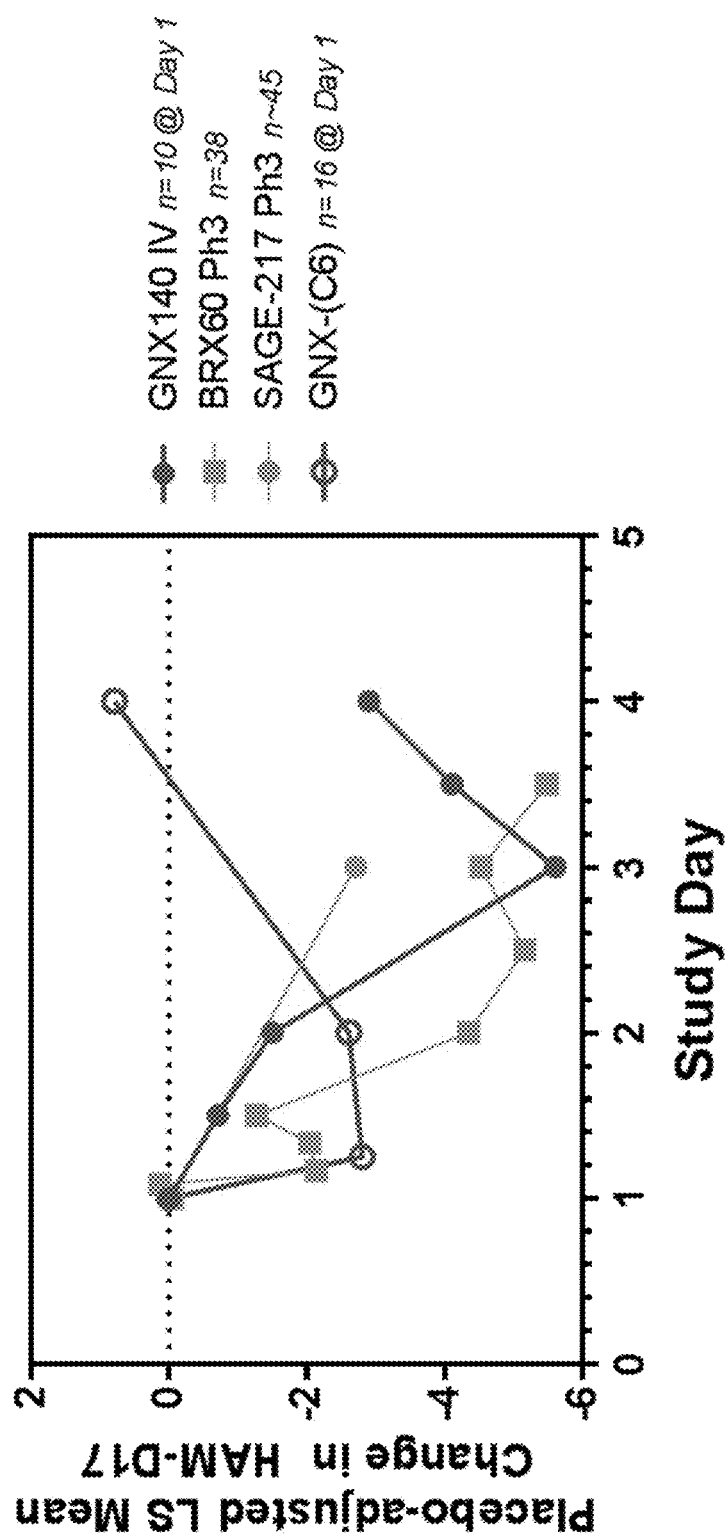
FIG. 33 depicts efficacy comparison across studies: placebo adjusted LS mean change in HAM-D17 (early).
Figure 34:
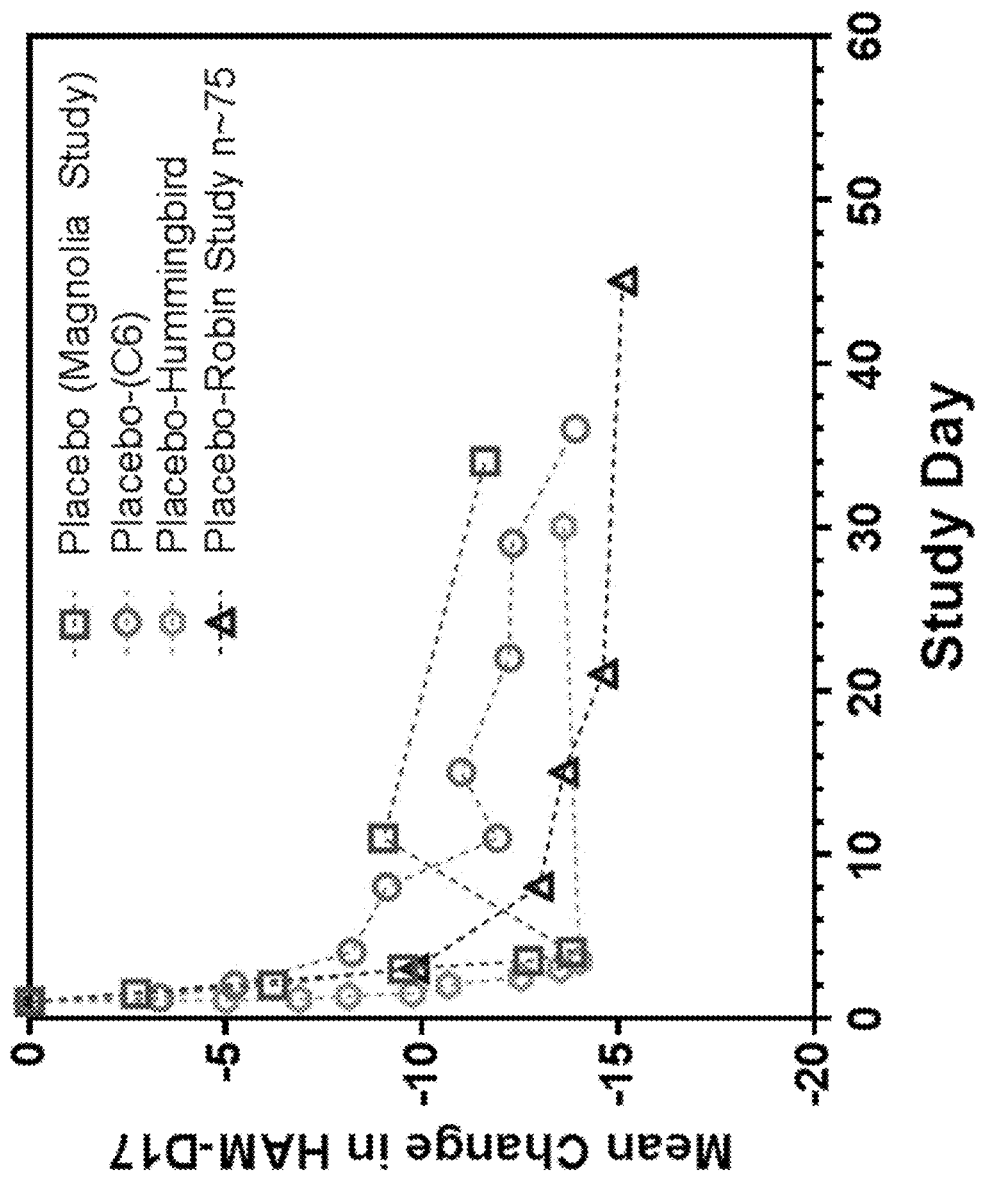
FIG. 34 depicts placebo response across studies.
Figure 35:
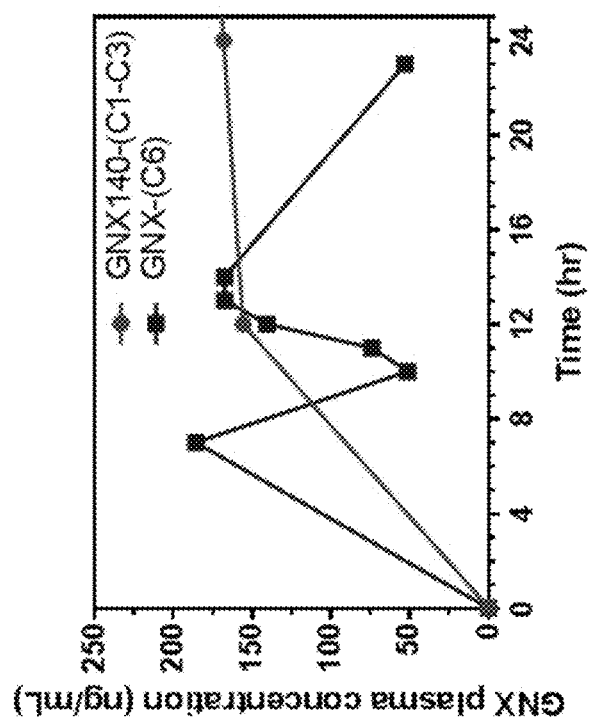
FIG. 35 depicts ganaxolone plasma concentrations for Cohorts 1 to 3 and 6.
Figure 36:
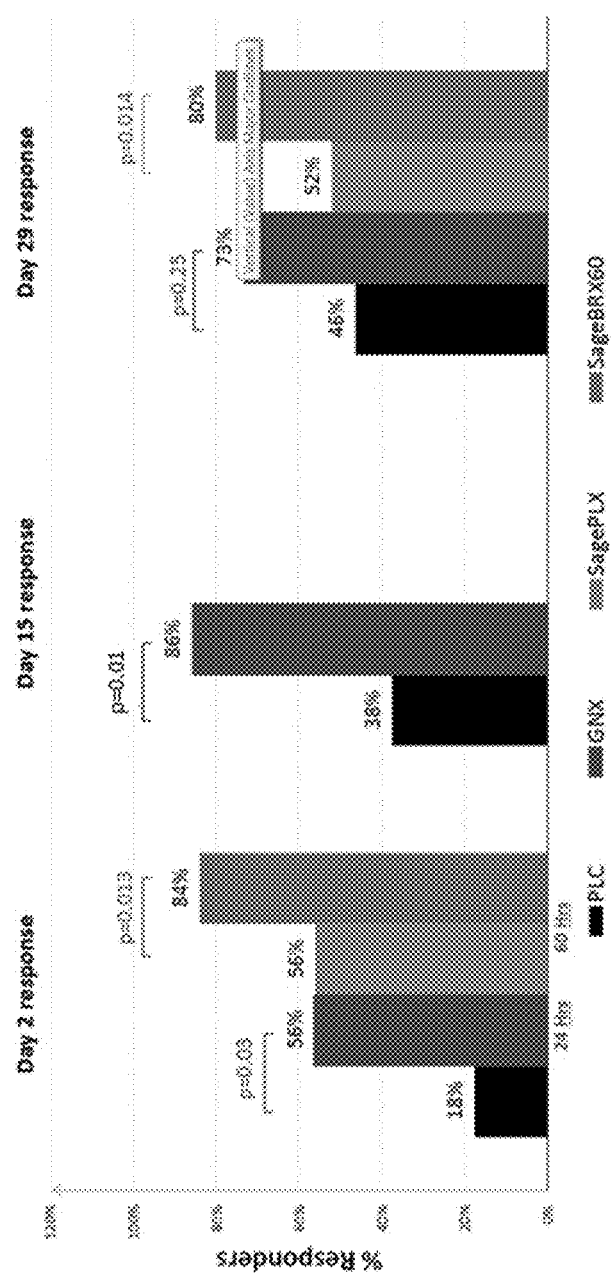
FIG. 36 depicts CGI-Response rates at day 2, day 15 and day 29 after administration of ganaxolone (Cohort 6) and the 60 µg brexanolone dose regimen. Day 15 p-value is 0.01.

The results are depicted in FIGS. 23A and 23B and summarized in Table 2.

TABLE 2

| | Placebo-adjusted difference | | | |
|---|---|---|---|---|
| | mITT | | PP (n-5) | |
| | 6 hours | Day 2 | 6 hours | Day 2 |
| Early efficacy (6 hours, Day2) | −2.8 | −2.6 | −3.4 | −2.7 |
| | Day 29 | | Day 29 | |
| Late efficacy (Day 29) | +1 | | −2.6 | |

Results support efficacy at the early timepoint—in fact, there is an effect at the 6 hour timepoint (the shortest infusion duration that was tested), and immediately after completion of IV treatment. HAMD17 decrease at 6 hours and on Day2 (both mITT, PP) favor ganaxolone. CGI-I decrease (both mITT, PP) also favors GNX. CGI-I change on Day2 $p<0.05$. The improvement was not just from insomnia items, and included, e.g., improvement in mood.

Although the results did not show efficacy at the late timepoint and intermediate timepoints during oral treatment under HAMD17 mITT analysis (HAMD17 were not different from placebo); under HAMD17 PP analysis and sensitivity by site analyses, HAMD17 change from baseline favors GNX after Day 2. CGI-I mITT and PP favors GNX at all timepoints at Day 2, Day 8, Day 15, Day 29 ($p<0.05$). Additional supportive evidence of efficacy was obtained from EPDS and STAI6 (numeric advantage at all timepoints till Day 29).

IV administration of ganaxolone at a rate of 20 mg/hr for 6 hours and oral administration of 900 mg of ganaxolone with dinner on Day1 showed >30% incidence of sedation and somnolence. Tolerability and safety data is summarized in Table 3 below.

TABLE 3

| TEAE | Placebo n (%) | Ganaxolone n (%) |
|---|---|---|
| Dizziness | 1 moderate (5.9) | 1 moderate (6.3) |
| Sedation | 1 mild (5.9) | 1 mild, 3 moderate (25) |
| Somnolence | 1 mild (5.9) | 0 |
| DC for AE | 1 (suicide attempt) | 0 |
| Dose reduction | 1 dizziness | 2 dizziness |
| | 1 headache | 1 somnolence |
| | | 1 sedation |
| | | 1 urticaria |

Oral administration of 900 mg ganaxolone with dinner was well tolerated after Day 2.

There were no serious adverse events or adverse events leading to treatment discontinuation were reported. Incidence of somnolence and sedation were 11.8% vs. 31.3% (placebo and ganaxolone, respectively). Somnolence and sedation lasted from 2 to 10 day, except one ongoing case. Tolerability was good after week 1.

Incidence of dizziness was 5.9% vs 25% (placebo and ganaxolone, respectively).

It was also concluded that oral daily administration of 900 mg ganaxolone may be adequate for future studies.

The results support a conclusion that weight-based ganaxolone IV dosing greater than 140 µg/kg/hr for 48 or 60 hours is likely to demonstrate efficacy.

The results also support a conclusion that oral administration of ganaxolone during ambulatory treatment is possible and may be efficacious.

Example 3

Approximately 172 women aged 18 to 48 years with PPD are screened, and approximately 88 subjects are enrolled into a Phase 2 clinical study. The enrolled subjects are assigned to five groups.

In the first group, approximately 8 subjects are titrated to a total daily oral dose of 900 mg ganaxolone per day (administered in three divided doses per day) over 10 days, followed by a taper over 4 days. For this group ganaxolone doses are titrated from 225 mg on Day 1 to a total daily oral dose of 900 mg starting on Day 7. The ganaxolone mean trough plasma concentrations during the Days 8, 9, and 10 are predicted to be about 40 ng/ml, based on PK modelling. Bedtime doses are selected to be higher than the daytime doses, and are expected to yield plasma mean peak concentrations up to 180 ng/ml during the night on Days 8, 9 and 10.

In the second group, approximately 20 subjects receive ganaxolone administered orally at bedtime (QHS). For these subjects, ganaxolone is titrated to a QHS dose of 675 mg over 4 days, which is then maintained until Day 10, followed by a taper over 4 days.

In the third group, approximately 20 subjects receive ganaxolone administered orally at a dose of 675 mg QHS for 28 days, followed by a taper over 4 days. The trough ganaxolone levels are expected to be below 40 ng/ml.

In the fourth group, approximately 20 subjects receive orally, on the first 2 days, ganaxolone capsules 675 mg at dinner time and 675 mg at bedtime (for a total of 1,350 mg per day on the first 2 days), followed by 26 days of ganaxolone capsules 1,125 mg at dinner time (high fat diet), and a taper over 4 days. The two evening 675 mg oral doses, within 3 hours of each other on Day 1 are expected to provide mean Cmax plasma concentrations of approximately 250-300 ng/mL. Twin evening dosing on Day 2 is expected to lead to similar exposure.

Figure 37:
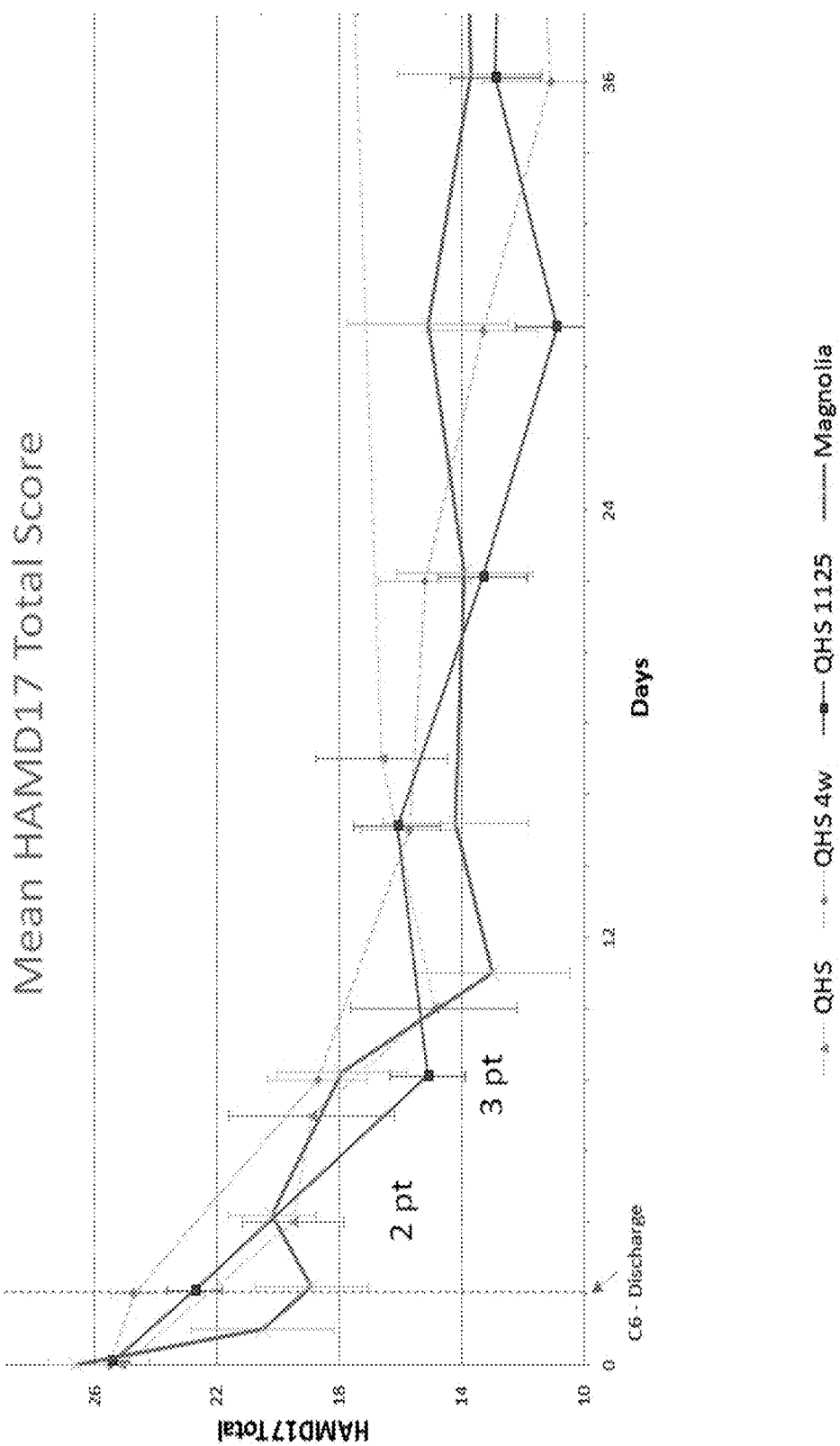
FIG. 37 depicts mean HAMD17 total scores. QHS: oral administration of 675 mg ganaxolone at bedtime for 14 days. QHS 4w: oral administration of 675 mg ganaxolone at bedtime for 4 weeks. QHS 1125: oral administration of 1125 mg ganaxolone for 4 weeks. *Magnolia*: IV administration of 20 mg/hour ganaxolone for 6 hours; then, oral administration of 675 mg ganaxolone at bedtime for 2 days; and, then, 900 mg for 26 days.
Figure 38:
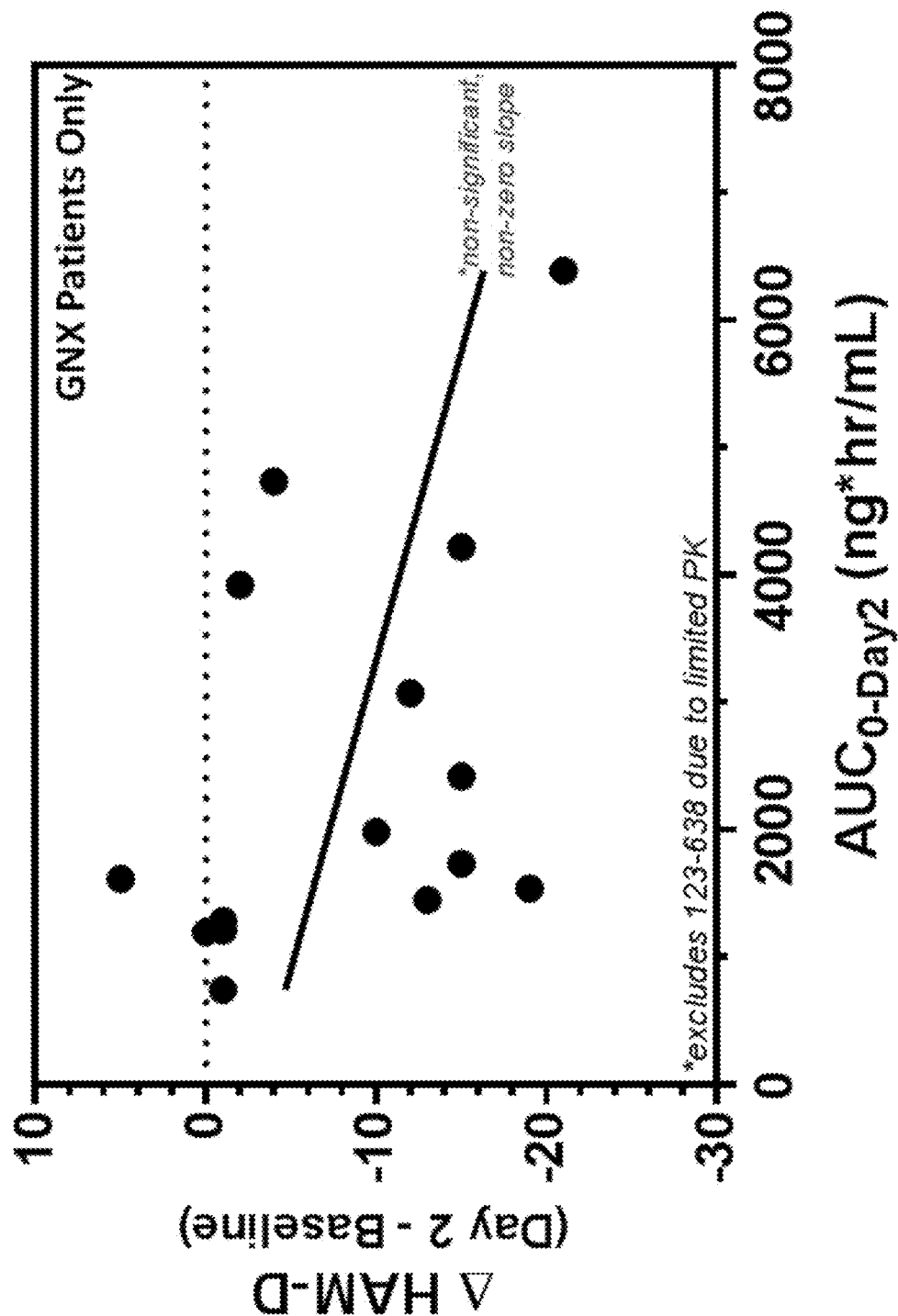
FIG. 38 depicts a graph of A HAM-D (Day 2—Baseline) versus estimated $AUC_{0-48}$ (ng*hr/ml).
Figure 39:
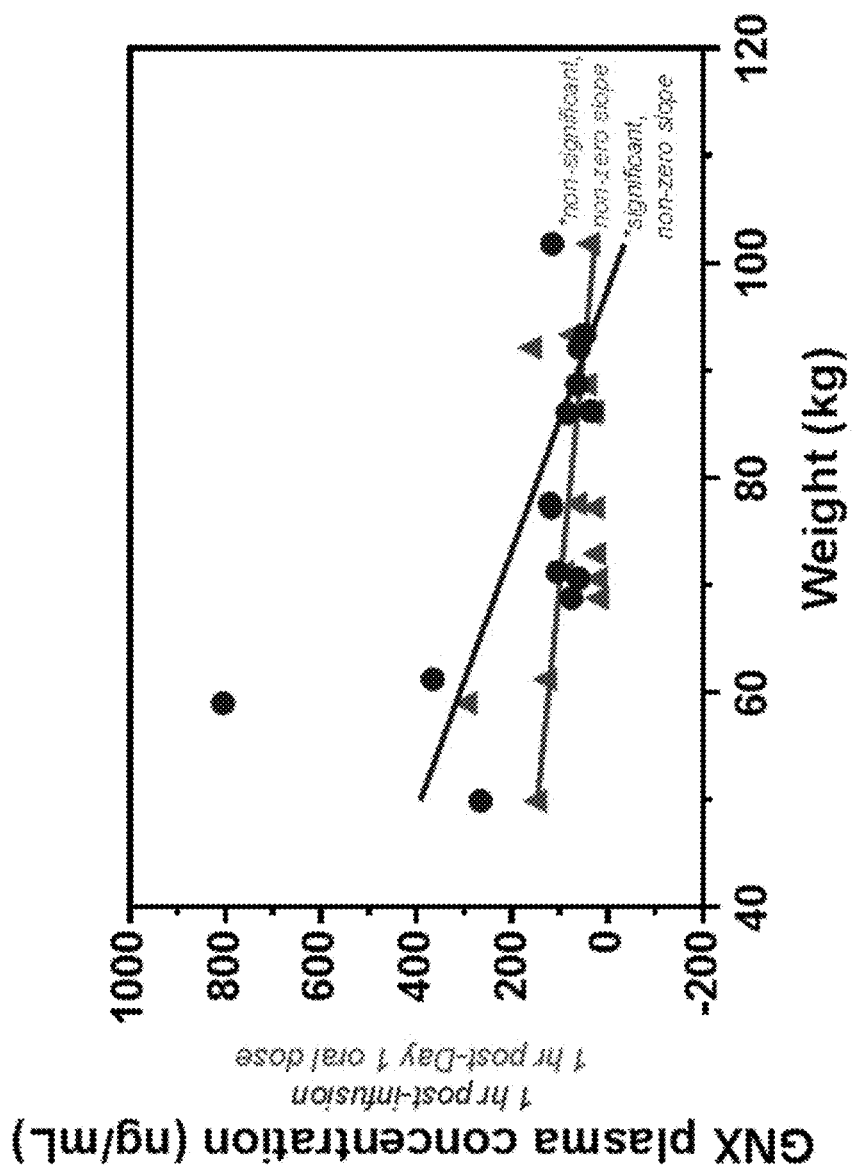
FIG. 39 depicts PK correlation to body weight. The graph shows modest relationship between plasma PK and body weight at 1 hour after IV infusion. No relationship during oral dosing.

FIG. 37 depicts mean HAMD17 total scores for these four groups.

In the fifth group, approximately 20 subjects receive ganaxolone as IV 12 mg bolus over 2 minutes at approximately 4 pm of the first day, followed by ganaxolone oral suspension 750 mg at dinner time (high fat diet), and 750 mg at bedtime (with a high fat snack) for a total of 1,512 mg on Day 1. On Day 2, subjects will receive ganaxolone oral suspension 750 mg at dinner time and 750 mg at bedtime, for a total of 1,500 mg, followed by 26 days of ganaxolone oral suspension 1,000 mg at dinner time and a taper over 4 days. This initial bolus infusion is targeted to provide a fast onset of antidepressant activity by delivery of rapid plasma exposures to ganaxolone. Together with the two evening 750 mg oral doses within 3 hours of each other, Day 1 dosing is expected to provide mean $C_{max}$ plasma concentrations of approximately 250-300 ng/mL, which may be mildly sedating. Two evening 750 mg oral doses within 3 hours of each other on Day 2 are expected to lead to similar exposure.

Example 4 (Comparison of Studies)

Efficacies of the regimen of Cohort 6 (20 mg/hr IV for 6 hours, followed by 900 mg orally at bedtime for 28 days, followed by taper over 3 days (675 mg PO HS on day 29, 450 mg PO HS on day 30, and 225 mg PO HS on day 31)), the 140 μg/kg/hr ganaxolone, the 60 μg brexanolone dose regimen, and Sage-217 (oral administration of zuranolone 30 mg daily for 28 days) were compared. The results of comparison are depicted in FIGS. 32-34 and 36.

What is claimed is:

1. A method of treating postpartum depression, comprising administering ganaxolone to a female within twelve months of childbirth parenterally at a dose from about 86 μg/kg/hr to about 260 μg/kg/hr over a time period of from about 6 hours to about 72 hours, and wherein the administration alleviates or reduces severity of at least one symptom of postpartum depression.

2. The method of claim 1, wherein ganaxolone is administered via an intravenous infusion over about 48 hours.

3. The method of claim 2, further comprising oral administration of ganaxolone after the intravenous infusion.

4. The method of claim 3, wherein said oral administration comprises orally administering from about 400 mg to about 2000 mg ganaxolone daily in one, two or three divided doses.

5. The method of claim 2, further comprising administering a bolus dose of ganaxolone intravenously before the intravenous infusion, the bolus dose comprising an amount of ganaxolone sufficient to provide ganaxolone $C_{max}$ of from about 200 ng/ml to about 400 ng/ml within 5 minutes of the bolus administration.

6. The method of claim 3, wherein the oral administration is for a time period of from about 2 days to about 6 months.

7. The method of claim 2, wherein from about 150 mg to about 900 mg of ganaxolone is administered during the intravenous infusion.

8. The method of claim 2, wherein from about 70% to about 95% of total ganaxolone dose administered during the intravenous infusion is administered at a first constant rate, and from about 5% to about 30% of the total ganaxolone dose is administered at a second constant rate.

9. The method of claim 8, wherein the first constant rate is greater than the second constant rate, and the first constant rate is from about 1.5 mg/hr to about 35 mg/hr.

10. The method of claim 1, wherein said administration provides an average plasma concentration of ganaxolone of from about 91 ng/ml to about 275 ng/ml over 48 hours, and alleviates or reduces severity of at least one symptom of postpartum depression at about 6 hours after the start of the administration.

11. The method of claim 1, wherein said administration provides ganaxolone $AUC_{12-24}$ of from about 1035 ng*hr/ml to about 3131 ng*hr/ml.

12. A method of treating postpartum depression, comprising administering ganaxolone to a female within twelve months of childbirth parenterally at a dose from about 86 μg/kg/hr to about 260 μg/kg/hr, over a time period of from about 24 hours to about 72 hours, and wherein the administration provides ganaxolone $AUC_{24-48}$ of from about 2301 ng*hr/ml to about 6958 ng*hr/ml and alleviates or reduces severity of at least one symptom of postpartum depression.

13. The method of claim 12, wherein the dose is from about 110 μg/kg/hr to about 260 μg/kg/hr.

14. The method of claim 13, wherein ganaxolone is administered via an intravenous infusion over about 60 hours.

15. The method of claim 14, wherein the intravenous infusion is followed by oral administration of ganaxolone.

16. The method of claim 15, wherein said oral administration comprises oral administration of from about 400 mg to about 2000 mg ganaxolone daily in one, two or three divided doses.

17. The method claim 14, further comprising administering a bolus dose of ganaxolone intravenously before the intravenous infusion, the bolus dose comprising an amount of ganaxolone sufficient to provide ganaxolone $C_{max}$ of from about 200 ng/ml to about 400 ng/ml.

18. The method of claim 12, wherein said administration alleviates or reduces severity of at least one symptom of postpartum depression at about 4 to about 8 hours after the start of the administration.

19. A method of treating postpartum depression, comprising administering a therapeutic dose of ganaxolone to a female within twelve months of childbirth in a manner which provides an average plasma concentration of ganaxolone of from about 90 ng/ml to about 300 ng/ml over a 24-hour period, and a first peak in the plasma concentration of ganaxolone and a second peak during said 24-hour period,
wherein the first peak is provided by an intravenous infusion of ganaxolone, and the second peak is provided by administration of an oral dose of ganaxolone, and
the administration of the therapeutic dose alleviates or reduces severity at least one symptom of postpartum depression at about 4 to about 6 hours after the start of the administration of the therapeutic dose.

20. The method of claim 19, wherein the intravenous infusion is over about 60 hours.

* * * * *